(12) United States Patent
Scheer et al.

(10) Patent No.: US 10,941,190 B2
(45) Date of Patent: Mar. 9, 2021

(54) PRODUCTION OF HETEROMULTIMERIC PROTEINS USING MAMMALIAN CELLS

(71) Applicant: Genentech, Inc., South San Francisco, CA (US)

(72) Inventors: Justin Scheer, San Francisco, CA (US); Whitney Shatz, San Francisco, CA (US); Domingos Ng, San Francisco, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 15/344,123

(22) Filed: Nov. 4, 2016

(65) Prior Publication Data

US 2017/0260252 A1 Sep. 14, 2017

Related U.S. Application Data

(63) Continuation of application No. PCT/US2015/029546, filed on May 6, 2015.

(60) Provisional application No. 61/989,509, filed on May 6, 2014.

(51) Int. Cl.

| | | |
|---|---|---|
| C07K 16/00 | (2006.01) | |
| C07K 16/46 | (2006.01) | |
| C07K 1/00 | (2006.01) | |
| C07K 1/02 | (2006.01) | |
| C12P 21/02 | (2006.01) | |
| C12P 21/00 | (2006.01) | |
| C12N 15/79 | (2006.01) | |
| C12N 15/90 | (2006.01) | |

(52) U.S. Cl.
CPC ............ *C07K 16/00* (2013.01); *C07K 16/468* (2013.01); *C07K 2317/14* (2013.01); *C07K 2317/31* (2013.01); *C07K 2317/52* (2013.01); *C07K 2317/526* (2013.01); *C07K 2317/53* (2013.01); *C12N 15/79* (2013.01); *C12N 15/907* (2013.01)

(58) Field of Classification Search
CPC .. C07K 16/00; C07K 2317/31; C07K 16/468; C07K 2317/52; C07K 2317/522; C07K 2317/524; C07K 2317/526; C07K 2317/53; C07K 2317/14; A61K 2039/505
See application file for complete search history.

(56) References Cited

U.S. PATENT DOCUMENTS

| | | |
|---|---|---|
| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 5,122,469 A | 6/1992 | Mather et al. |
| 5,731,168 A | 3/1998 | Carter et al. |
| 6,331,415 B1 | 12/2001 | Cabilly et al. |
| 6,534,628 B1 | 3/2003 | Nilsson et al. |
| 6,660,843 B1 | 12/2003 | Feige et al. |
| 7,612,181 B2 | 11/2009 | Wu et al. |
| 7,642,228 B2 | 1/2010 | Carter et al. |
| 9,637,557 B2 | 5/2017 | Scheer et al. |
| 9,862,778 B2 * | 1/2018 | Giese .................. C07K 16/468 |
| 2003/0078385 A1 | 4/2003 | Arathoon et al. |
| 2007/0178552 A1 | 8/2007 | Arathoon et al. |
| 2009/0182127 A1 | 7/2009 | Kjaergaard et al. |
| 2010/0249379 A1 | 9/2010 | Goepfert et al. |
| 2011/0287009 A1 * | 11/2011 | Scheer ................ C07K 16/244 424/136.1 |
| 2012/0164726 A1 | 6/2012 | Klein et al. |

FOREIGN PATENT DOCUMENTS

| | | |
|---|---|---|
| AU | 2008234248 A1 | 10/2008 |
| CA | 2796181 A1 | 10/2011 |
| CN | 102946906 A | 2/2013 |
| RU | 2624027 C2 | 6/2017 |
| WO | 87/00195 | 1/1987 |
| WO | 90/03430 | 5/1990 |
| WO | WO-1992/10209 A1 | 6/1992 |
| WO | 94/11026 | 5/1994 |
| WO | 96/27011 | 9/1996 |
| WO | 98/50431 | 11/1998 |
| WO | WO02100348 A2 | 12/2002 |
| WO | WO-2004/009618 A2 | 1/2004 |
| WO | WO-2004/009618 A3 | 1/2004 |
| WO | WO2004035607 A2 | 4/2004 |
| WO | WO-2006/028936 A2 | 3/2006 |
| WO | WO-2006/028936 A3 | 3/2006 |
| WO | 2007/147901 | 12/2007 |
| WO | WO-2008/119353 A1 | 10/2008 |
| WO | 2009/089004 A1 | 7/2009 |
| WO | 2011/034605 | 3/2011 |
| WO | 2011/133886 | 10/2011 |

(Continued)

OTHER PUBLICATIONS

Barnes et al., "Methods for Growth of Cultured Cells in Serum-Free Medium" Analytical Biochemistry 102:255-270 ( 1980).

(Continued)

*Primary Examiner* — Phuong Huynh

(74) *Attorney, Agent, or Firm* — Morrison & Foerster LLP

(57) ABSTRACT

Described herein are methods for the efficient production of antibodies and other multimeric protein complexes (collectively referred to herein as heteromultimeric proteins) capable of specifically binding to more than one target. The targets may be, for example, different epitopes located on a single molecule or located on different molecules.

12 Claims, 9 Drawing Sheets

(56) References Cited

FOREIGN PATENT DOCUMENTS

| WO | WO-2011131746 A2 * | 10/2011 | ......... C07K 16/1063 |
|---|---|---|---|
| WO | WO2012106587 A1 | 8/2012 | |
| WO | WO-2013055958 A1 * | 4/2013 | ........... C07K 16/468 |
| WO | 2013/055958 | 5/2013 | |

OTHER PUBLICATIONS

Berg et al., "Bispecific Antibodies that Mediate Killing of Cells Infected with Human Immunodeficiency Virus of any Strain" Proc. Natl. Acad. Sci USA 88:4723-4727 (Jun 1991).

Bloom et al., "Intrachain Disulfide Bond in the Core Hinge Region Human IgG4" Protein of Science 6:407-415 ( 1997).

Bostrom et al., "Variants of the Antibody Herceptin That Interact with HER2 and VEGF at the Antigen Binding Site" Science 323:1610-1614 (Mar 20, 2009).

Burton, "Immunoglobulin G: Functional Sites" Molecular Immunology 22(3):161-206 ( 1985).

Chamow et al., "A Humanized, Bispecific Immunoadhesin-Antibody that Retargets CD3+ Effectors to Kill HIV-1-Infected Cells" Journal of Hematotherapy 4:439-446 ( 1995).

Fischer et al., "Bispecific Antibodies: Molecules That Enable Novel Therapeutic Strategies" Pathbiology 74:3-14 ( 2007).

Graham et al., "Characteristics of a Human Cell Line Transformed by DNA from Human Adenovirus Type 5" J. Gen. Virol. 36:59-72 ( 1977).

Gronwall et al., "Generation of Affibody ligands binding interleukin-2 receptor a/CD25" Biotechnol. Appl. Biochem. 50:97-112 ( 2008).

Humphreys et al., "Formation of dimeric Fabs in *Escherichia coli*: effect of hinge size and isotype, presence of interchain disulphide bond, Fab' expression levels, tail piece sequences and growth conditions" Journal of Immunological Methods 209:193-202 ( 1997).

"International Search Report" (dated Aug. 2015).

Jin et al., "MetMAb, the One-Armed 5D5 Anti-c-Met Antibody, Inhibits Orthotopic Pancreatic Tumor Growth and Improves Survival" Cancer Res 68(11):4360-4368 (Jun. 1, 2008).

Kontermann, "Recombinant Bispecific Antibodies for Cancer Therapy" Acta Pharmacologica Sinica 26(1):1-9 ( 2005).

Lee et al., "Expression and functional reconstitution of a recombinant antibody (Fab') specific for human apolipoprotein B-100" Journal of Biotechnology 101:189-198 ( 2003).

Martens et al., "A Novel One-Armed Anti-c-Met Antibody Inhibits Glioblastoma Growth in vivo" Clin Cancer Res 12(20):6144-6152 (Oct. 15, 2006).

Marvin et al., "Recombinant approacehs to IgG-like bispecific antibodies" Acta Pharmacologica Sinica 26(6):649-658 (Jun. 2005).

Mather et al., "Culture of Testicular Cells in Hormone-Supplemented Serum-Free Medium" Annals New York Academy of Sciences 383:44-68 ( 1982).

Mather, "Establishment and Characterization of Two Distinct Mouse Testicular Epithelial Cell Lines" Biology of Reproduction 23:243-252 ( 1980).

Nord et al., "A combinatorial library of an a-helical bacteria receptor domain" Protein Engineering 8(6):601-608 ( 1995).

Nord et al., "Binding proteins selected from combinatorial libraries of an a-helical bacterial receptor domain" Nature Biotechnology 15:772-777 (Aug. 1997).

Pack et al., "Improved Bivalent Miniantibodies, with Identical Avidity as Whole Antibodies, Produced by High Cell Density Fermentation of *Escheria coli*" Biotechnology 11:1271-1277 (Nov. 1993).

Pack et al., "Miniantibodies: Use of Amphipathic Helices to Produce Functional, Flexibly Liked Dimeric Fv Fragments with High Avidity in *Escherichia coli*" Biochemistry 31(6):1579-1584 ( 1992).

Papadea et al., "Human Immunoglobulin G and Immunoglobulin G Subclasses: Biochemical, Genetic, and Clinical Aspects" Critical Reviews in Clinical Laboratory Sciences 27(1):27-58 ( 1989).

Spiess et al., "Bispecific antibodies with natural architecture produced by co-culture of bacteria expressing two distinct half-antibodies" Nature Biotechnology 31(8):753-758 (Aug. 2013).

Urlaub et al., "Isolation of Chinese hamster cell mutants deficient in dihydrofolate reductase activity" Proc. Natl. Acad. Sci. USA 77(7):4216-4220 (Jul. 1980).

Wibbenmeyter et al., "Cloning, expression, and characterization of the Fab fragment of the anti-lysozyme antibody HyHEL-5" Biochimica et Biophysica Acta 1430:191-202 ( 1999).

Zhu et al., "Remodeling domain interfaces to enhance heterodimer formation" Protein Science 6:781-788 ( 1997).

Clackson, T. et al. (Aug. 15, 1991). "Making Antibody Fragments Using Phage Display Libraries," Nature 352:624-628.

Kostelny, S.A. et al. (Mar. 1, 1992). "Formation of a Bispecific Antibody by the Use of Leucine Zippers," Journal of Immunology 148(5):1547-1553.

Portolano, S. et al. (Feb. 1, 1993). "Lack of Promiscuity in Autoantigen-Specific H and L Chain Combinations as Revealed by Human H and L Chain "Roulette"," Journal of Immunology 150(3):880-887.

Shatz, W. et al. (Sep. 2016, e-pub. Sep. 28, 2016). "An Efficient Route to Bispecific Antibody Production Using Single-Reactor Mammalian Co-Culture," MABS 8(8):1487-1497.

European Partial Search Report dated Nov. 13, 2017, for European Patent Application No. 15789583.0, filed on Nov. 12, 2015, 13 pages.

Supplemental European Search Report dated Feb. 14, 2018, for European Patent Application No. 15789583.0, filed on Nov. 12, 2015, 13 pages.

Rispens, T. et al. (May 31, 2011). "Mechanism of Irnmunoglobulin G4 Fab-arm Exchange," J. Am. Chem. Soc. 133:10302-10311.

Shatz, W. et al. (Nov./Dec. 2013, e-pub. Aug. 29, 2013). Knobs-Into-Holes Antibody Production in Mammalian Cell Lines Reveals That Asymmetric Afucosylation is Sufficient for Full Antibody-Dependent Cellular Cytotoxicity , mAbs 5(6):872-881.

Declaration of Dr. Aran F. Labrijn and Curriculum Vitae Aran F. Labrijn, dated Dec. 11, 2018, for European Patent No. 2560683, in the Name of F. Hoffmann-La Roche AG, Opposition thereto by Genmab A/S, 30 pages.

European Interlocutory Decision Apr. 11, 2019, for European Patent Application No. 11718831,8, 35 pages.

European Opposition J A Kemp, Dec. 13, 2018, for European Patent Application No. 11718831.8, F. Hoffmann-La Roche AG, 14 pages.

Kabat, E.A. (1991). Sequences of Proteins of Immunological Interest, 5th Edition, U.S. Department of Health and Human Services, NIH Publication No. 91-3242, p. 689.

Labrijn, A.F. et al. (2013). "Supplemental Information. Efficient Generation of stable Bispecific IgG1 by Controlled Fab-arm Exchange," Proc. Natl. Acad. Sci. USA pp. 1-10.

Labrijn, A.F. et al. (Mar. 26, 2013). "Efficient Generation of stable Bispecific IgG1 by Controlled Fab-arm Exchange," Proc. Natl. Acad. Sci. USA 110(13):5145-5150.

Liu, H. et al. (2012). "Disulfide Bond Structures of IgG Molecules. Structural Variations, Chemical Modifications and Possible Impacts to Stability and Biological Function," mAbs 4(1):17-23.

Plomp, R. et al. (2015). "Hinge-region O-Glycosylation of Human Immunoglobulin G3 (IgG3)," Mol. & Cell Proteomics 14(5):1373-1384.

Vidarsson, G. et al. (Oct. 20, 2014). "IgG Subclasses and Allotypes: From Structure to Effector Functions," Frontiers in Immunology 5(520):1-17.

Wranik, B.J. et al. (Dec. 21, 2012). "LUZ-Y, a Novel Platform for the Mammalian Cell Production of Full-Length IgG-bispecific Antibodies," The Journal of Biological Chemistry 287(52):43331-43339.

* cited by examiner

ION EXCHANGE ASSAY

REVERSE PHASE ASSAY

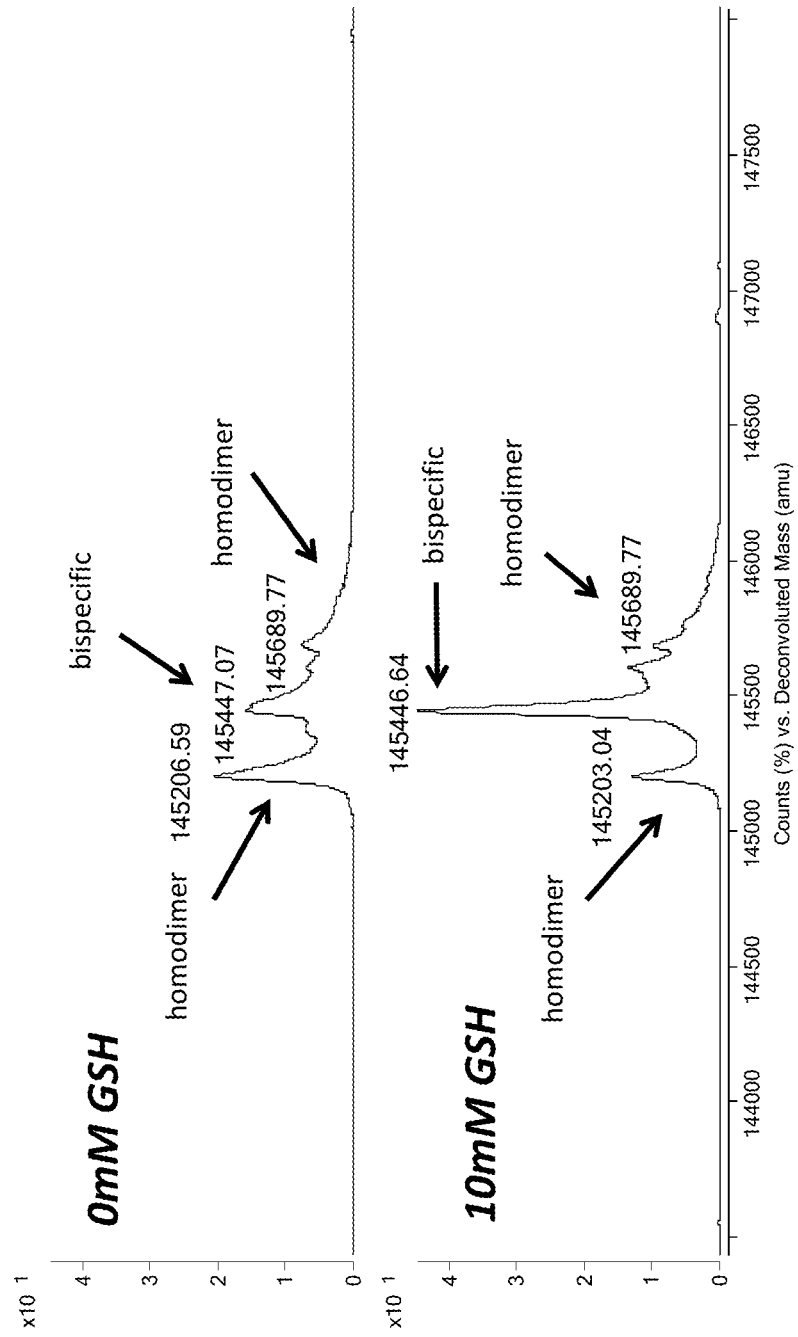

PRODUCTION OF HETEROMULTIMERIC PROTEINS USING MAMMALIAN CELLS

CROSS REFERENCE TO RELATED APPLICATIONS

This application is a continuation of International Application No. PCT/US2015/029546 having an international filing date of May 6, 2015, which claims the benefit of priority under 35 U.S.C. § 119 to U.S. Provisional Application No. 61/989,509 filed May 6, 2014. The contents of both applications are herein incorporated be reference in their entirely.

TECHNICAL FIELD

This invention relates to methods for the production of heteromultimeric proteins.

BACKGROUND

Monoclonal antibodies of the IgG type contain two identical antigen-binding arms and a constant domain (Fc). Antibodies with a differing specificity in their binding arms usually do not occur in nature and, therefore, have to be crafted with the help of chemical engineering (e.g., chemical cross-linking, etc), recombinant DNA and/or cell-fusion technology.

Bispecific antibodies can bind simultaneously two different antigens. This property enables the development of therapeutic strategies that are not possible with conventional monoclonal antibodies. The large panel of imaginative bispecific antibody formats that has been developed reflects the strong interest for these molecules. See Berg J, Lotscher E, Steimer K S, et al., "Bispecific antibodies that mediate killing of cells infected with human immunodeficiency virus of any strain," Proc Natl Acad Sci USA (1991) 88(11): 4723-4727 and Fischer N and Leger O., "Biospecific Antibodies: Molecules That Enable Novel Therapeutic Strategies," Pathobiology (2007) 74:3-14.

Another class of multispecific molecules is recombinant fusion proteins. Recombinant fusion proteins consisting of the extracellular domain of immunoregulatory proteins and the constant (Fc) domain of immunoglobulin (Ig) represent a growing class of human therapeutics. Immunoadhesins combine the binding region of a protein sequence, with a desired specificity, with the effector domain of an antibody. Immunoadhesins have two important properties that are significant to their potential as therapeutic agents: the target specificity, and the pharmacokinetic stability (half-life in vivo that is comparable to that of antibodies). Immunoadhesins can be used as antagonist to inhibit or block deleterious interactions or as agonist to mimic or enhance physiological responses. See Chamow S M, Zhang D Z, Tan X Y, et al., "A humanized, bispecific immunoadhesin-antibody that retargets CD3+ effectors to kill HIV-1-infected cells," J Hematother 1995; 4(5): 439-446.

Other multispecific molecules have been discussed elsewhere. Examples include but are not limited to: Fisher et al., Pathobiology (2007) 74:3-14 (review of various bispecific formats); U.S. Pat. No. 6,660,843, issued Dec. 9, 2003 to Feige et al. (peptibodies); US Pat. Publ. No. 2002-004587 published Jan. 10, 2002 (multispecific antibodies); U.S. Pat. No. 7,612,181 issued Nov. 3, 2009 to Wu et al. (Dual Variable Domain format); U.S. Pat. No. 6,534,628, Nord K et al., Prot Eng (1995) 8:601-608, Nord K et al., Nat Biotech (1997) 15:772-777, and Grönwall et al., Biotechnol Appl Biochem. (2008) June; 50(Pt 2):97-112 (Affibodies); Martens et al., Clin Cancer Res (2006), 12: 6144-6152 and Jin et al., Cancer Res (2008) 68(11):4360-4368 (one armed antibodies); Bostrom et al., Science (2009) 323:1610-1614 (Dual Action Fab, aka mixed valency antibodies). Other formats are known to those skilled in the art.

The manufacturing of clinical grade material remains challenging for the multispecific molecules described above. As noted above, there are many paths to the production of molecules with mixed binding arms, i.e., binding arms that are not identical to each other. Each of these methods has its drawbacks.

Chemical cross-linking is labor intensive as the relevant species may yet need to be purified from homodimers and other undesired by-products. In addition, the chemical modification steps can alter the integrity of the proteins thus leading to poor stability. Thus, this method is often inefficient and can lead to loss of antibody activity.

Cell-fusion technology (e.g., hybrid hybridomas) express two heavy and two light chains that assemble randomly leading to the generation of 10 antibody combinations. The desired heteromultimeric antibodies are only a small fraction of the antibodies thus produced. Purification of the desired heteromultimeric proteins dramatically reduces production yields and increases manufacturing costs.

Recombinant DNA techniques have been used to generate various heteromultimeric formats, e.g., single chain Fv, diabodies, etc., that do not comprise an Fc domain. A major drawback for this type of antibody molecule is the lack of the Fc domain and thus the ability of the antibody to trigger an effector function (e.g., complement activation, Fc-receptor binding etc.). Thus, a bispecific antibody comprising a functional Fc domain is desired.

Recombinant DNA techniques have also been used to generate 'knob into hole' bispecific antibodies. See US Patent Application 20030078385 (Arathoon et al.—Genentech). One constraint of this strategy is that the light chains of the two parent antibodies have to be identical to prevent mispairing and formation of undesired and/or inactive molecules due to being expressed in the same cell.

Thus, there remains a need for alternative methods of producing heteromultimeric proteins. The invention described herein provides such methods. These and other aspects and advantages of the invention will be apparent from the description of the invention provided herein.

BRIEF SUMMARY OF THE INVENTION

The invention provides efficient and novel methods of producing multispecific immunoglobulin complexes (e.g., multispecific antibodies) and other multimeric proteins (collectively referred to herein as heteromultimeric proteins) in mammalian cells over methods known in the art. See WO2013/055958 and WO2011/133886.

Thus, in a first aspect, provided are methods of preparing a heteromultimeric protein comprising i) a first hinge-containing polypeptide having a first heterodimerization domain, wherein the first hinge-containing polypeptide is associated with a first light chain, and ii) a second hinge-containing polypeptide having a second heterodimerization domain, wherein the second hinge-containing polypeptide is associated with a second light chain, wherein the second heterodimerization domain interacts with the first heterodimerization domain at an interface, and wherein the first and second hinge-containing polypeptides are linked by at least one interchain disulfide bond, the method comprising the steps of:

(a) culturing a first host cell capable of expressing a first hinge-containing polypeptide and a first light chain;

(b) culturing a second host cell capable of expressing a second hinge-containing polypeptide and a second light chain; and, (c) obtaining a combined culture medium for the first host cell and the second host cell, wherein the combined culture medium comprises the heteromultimeric protein, and wherein the first host cell and the second host cell are each a mammalian cell. In certain embodiments, the combined culture medium was obtained without disrupting cell membrane of the first and second host cells. In certain embodiments, the method further comprises adding a reducing agent to the combined culture medium.

Also provided are methods of preparing a heteromultimeric protein comprising i) a first hinge-containing polypeptide having a first heterodimerization domain, wherein the first hinge-containing polypeptide is associated with a first light chain, and ii) a second hinge-containing polypeptide having a second heterodimerization domain, wherein the second hinge-containing polypeptide is associated with a second light chain, wherein the second heterodimerization domain interacts with the first heterodimerization domain at an interface, and wherein the first and second hinge-containing polypeptides are linked by at least one interchain disulfide bond, the method comprising the steps of:

(a) culturing a first host cell capable of expressing a first hinge-containing polypeptide and a first light chain, wherein a first homodimer comprising two first hinge-containing polypeptides and two first light chains is secreted;

(b) culturing a second host cell capable of expressing a second hinge-containing polypeptide and a second light chain, wherein a second homodimer comprising two second hinge-containing polypeptides and two second light chains is secreted;

(c) obtaining a combined culture medium for the first host cell and the second host cell without disrupting cell membrane of the first and second host cells, wherein the combined culture medium comprises the first homodimer and the second homodimer;

(d) incubating the combined culture medium under reducing conditions sufficient to allow formation of the heteromultimeric protein, and;

(e) obtaining the heteromultimeric protein, wherein the first host cell and the second host cell are each a mammalian cell. In certain embodiments, the method further comprises adding a reducing agent to the combined culture medium. In certain embodiments according to (or as applied to) any of the embodiments above, the first hinge containing polypeptide and the second hinge containing polypeptide comprise a first and second heavy chains. In certain embodiments according to (or as applied to) any of the embodiments described herein, the first hinge containing polypeptide and first light chain comprise a first half antibody. In certain embodiments according to (or as applied to) any of the embodiments described herein, the second hinge containing polypeptide and second light chain comprise a second half antibody.

In certain embodiments according to (or as applied to) any of the embodiments above, obtaining the combined culture medium comprises: (1) harvesting a first culture medium for the first host cell culture;

(2) harvesting a second culture medium for the second host cell culture; and, (3) combining the first culture medium and the second culture medium to obtain the combined culture medium.

In certain embodiments according to (or as applied to) any of the embodiments above, obtaining the combined culture medium comprises harvesting culture medium of a combined cell culture comprising the first host cell and the host cell. In certain embodiments, the combined culture medium was obtained without disrupting cell membrane of the first and second host cells.

First and second host cells in the methods of the invention can be cultured in any setting that permits expression and isolation of the polypeptides of interest. In certain embodiments according to (or as applied to) any of the embodiments above, the first host cell and the second host cell are cultured separately before combining into the combined cell culture.

In certain embodiments according to (or as applied to) any of the embodiments above, the methods further comprise the step of culturing the combined cell culture at a temperature of about 25° C. to about 40° C. In certain embodiments according to (or as applied to) any of the embodiments above, the combined culture medium is incubated for about 24 hours to about 7 days after the combined culture medium is obtained. In certain embodiments according to (or as applied to) any of the embodiments above, the combined culture medium is incubated at about 4° C. to about 8° C. In certain embodiments according to (or as applied to) any of the embodiments above, the combined culture medium is agitated.

In certain embodiments according to (or as applied to) any of the embodiments above, the methods further comprise isolating the heteromultimeric protein from the combined culture medium. In certain embodiments according to (or as applied to) any of the embodiments above, the heteromultimeric protein is isolated using a protein A column. In certain embodiments, the heteromultimeric protein is further purified using methods known in the art.

In certain embodiments according to (or as applied to) any of the embodiments above, the methods further comprise adding a reducing agent to the first cell culture medium and/or to the second cell culture medium before or after the first and second cell culture media are harvested. In certain embodiments according to (or as applied to) any of the embodiments above, the methods further comprise adding a reducing agent to the culture medium of the combined cell culture before the culture medium of the combined cell culture is harvested. In certain embodiments according to (or as applied to) any of the embodiments above, the reducing agent is added about 4 to about 24, about 5 to about 20, about 10 to about 20, about 10 to about 15, or about 15 to about 18 hours before the harvesting step. In certain embodiments according to (or as applied to) any of the embodiments above, the reducing agent is added about 15 hours before the harvesting step.

In certain embodiments according to (or as applied to) any of the embodiments above, the methods further comprise adding a reducing agent to the combined cell culture medium. In certain embodiments according to (or as applied to) any of the embodiments above, the combined culture medium containing the reducing agent is further incubated for about 4 hours to about 7 days. In certain embodiments according to (or as applied to) any of the embodiments above, the combined culture medium containing the reducing agent is further incubated for about 15 hours. In certain embodiments according to (or as applied to) any of the embodiments above, the reducing agent is added to the combined culture medium before isolating the heteromultimeric protein from the combined culture medium. In certain embodiments according to (or as applied to) any of the embodiments above, the combined culture medium containing the reducing agent is incubated for at least about 24 hours prior to isolating the heteromultimeric protein. In certain embodiments according to (or as applied to) any of the embodiments above, the combined culture medium containing the reducing agent is incubated for at least about 48 hours prior to isolating the heteromultimeric protein. In certain embodiments according to (or as applied to) any of the embodiments above, the heteromultimeric protein is isolated using a protein A column.

In certain embodiments according to (or as applied to) any of the embodiments above, the reducing agent is selected from the group consisting of glutathione, 2-mercaptoethanol, 2-mercaptoethylamine, tris(2-carboxyethyl)phosphine (TCEP), cysteine, cysteine, dithiothreitol, cysteindithiothreitol, dithiolbutylamine, or combinations thereof. In certain embodiments according to (or as applied to) any of the embodiments above, the reducing agent is glutathione, and wherein the glutathione is added at a concentration of about 5 mM to no more than about 20 mM. In certain embodiments according to (or as applied to) any of the embodiments above, the reducing agent is glutathione, and wherein the glutathione is added at a concentration of about 2 mM to about 10 mM. In certain embodiments according to (or as applied to) any of the embodiments above, the reducing agent is glutathione, and wherein the glutathione is added at a concentration of about 5 mM to less than about 20 mM. In certain embodiments according to (or as applied to) any of the embodiments above, the reducing agent is glutathione, and wherein the glutathione is added at a concentration of about 15 mM.

In certain embodiments according to (or as applied to) any of the embodiments above, the first host cell is a stable cell line. In certain embodiments according to (or as applied to) any of the embodiments above, the second host cell is a stable cell line. In certain embodiments according to (or as applied to) any of the embodiments above, the first host cell is CHO cell. In certain embodiments according to (or as applied to) any of the embodiments above, the second host cell is CHO cell.

In certain embodiments according to (or as applied to) any of the embodiments above, the ratio of the first host cell and the second host cell is adjusted so that the molar ratio of the first hinge-containing polypeptide and the second hinge-containing polypeptide is about 1:10 to about 10:1 when the first host cell culture and the second host cell culture are combined to form a combined culture. In certain embodiments according to (or as applied to) any of the embodiments above, the molar ratio of the first hinge-containing polypeptide expressed by the first host cell and the second hinge-containing polypeptide expressed by the second host cell is 1:1 when the host cell culture and the second host cell culture are combined to form a combined culture.

In certain embodiments according to (or as applied to) any of the embodiments above, the hinge-containing polypeptides comprise an Fc region or variant thereof. In certain embodiments according to (or as applied to) any of the embodiments above, the first and/or the second hinge-containing polypeptide comprises an antibody heavy chain.

In certain embodiments according to (or as applied to) any of the embodiments above, the first heterodimerization domain comprises a knob modification at the interface and the second heterodimerization domain comprises a hole modification at the interface. In certain embodiments according to (or as applied to) any of the embodiments above, the knob modification comprises substituting an original amino acid residue from the first heterodimerization domain with an amino acid residue with a larger side chain than the original amino acid residue. In certain embodiments according to (or as applied to) any of the embodiments above, the substituting amino acid residue is selected from the group consisting of tryptophan, phenylalanine, tyrosine and arginine. In certain embodiments according to (or as applied to) any of the embodiments above, the hole modification comprises substituting an original amino acid residue from the second heterodimerization domain with an amino acid residue with a smaller side chain than the original amino acid residue. In certain embodiments according to (or as applied to) any of the embodiments above, the substituting amino acid residue is selected from the group consisting of serine, threonine, valine, and alanine. In certain embodiments according to (or as applied to) any of the embodiments above, the knob modification comprises T366W substitution (EU numbering). In certain embodiments according to (or as applied to) any of the embodiments above, the hole modification comprises two or more amino acid substitutions selected from the group consisting of T366S, L368A and Y407V (EU numbering).

In certain embodiments according to (or as applied to) any of the embodiments above, said interchain disulfide bond is between hinge regions. In certain embodiments according to (or as applied to) any of the embodiments above, the heteromultimeric protein is an antibody. In certain embodiments according to (or as applied to) any of the embodiments above, the heteromultimeric protein is a bispecific antibody. In certain embodiments according to (or as applied to) any of the embodiments above, said antibody is a humanized or human antibody. In certain embodiments according to (or as applied to) any of the embodiments above, the antibody is a full-length antibody. In certain embodiments according to (or as applied to) any of the embodiments above, the antibody is an antibody fragment comprising at least a portion of human $C_H2$ and/or $C_H3$ domain. In certain embodiments according to (or as applied to) any of the embodiments above, the antibody is selected from the group consisting of IgG, IgA and IgD. In certain embodiments according to (or as applied to) any of the embodiments above, the antibody is IgG. In certain embodiments according to (or as applied to) any of the embodiments above, the antibody is IgG1, IgG2 or IgG4. In certain embodiments according to (or as applied to) any of the embodiments above, the first light chain and the second light chain comprise different variable domain sequences.

In another aspect, provided are methods of preparing a heteromultimeric protein comprising i) a first hinge-containing polypeptide having a first heterodimerization domain, wherein the first hinge-containing polypeptide is associated with a first light chain, and ii) a second hinge-containing polypeptide having a second heterodimerization domain, wherein the second hinge-containing polypeptide is associated with a second light chain, wherein the second heterodimerization domain interacts with the first heterodimerization domain at an interface, and wherein the first and second hinge-containing polypeptides are linked by at least one interchain disulfide bond, the method comprising the steps of:

(a) culturing a combined culture of a first host cell and a second host cell, wherein the first host cell is capable of expressing the first hinge-containing polypeptide and the first light chain, wherein the second host cell is capable of expressing the second hinge-containing polypeptide and the second light chain, and wherein the first host cell and the second host cell are each a mammalian cell;

(b) adding a reducing agent to the combined culture; and
(c) harvesting a combined culture medium from the combined culture without disrupting cell membrane, wherein the combined culture medium comprises the heteromultimeric protein.

In certain embodiments, the first host cell secretes a first homodimer comprising two first hinge-containing polypeptides and two first light chains, wherein the second host cell secretes a second homodimer comprising two second hinge-containing polypeptides and two second light chains, wherein the combined culture comprises the first homodimer and the second homodimer. In certain embodiments, adding the reducing agent to the combined culture allows formation of the heteromultimeric protein.

In certain embodiments according to (or as applied to) any of the embodiments above, the reducing agent is added after the combined culture has been cultured for no more than about 18 days. In certain embodiments according to (or as applied to) any of the embodiments above, the combined culture medium is harvested 4 hour to 24 hours after the reducing agent is added. In certain embodiments according to (or as applied to) any of the embodiments above, the step of harvesting a combined culture medium comprises removing the first host cell and second host cell from the combined culture medium. In certain embodiments according to (or as applied to) any of the embodiments above, the combined culture medium is incubated for 4 hours to 7 days.

In certain embodiments, the methods further comprise the step of adjusting the cell:cell ratio of the first host cell and second host cell in a combined culture. In certain embodiments, the cell:cell ratio is adjusted so that the molar ratio of the first hinge containing polypeptide (with the associated light chain) expressed from the first host cell to the second hinge-containing polypeptide (with the associated light chain) expressed from the second host cell in a combined culture reaches a desired molar ratio. In certain embodiments, the host cell is a stable cell line. In certain embodiments, the stable cell line is stably transfected with the nucleic acid molecule (s) that is capable of expressing a hinge-containing polypeptide and a light chain.

It is to be understood that methods of the invention can include other steps which generally are routine steps evident for initiating and/or completing the process encompassed by methods of the invention as described herein. For example, in one embodiment, step (a) of a method of the invention is preceded by a step wherein a nucleic acid encoding a first hinge-containing polypeptide is introduced into a first host cell, and a nucleic acid encoding a second hinge-containing polypeptide is introduced into a second host cell. In one embodiment, methods of the invention further comprise a step of purifying heteromultimeric proteins having binding specificity to at least two distinct targets.

In certain embodiments according to (or as applied to) any of the embodiments above, the first hinge containing polypeptide and the first light chain (or its associated light chain) comprise a first binding domain for a first target. In certain embodiments according to (or as applied to) any of the embodiments above, the second hinge containing polypeptide and the second light chain (or its associated light chain) comprise a second binding domain for a second target. The first and second targets can be different epitopes located on a single molecule or located on different molecules.

In another aspect, provided is a heteromultimeric protein produced any of the methods above. In certain embodiments according to (or as applied to) any of the embodiments above, the heteromultimeric protein is a bispecific antibody. Also provided are compositions comprising a heteromultimeric protein produced any of the methods above (such as a bispecific antibody) and a pharmaceutically acceptable carrier.

Heteromultimeric proteins of the invention generally are capable of binding, preferably specifically, to antigens. Such antigens include, for example, tumor antigens, cell survival regulatory factors, cell proliferation regulatory factors, molecules associated with (e.g., known or suspected to contribute functionally to) tissue development or differentiation, cell surface molecules, lymphokines, cytokines, molecules involved in cell cycle regulation, molecules involved in vasculogenesis and molecules associated with (e.g., known or suspected to contribute functionally to) angiogenesis. An antigen to which a heteromultimeric protein of the invention is capable of binding may be a member of a subset of one of the above-mentioned categories, wherein the other subset(s) of said category comprise other molecules/antigens that have a distinct characteristic (with respect to the antigen of interest). An antigen of interest may also be deemed to belong to two or more categories. In one embodiment, the invention provides a heteromultimeric protein that binds, preferably specifically, a tumor antigen that is not a cell surface molecule. In one embodiment, a tumor antigen is a cell surface molecule, such as a receptor polypeptide. In another example, in some embodiments, a heteromultimeric protein of the invention binds, preferably specifically, a tumor antigen that is not a cluster differentiation factor. In another example, a heteromultimeric protein of the invention is capable of binding, preferably specifically, to a cluster differentiation factor, which in some embodiments is not, for example, CD3 or CD4. In some embodiments, a heteromultimeric protein of the invention is an anti-VEGF antibody. In some embodiments, a heteromultimeric protein of the invention is a bispecific antibody selected from the group consisting of IL-1alpha/IL-1beta, IL-12/IL-18; IL-13/IL-9; IL-13/IL-4; IL-13/IL-5; IL-5/IL-4; IL-13/IL-1beta; IL-13/IL-25; IL-13/TARC; IL-13/MDC; IL-13/MEF; IL-13/TGF-β; IL-13/LHR agonist; IL-12/TWEAK, IL-13/CL25; IL-13/SPRR2a; IL-13/SPRR2b; IL-13/ADAM8, IL-13/PED2, IL17A/IL17F, CD3/CD19, CD138/CD20; CD138/CD40; CD19/CD20; CD20/CD3; CD38/CD138; CD38/CD20; CD38/CD40; CD40/CD20; CD-8/IL-6; CD20/BR3, TNFalpha/TGF-beta, TNFalpha/IL-1beta; TNFalpha/IL-2, TNF alpha/IL-3, TNFalpha/IL-4, TNFalpha/IL-5, TNFalpha/IL6, TNFalpha/IL8, TNFalpha/IL-9, TNFalpha/IL-10, TNFalpha/IL-11, TNFalpha/IL-12, TNFalpha/IL-13, TNFalpha/IL-14, TNFalpha/IL-15, TNFalpha/IL-16, TNFalpha/IL-17, TNFalpha/IL-18, TNFalpha/IL-19, TNFalpha/IL-20, TNFalpha/IL-23, TNFalpha/IFNalpha, TNFalpha/CD4, TNFalpha/VEGF, TNFalpha/MIF, TNFalpha/ICAM-1, TNFalpha/PGE4, TNFalpha/PEG2, TNFalpha/RANK ligand, TNFalpha/Te38; TNFalpha/BAFF; TNFalpha/CD22; TNFalpha/CTLA-4; TNFalpha/GP130; TNFα/IL-12p40; VEGF/HER2, VEGF-A/HER2, VEGF-A/PDGF, HER1/HER2, VEGF-A/VEGF-C, VEGF-C/VEGF-D, HER2/DR5, VEGF/IL-8, VEGF/MET, VEGFR/MET receptor, VEGFR/EGFR, HER2/CD64, HER2/CD3, HER2/CD16, HER2/HER3; EGFR/HER2, EGFR/HER3, EGFR/HER4, IL-13/CD40L, IL4/CD40L, TNFR1/IL-1R, TNFR1/IL-6R, TNFR1/IL-18R, EpCAM/CD3, MAPG/CD28, EGFR/CD64, CSPGs/RGM A; CTLA-4/BTNO2; IGF1/IGF2; IGF1/2/Erb2B; MAG/RGM A; NgR/RGM A; NogoA/RGM A; OMGp/RGM A; PDL-I/CTLA-4; and RGM A/RGM B, IL1β/IL18, NRP1/VEGFA, VEGFA/NRP2, cMET/EGFR, ALK1/BMP9, VEGFA/α5β1, HER1/HER3-BU, and CMV. In some embodiments, a heteromultimeric protein of the invention binds to at least two target molecules selected from the group consisting of: α5β1, ALK1, BMP9, IL-1alpha, IL-1beta, TARC, MDC, MEF, TGF-β, LHR agonist, TWEAK, CL25, SPRR2a, SPRR2b, ADAMS, PED2, CD3, CD4, CD16, CD19, CD20, CD22, CD28, CD40, CD38, CD64, CD138, CD-8, BR3, TNFalpha, TGF-beta, IL-2, IL-3, IL-4, IL-5, IL-6, IL-8, IL-9, IL-10, IL-11, IL-12, IL-13, IL-14, IL-15, IL-16, IL-17, IL-17A, IL-17F, IL-18, IL-19, IL-20, IL-23, IL-25, IFNalpha, MIF, ICAM-1, PGE4, PEG2, RANK ligand, Te38, BAFF, CTLA-4, GP130, IL-12p40, VEGF, VEGF-A, PDGF, HER1, HER2, HER3, HER3-BU, HER4, VEGF-C, VEGF-D, DR5, cMET, MET, MET receptor, VEGFR, EGFR, CD40L, TNFR1, IL-1R, IL-6R, IL-18R, EpCAM, MAPG, CSPGs, BTNO2, IGF1, IGF2, IGF1/2, Erb2B, MAG, NgR, NogoA, NRP1, NRP2, OMGp, PDL-I, RGM A and RGM B. In some embodiments, a heteromultimeric protein of this invention binds to CD3 and at least one additional target molecule selected from BLR1, BR3, CD19, CD20, CD22, CD72, CD79A, CD79B, CD180 (RP105), CR2, FcRH1, FcRH2, FcRH5, FCER2, FCRL4, HLA-DOB, and NAG14.

Heteromultimeric proteins may be modified to enhance and/or add additional desired characteristics. Such characteristics include biological functions such as immune effector functions, a desirable in vivo half-life/clearance, bioavailability, biodistribution or other pharmacokinetic characteristics. Such modifications are well known in the art and can also be determined empirically, and may include modifications by moieties that may or may not be peptide-based. For example, antibodies may be glycosylated or aglycosylated, generally depending at least in part on the nature of the host cell. Preferably, antibodies of the invention are aglycosylated. An aglycosylated antibody produced by a method of the invention can subsequently be glycosylated by, for example, using in vitro glycosylation methods well known in the art. As described above and herein, heteromultimeric proteins of the invention can be produced in a prokaryotic cell, such as, for example, E. coli. E. coli-produced heteromultimeric proteins are generally aglycosylated and lack the biological functions normally associated with glycosylation profiles found in mammalian host cell (e.g., CHO) produced heteromultimeric proteins.

The invention also provides immunoconjugates comprising a heteromultimeric protein of the invention conjugated with a heterologous moiety. Any heterologous moiety would be suitable so long as its conjugation to the antibody does not substantially reduce a desired function and/or characteristic of the antibody. For example, in some embodiments, an immunoconjugate comprises a heterologous moiety which is a cytotoxic agent. In some embodiments, said cytotoxic agent is selected from the group consisting of a radioactive isotope, a chemotherapeutic agent and a toxin. In some embodiments, said toxin is selected from the group consisting of calichemicin, maytansine and trichothene. In some embodiments, an immunoconjugate comprises a heterologous moiety which is a detectable marker. In some embodiments, said detectable marker is selected from the group consisting of a radioactive isotope, a member of a ligand-receptor pair, a member of an enzyme-substrate pair and a member of a fluorescence resonance energy transfer pair.

In another aspect, provided are host cells comprising a polynucleotide or recombinant vector encoding a first hinge-containing polypeptide of the heteromultimeric protein described above, wherein the host cell does not express a second hinge-containing polypeptide of the heteromultimeric protein. In certain embodiments according to (or as applied to) any of the embodiments above, the hinge-containing polypeptide is an antibody heavy chain. In certain embodiments according to (or as applied to) any of the embodiments above, the hinge-containing polypeptide is paired with an antibody light chain. In certain embodiments according to (or as applied to) any of the embodiments above, the host cell is a stable cell line. In certain embodiments according to (or as applied to) any of the embodiments above, the host cell is a mammalian cell. In certain embodiments according to (or as applied to) any of the embodiments above, the host cell is a CHO cell.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

All references cited herein are incorporated by reference in their entirety.

BRIEF DESCRIPTION OF THE DRAWINGS

FIG. 5, panel B shows the chromatogram of samples separated based on hydrophobicity for anti-Target H.

FIG. 7B shows an enlargement of the m/z range of the bispecific antibody peak.

ABBREVIATIONS

Figure 1B:
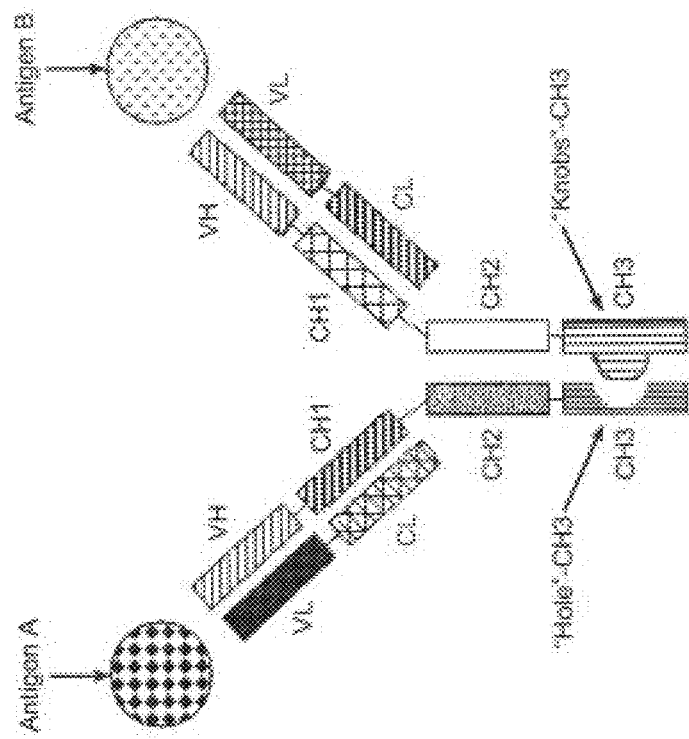
FIG. 1B illustrates a full-length bispecific antibody. Not depicted are the inter-heavy chain disulfide bonds in the hinge region.

ADCC=Antibody-dependent cell-mediated cytotoxicity
API=Anti-pathogen immunoadhesins
BPI=Bactericidal/permeability-increasing protein C1q=Complement factor 1 q
CD=Cluster of Differentiation
CDC=Complement-dependent cytotoxicity
CH1 or $C_H1$=Heavy chain first constant domain
CH2 or $C_H2$=Heavy chain second constant domain
CH3 or $C_H3$=Heavy chain third constant domain
CH4 or $C_H4$=Heavy chain fourth constant domain
CL or $C_L$=Light chain constant domain
CTLA=Cytotoxic T lymphocyte-associated molecule
Fc=Fragment crystallizable
Fc(R=Receptor gamma for the Fc portion of IgG
HIV=Human immunodeficiency virus
ICAM=Intercellular adhesion molecule
BsAb=Bispecific antibody
BsDb=Bispecific diabody
dsFv=Disulfide-stabilized Fv
Fc=Constant fragment of an antibody
Fd=$V_H$+$C_H1$ of an antibody
FcR=Fc receptor
Fv=Variable fragment of an antibody
IgG=Immunoglobulin G
mAb=Monoclonal antibody
PBL=Peripheral blood lymphocyte
scDb=Single-chain diabody
scFv=Single-chain Fv
$(scFv)_2$=scFv-scFv tandem
Tandab=Tandem diabody
VH or $V_H$=Variable domain of the heavy chain of an antibody
VL or $V_L$=Variable domain of the light chain of an antibody

DETAILED DESCRIPTION

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

I. Definitions

A "heteromultimer", "heteromultimeric complex", or "heteromultimeric protein" refers to a molecule comprising a first hinge-containing polypeptide having a first heterodimerization domain, wherein the first hinge-containing polypeptide is associated with a first light chain, and a second hinge-containing polypeptide having a second heterodimerization domain, wherein the second hinge-containing polypeptide is associated with a second light chain, wherein the second heterodimerization domain interacts with the first heterodimerization domain at an interface, and wherein the first and second hinge-containing polypeptides are linked by at least one interchain disulfide bond. The heteromultimer can comprise a "heterodimer" formed by the first hinge-containing polypeptide, the first light chain, the second hinge-containing polypeptide, and the second light chain. Alternatively, the heteromultimer can form, e.g., a bispecific antibody. The polypeptides of the heteromultimer may interact with each other by a non-peptidic, covalent bond (e.g., disulfide bond) and/or a non-covalent interaction (e.g., hydrogen bonds, ionic bonds, van der Waals forces, and/or hydrophobic interactions).

As used herein, "heteromultimerization domain" refers to alterations or additions to a biological molecule so as to promote heteromultimer formation and hinder homomultimer formation. Any heterodimerization domain having a strong preference for forming heterodimers over homodimers is within the scope of the invention. Illustrative examples include but are not limited to, for example, US Patent Application 20030078385 (Arathoon et al.—Genentech; describing knob into holes); WO2007147901 (Kjærgaard et al.—Novo Nordisk: describing ionic interactions); WO 2009089004 (Kannan et al.—Amgen: describing electrostatic steering effects); WO2011/034605 (Christensen et al.—Genentech; describing coiled coils). See also, for example, Pack, P. & Plueckthun, A., Biochemistry 31, 1579-1584 (1992) describing leucine zipper or Pack et al., Bio/Technology 11, 1271-1277 (1993) describing the helix-turn-helix motif. The phrase "heteromultimerization domain" and "heterodimerization domain" are used interchangeably herein.

The phrase "hinge-containing polypeptide" as used herein refers to a polypeptide that comprises a region corresponding to the hinge region of an immunoglobulin as understood in the art, e.g., the region between the $C_H1$ and $C_H2$ domains of the heavy chain. The "hinge region," "hinge sequence", and variations thereof, as used herein, includes the meaning known in the art, which is illustrated in, for example, Janeway's Immunobiology, (Garland Science, Taylor & Francis Group, LLC, NY) (7th ed., 2008); Bloom et al., Protein Science (1997), 6:407-415; Humphreys et al., J. Immunol. Methods (1997), 209:193-202. See also, for example, Burton, Molec. Immunol. 22:161-206 (1985) and Papadea, C. and I. J. Check (1989) "Human immunoglobulin G and immunoglobulin G subclasses: biochemical, genetic, and clinical aspects." Crit Rev Clin Lab Sci 27(1): 27-58. It will be appreciated by one skilled in the art that the number of amino acids as well as the number of cysteine residues available for interchain disulfide bond formation varies between the classes and isotypes of immunoglobulins.

All such hinge regions may be in the hinge-containing polypeptides and are within the scope of the invention. In certain embodiments, the first hinge-containing polypeptide comprises a first antibody heavy chain. In certain embodiments, the first heavy chain associates with a first light chain to form a first half antibody. The term "antibody" herein is used in the broadest sense and refers to any immunoglobulin (Ig) molecule comprising two heavy chains and two light chains, and any fragment, mutant, variant or derivation thereof so long as they exhibit the desired biological activity (e.g., epitope binding activity). Examples of antibodies include monoclonal antibodies, polyclonal antibodies, multispecific antibodies (e.g., bispecific antibodies) and antibody fragments as described herein. An antibody can be human, humanized and/or affinity matured.

As a frame of reference, as used herein an antibody will refer to the structure of an immunoglobulin G (IgG). However, one skilled in the art would understand/recognize that an antibody of any immunoglobulin class may be utilized in the inventive method described herein. For clarity, an IgG molecule contains a pair of identical heavy chains (HCs) and a pair of identical light chains (LCs). Each LC has one variable domain ($V_L$) and one constant domain ($C_L$), while each HC has one variable ($V_H$) and three constant domains ($C_H1$, $C_H2$, and $C_H3$). The $C_H1$ and $C_H2$ domains are connected by a hinge region. This structure is well known in the art. Reference is made to FIG. 1B.

Figure 1A:
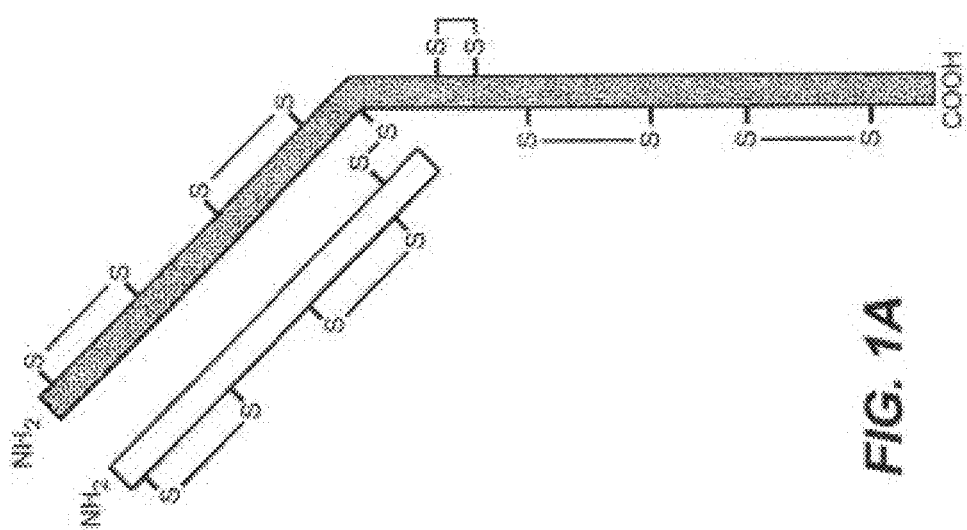
FIG. 1A illustrates a fully oxidized half-antibody. Not shown are the "knob" or "hole" or other heterodimerization domains. The half-antibody depicted in this figure is an IgG1 isotype. One skilled in the art will appreciate that the other immunoglobulin isotypes can be envisioned as half-antibodies with the corresponding inter- and intra-chain bonds. In an intact Ab the hinge cysteines will form inter-chain disulfide bonds.

As used herein, "half-antibody" refers to one immunoglobulin heavy chain associated with one immunoglobulin light chain. An exemplary half-antibody is depicted in FIG. 1A. One skilled in the art will readily appreciate that a half-antibody may also have an antigen binding domain consisting of a single variable domain.

Figure 2:
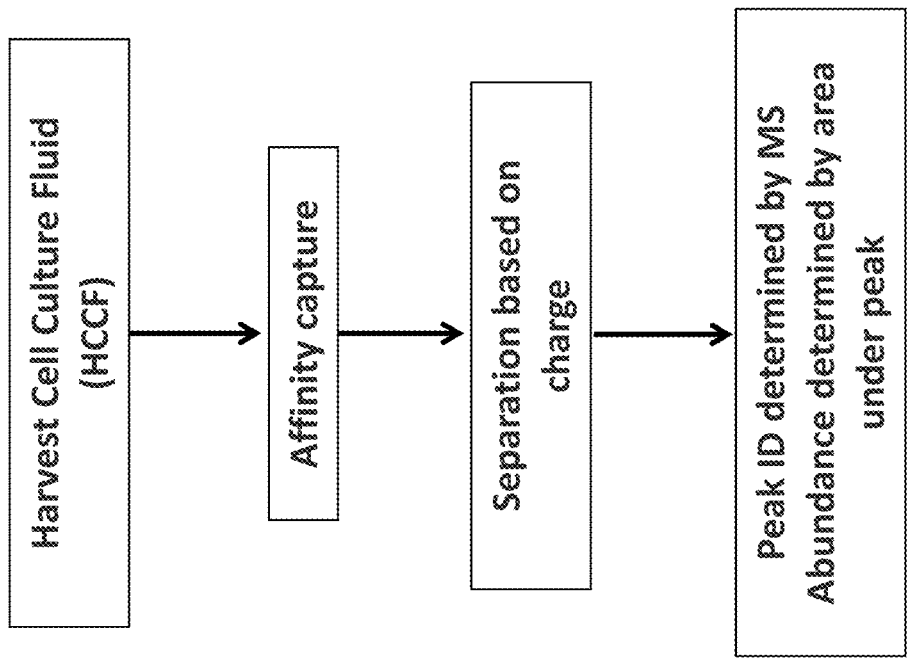
FIG. 2 shows flow diagrams for two assays that can be used to determine % half antibody and % covalent bispecific antibody
Figure 2:
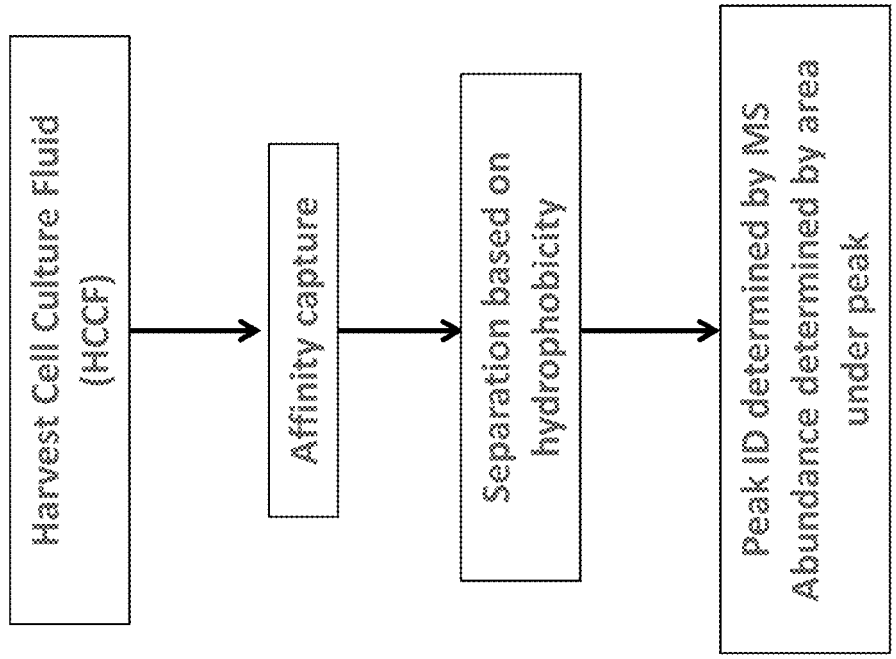

The term "maxibody" refers to a fusion protein comprising a scFv fused to an Fc polypeptide. Reference is made to FIG. 8a of WO 2009089004. Reference is made to FIG. 2 of WO 2009089004 for a bispecific maxibody.

The term "$C_H2$ domain" of a human IgG Fc region usually extends from about residues 231 to about 340 of the IgG according to the EU numbering system. The $C_H2$ domain is unique in that it is not closely paired with another domain. Rather, two N-linked branched carbohydrate chains are interposed between the two $C_H2$ domains of an intact native IgG molecule. It has been speculated that the carbohydrate may provide a substitute for the domain-domain pairing and help stabilize the $C_H2$ domain. Burton, Molec. Immunol. 22:161-206 (1985).

The term "$C_H3$ domain" comprises the stretch of residues C-terminal to a $C_H2$ domain in an Fc region (i.e., from about amino acid residue 341 to about amino acid residue 447 of an IgG according to the EU numbering system).

The term "Fc region", as used herein, generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain might vary, the human IgG heavy chain Fc sequence is usually defined to stretch from an amino acid residue at about position Cys226, or from about position Pro230, to the carboxyl terminus of the Fc sequence. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. The Fc sequence of an immunoglobulin generally comprises two constant domains, a $C_H2$ domain and a $C_H3$ domain, and optionally comprises a $C_H4$ domain. By "Fc polypeptide" herein is meant one of the polypeptides that make up an Fc region, e.g., a monomeric Fc. An Fc polypeptide may be obtained from any suitable immunoglobulin, such as $IgG_1$, $IgG_2$, $IgG_3$, or $IgG_4$ subtypes, IgA, IgE, IgD or IgM. The Fc region comprises the carboxy-terminal portions of both H chains held together by disulfides. The effector functions of antibodies are determined by sequences in the Fc region; this region is also the part recognized by Fc receptors (FcR) found on certain types of cells. In some embodiments, an Fc polypeptide comprises part or all of a wild type hinge sequence (generally at its N terminus). In some embodiments, an Fc polypeptide does not comprise a functional or wild type hinge sequence.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g., B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human $IgG_1$ Fc region (non-A and A allotypes); native sequence human $IgG_2$ Fc region; native sequence human $IgG_3$ Fc region; and native sequence human $IgG_4$ Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95%, at least about 96%, at least about 97%, at least about 98% or at least about 99% homology therewith.

"Fc component" as used herein refers to a hinge region, a $C_H2$ domain or a $C_H3$ domain of an Fc region.

In certain embodiments, the hinge-containing polypeptide comprises an IgG Fc region, preferably derived from a wild-type human IgG Fc region. By "wild-type" human IgG Fc it is meant a sequence of amino acids that occurs naturally within the human population. Of course, just as the Fc sequence may vary slightly between individuals, one or more alterations may be made to a wildtype sequence and still remain within the scope of the invention. For example, the Fc region may contain additional alterations that are not related to the present invention, such as a mutation in a glycosylation site or inclusion of an unnatural amino acid.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., *J. Immunol.* 150:880-887 (1993); Clarkson et al., *Nature* 352: 624-628 (1991).

The term "Fab" as used herein refers to an antigen-binding fragment of an antibody. As noted above, papain may be used to digest an intact antibody. Papain digestion of antibodies produces two identical antigen-binding fragments, i.e., "Fab" fragments, and a residual "Fc" fragment (i.e., the Fc region, supra). The Fab fragment consists of an entire L chain along with the variable region domain of the H chain ($V_H$), and the first constant domain of one heavy chain ($C_H1$).

The phrase "antigen binding arm", "target molecule binding arm", "target binding arm" and variations thereof, as used herein, refers to a component part of a heteromultimeric protein of the invention that has an ability to specifically bind a target of interest. Generally and preferably, the antigen binding arm is a complex of immunoglobulin polypeptide sequences, e.g., CDR and/or variable domain sequences of an immunoglobulin light and heavy chain.

A "target" or "target molecule" refers to a moiety recognized by a binding arm of the heteromultimeric protein. For example, if the heteromultimeric protein is an antibody, then the target may be epitopes on a single molecule or on different molecules, or a pathogen or a tumor cell, depending on the context. Similarly, if the heteromultimeric protein is a receptor-Fc fusion protein the target would be the cognate binding partner for the receptor. One skilled in the art will appreciate that the target is determined by the binding specificity of the target binding arm and that different target binding arms may recognize different targets. A target preferably binds to a heteromultimeric protein of this invention with affinity higher than 1 uM Kd (according to scatchard analysis). Examples of target molecules include, but are not limited to, serum soluble proteins and/or their receptors, such as cytokines and/or cytokine receptors, adhesins, growth factors and/or their receptors, hormones, viral particles (e.g., RSV F protein, CMV, StaphA, influenza, hepatitis C virus), micoorganisms (e.g., bacterial cell proteins, fungal cells), adhesins, CD proteins and their receptors.

One example of an "intact" or "full-length" antibody is one that comprises an antigen-binding arm as well as a $C_L$ and at least heavy chain constant domains, $C_H1$, $C_H2$, and $C_H3$. The constant domains can be native sequence constant domains (e.g., human native sequence constant domains) or amino acid sequence variants thereof.

The term "coupling" as used herein refers to the steps necessary to link the first and second hinge-containing polypeptides to each other, e.g., formation of a covalent bond. Such steps comprise the reducing, annealing and/or oxidizing of cysteine residues in the first and second hinge-containing polypeptides to form an inter-chain disulfide bond. The coupling may be achieved by chemical cross-linking or the use of a redox system. See, e.g., Humphreys et al., *J. Immunol. Methods* (1998) 217:1-10 and Zhu et al., *Cancer Lett.*, (1994) 86: 127-134.

The term "multispecific antibody" is used in the broadest sense and specifically covers an antibody that has polyepitopic specificity. Such multispecific antibodies include, but are not limited to, an antibody comprising a heavy chain variable domain ($V_H$) and a light chain variable domain ($V_L$), wherein the $V_HV_L$ unit has polyepitopic specificity, antibodies having two or more $V_L$ and $V_H$ domains with each $V_HV_L$ unit binding to a different epitope, antibodies having two or more single variable domains with each single variable domain binding to a different epitope, full length antibodies, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Monospecific" refers to the ability to bind only one epitope. According to one embodiment the multispecific antibody is an IgG antibody that binds to each epitope with an affinity of 5 µM to 0.001 pM, 3 µM to 0.001 pM, 1 µM to 0.001 pM, 0.5 µM to 0.001 pM, or 0.1 µM to 0.001 pM. An illustrative drawing of a bispecific is provided in FIG. 1B.

"Antibody fragments" comprise a portion of an intact antibody, preferably the antigen binding or a variable region of the intact antibody. Examples of antibody fragments include Fab, Fab', F(ab')$_2$, and Fv fragments; diabodies (Db); tandem diabodies (taDb); linear antibodies (e.g., U.S. Pat. No. 5,641,870; Zapata et al., Protein Eng. 8(10):1057-1062 (1995)); one-armed antibodies, single variable domain antibodies, minibodies, single-chain antibody molecules; and multispecific antibodies formed from antibody fragments (e.g., including but not limited to, Db-Fc, taDb-Fc, taDb-$C_H3$ and (scFV)4-Fc).

The expression "single domain antibodies" (sdAbs) or "single variable domain (SVD) antibodies" generally refers to antibodies in which a single variable domain ($V_H$ or $V_L$) can confer antigen binding. In other words, the single variable domain does not need to interact with another variable domain in order to recognize the target antigen. Single domain antibodies consist of a single monomeric variable antibody domain ($V_H$ or $V_L$) on each antigen binding arm. Examples of single domain antibodies include those derived from camelids (llamas and camels) and cartilaginous fish (e.g., nurse sharks) and those derived from recombinant methods from humans and mouse antibodies (Ward et al., Nature (1989) 341:544-546; Dooley and Flajnik, Dev Comp Immunol (2006) 30:43-56; Muyldermans et al., Trend Biochem Sci (2001) 26:230-235; Holt et al., Trends Biotechnol (2003):21:484-490; WO 2005/035572; WO 03/035694; Davies and Riechmann, Febs Lett (1994) 339:285-290; WO00/29004; WO 02/051870). A single variable domain antibody can be present in an antigen binding arm (e.g., homo- or hetero-multimer) with other variable regions or variable domains, in which case it is not a single domain antibody.

The expression "linear antibodies" generally refers to the antibodies described in Zapata et al., Protein Eng. 8(10): 1057-1062 (1995). Briefly, these antibodies comprise a pair of tandem Fd segments ($V_H$—$C_H1$-$V_H$—$C_H1$) which, together with complementary light chain polypeptides, form a pair of antigen binding regions. Linear antibodies can be bispecific or monospecific.

The term "knob-into-hole" or "KnH" technology as mentioned herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, $C_L$:$C_H1$ interfaces or $V_H/V_L$ interfaces of antibodies (e.g., US2007/0178552, WO 96/027011, WO 98/050431 and Zhu et al. (1997) Protein Science 6:781-788). This is especially useful in driving the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions).

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains, which enables the sFv to form the desired structure for antigen binding. For a review of sFv, see Pluckthun, The Pharmacology of Monoclonal Antibodies, vol. 113, Rosenburg and Moore eds., Springer-Verlag, New York, pp. 269-315 (1994); Malmborg et al., J. Immunol. Methods 183:7-13, 1995.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA 90:6444-6448 (1993).

The term "one-armed antibody" or "one-armed antibodies" refers to an antibody that comprises (1) a variable domain joined by a peptide bond to polypeptide comprising a $C_H2$ domain, a $C_H3$ domain or a $C_H2$-$C_H3$ domain and (2) a second $C_H2$, $C_H3$ or $C_H2$-$C_H3$ domain, wherein a variable domain is not joined by a peptide bond to a polypeptide comprising the second $C_H2$, $C_H3$ or $C_H2$-$C_H3$ domain. In one embodiment, the one-armed antibody comprises 3 polypeptides (1) a first polypeptide comprising a variable domain (e.g., $V_H$), $C_H1$, $C_H2$ and $C_H3$, (2) a second polypeptide comprising a variable domain (e.g., $V_L$) and a $C_L$ domain, and (3) a third polypeptide comprising a $C_H2$ and $C_H3$ domain. In another embodiment, the one-armed antibody has a partial hinge region containing the two cysteine residues which form disulphide bonds linking the constant heavy chains. In one embodiment, the variable domains of the one armed antibody form an antigen binding region. In another embodiment, the variable domains of the one armed antibody are single variable domains, wherein each single variable domain is an antigen binding region. In an embodiment, the one-armed antibody is a single variable domain antibody.

Antibodies of the invention can be "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, provided that they exhibit the desired biological activity (U.S. Pat. No. 4,816,567; and Morrison et al., Proc. Natl. Acad. Sci. USA 81:6851-6855 (1984)). Chimeric antibodies of interest herein include primatized antibodies comprising variable domain antigen-binding sequences derived from a non-human primate (e.g., Old World Monkey, Ape, etc.) and human constant region sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

"Peptibody" or "peptibodies" refers to a fusion of randomly generated peptides with an Fc domain. See U.S. Pat. No. 6,660,843, issued Dec. 9, 2003 to Feige et al. (incorporated by reference in its entirety). They include one or more peptides linked to the N-terminus, C-terminus, amino acid sidechains, or to more than one of these sites. Peptibody technology enables design of therapeutic agents that incorporate peptides that target one or more ligands or receptors, tumor-homing peptides, membrane-transporting peptides, and the like. Peptibody technology has proven useful in design of a number of such molecules, including linear and disulfide-constrained peptides, "tandem peptide multimers" (i.e., more than one peptide on a single chain of an Fc domain). See, for example, U.S. Pat. No. 6,660,843; U.S. Pat. App. No. 2003/0195156, published Oct. 16, 2003 (corresponding to WO 02/092620, published Nov. 21, 2002); U.S. Pat. App. No. 2003/0176352, published Sep. 18, 2003 (corresponding to WO 03/031589, published Apr. 17, 2003); U.S. Pat. No. 6,835,809 (corresponding to WO 00/24770, published May 4, 2000); U.S. Pat. App. No. 2003/0229023, published Dec. 11, 2003; WO 03/057134, published Jul. 17, 2003; U.S. Pat. App. No. 2003/0236193, published Dec. 25, 2003 (corresponding to PCT/US04/010989, filed Apr. 8, 2004); U.S. Pat. No. 6,919,426, filed Sep. 18, 2003 (corresponding to WO 04/026329, published Apr. 1, 2004), each of which is hereby incorporated by reference in its entirety.

"Affibodies" or "Affibody" refers to the use of a protein liked by peptide bond to an Fc region, wherein the protein is used as a scaffold to provide a binding surface for a target molecule. The protein is often a naturally occurring protein such as staphylococcal protein A or IgG-binding B domain, or the Z protein derived therefrom (see Nilsson et al (1987), Prot Eng 1, 107-133, and U.S. Pat. No. 5,143,844) or a fragment or derivative thereof. For example, affibodies can be created from Z proteins variants having altered binding affinity to target molecule(s), wherein a segment of the Z protein has been mutated by random mutagenesis to create a library of variants capable of binding a target molecule. Examples of affibodies include U.S. Pat. No. 6,534,628, Nord K et al, Prot Eng 8:601-608 (1995) and Nord K et al, Nat Biotech 15:772-777 (1997). Biotechnol Appl Biochem. 2008 June; 50(Pt 2):97-112.

As used herein, the term "immunoadhesin" designates molecules which combine the binding specificity of a heterologous protein (an "adhesin") with the effector functions of immunoglobulin constant domains. Structurally, the immunoadhesins comprise a fusion of an amino acid sequence with a desired binding specificity, which amino acid sequence is other than the antigen recognition and binding site of an antibody (i.e., is "heterologous" compared to a constant region of an antibody), and an immunoglobulin constant domain sequence (e.g., $C_H2$ and/or $C_H3$ sequence of an IgG). Exemplary adhesin sequences include contiguous amino acid sequences that comprise a portion of a receptor or a ligand that binds to a protein of interest. Adhesin sequences can also be sequences that bind a protein of interest, but are not receptor or ligand sequences (e.g., adhesin sequences in peptibodies). Such polypeptide sequences can be selected or identified by various methods, include phage display techniques and high throughput sorting methods. The immunoglobulin constant domain sequence in the immunoadhesin can be obtained from any immunoglobulin, such as IgG1, IgG2, IgG3, or IgG4 subtypes, IgA (including IgA1 and IgA2), IgE, IgD, or IgM.

"Complex" or "complexed" as used herein refers to the association of two or more molecules that interact with each other through bonds and/or forces (e.g., van der waals, hydrophobic, hydrophilic forces) that are not peptide bonds. In one embodiment, the complex is heteromultimeric. It should be understood that the term "protein complex" or "polypeptide complex" as used herein includes complexes that have a non-protein entity conjugated to a protein in the protein complex (e.g., including, but not limited to, chemical molecules such as a toxin or a detection agent).

A heteromultimeric protein of this invention "which binds an antigen of interest is one that binds the target with sufficient affinity such that the heteromultimeric protein is useful as a diagnostic and/or therapeutic agent in targeting a protein or a cell or tissue expressing the target, and does not significantly cross-react with other proteins. In such embodiments, the extent of binding of the heteromultimeric protein to a "non-target" protein will be less than about 10% of the binding of the antibody to its particular target protein as determined by fluorescence activated cell sorting (FACS) analysis or radioimmunoprecipitation (RIA) or ELISA. With regard to the binding of a heteromultimeric protein to a target molecule, the term "specific binding" or "specifically binds to" or is "specific for" a particular polypeptide or an epitope on a particular polypeptide target means binding that is measurably different from a non-specific interaction (e.g., a non-specific interaction may be binding to bovine serum albumin or casein). Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In one embodiment, the term "specific binding" refers to binding where a heteromultimeric protein binds to a particular polypeptide or epitope on a particular polypeptide without substantially binding to any other polypeptide or polypeptide epitope.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

In one embodiment, the "Kd" or "Kd value according to this invention is measured by using surface plasmon resonance assays using a BIAcore™-2000 or a BIAcore™-3000 (BIAcore, Inc., Piscataway, N.J.) at 25° C. with immobilized target (e.g., antigen) CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen et al., J. Mol. Biol.

293:865-881 (1999). If the on-rate exceeds $10^6$ M$^{-1}$ S$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

"Biologically active" and "biological activity" and "biological characteristics" with respect to a heteromultimeric protein of this invention, such as an antibody, fragment, or derivative thereof, means having the ability to bind to a biological molecule, except where specified otherwise.

"Isolated," when used to describe the various heteromultimer polypeptides means a heteromultimer which has been separated and/or recovered from a cell or cell culture from which it was expressed. Contaminant components of its natural environment are materials which would interfere with diagnostic or therapeutic uses for the heteromultimer, and may include enzymes, hormones, and other proteinaceous or nonproteinaceous solutes. In certain embodiments, the heteromultimer will be purified (1) to greater than 95% by weight of protein as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Ordinarily, however, isolated polypeptide will be prepared by at least one purification step.

The heteromultimers of the present invention are generally purified to substantial homogeneity. The phrases "substantially homogeneous", "substantially homogeneous form" and "substantial homogeneity" are used to indicate that the product is substantially devoid of by-products originated from undesired polypeptide combinations (e.g., homomultimers).

Expressed in terms of purity, substantial homogeneity means that the amount of by-products does not exceed 10%, 9%, 8%, 7%, 6%, 4%, 3%, 2% or 1% by weight or is less than 1% by weight. In one embodiment, the by-product is below 5%.

"Biological molecule" refers to a nucleic acid, a protein, a carbohydrate, a lipid, and combinations thereof. In one embodiment, the biologic molecule exists in nature.

By "linked" or "links as used herein is meant either a direct peptide bond linkage between a first and second amino acid sequence or a linkage that involves a third amino acid sequence that is peptide bonded to and between the first and second amino acid sequences. For example, a linker peptide bonded to the C-terminal end of one amino acid sequence and to the N-terminal end of the other amino acid sequence.

By "linker" as used herein is meant an amino acid sequence of two or more amino acids in length. The linker can consist of neutral polar or nonpolar amino acids. A linker can be, for example, 2 to 100 amino acids in length, such as between 2 and 50 amino acids in length, for example, 3, 5, 10, 15, 20, 25, 30, 35, 40, 45, or 50 amino acids in length. A linker can be "cleavable," for example, by auto-cleavage, or enzymatic or chemical cleavage. Cleavage sites in amino acid sequences and enzymes and chemicals that cleave at such sites are well known in the art and are also described herein.

By a "tether" as used herein is meant an amino acid linker that joins two other amino acid sequences. A tether as described herein can link the N-terminus of an immunoglobulin heavy chain variable domain with the C-terminus of an immunoglobulin light chain constant domain. In particular embodiments, a tether is between about 15 and 50 amino acids in length, for example, between 20 and 26 amino acids in length (e.g., 20, 21, 22, 23, 24, 25, or 26 amino acids in length). A tether may be "cleavable," for example, by auto-cleavage, or enzymatic or chemical cleavage using methods and reagents standard in the art.

Enzymatic cleavage of a "linker" or a "tether" may involve the use of an endopeptidase such as, for example, Lys-C, Asp-N, Arg-C, V8, Glu-C, chymotrypsin, trypsin, pepsin, papain, thrombin, Genenase, Factor Xa, TEV (tobacco etch virus cysteine protease), Enterokinase, HRV C3 (human rhinovirus C3 protease), Kininogenase, as well as subtilisin-like proprotein convertases (e.g., Furin (PC1), PC2, or PC3) or N-arginine dibasic convertase. Chemical cleavage may involve use of, for example, hydroxylamine, N-chlorosuccinimide, N-bromosuccinimide, or cyanogen bromide.

A "Lys-C endopeptidase cleavage site" as used herein is a Lysine residue in an amino acid sequence that can be cleaved at the C-terminal side by Lys-C endopeptidase. Lys-C endopeptidase cleaves at the C-terminal side of a Lysine residue.

By a "chaotropic agent" is meant a water-soluble substance which disrupts the three-dimensional structure of a protein (e.g., an antibody) by interfering with stabilizing intra-molecular interactions (e.g., hydrogen bonds, van der Waals forces, or hydrophobic effects). Exemplary chaotropic agents include, but are not limited to, urea, Guanidine-HCl, lithium perchlorate, Histidine, and Arginine.

By a "mild detergent" is meant a water-soluble substance which disrupts the three-dimensional structure of a protein (e.g., an antibody) by interfering with stabilizing intra-molecular interactions (e.g., hydrogen bonds, van der Waals forces, or hydrophobic effects), but which does not permanently disrupt the protein structure as to cause a loss of biological activity (i.e., does not denature the protein). Exemplary mild detergents include, but are not limited to, Tween (e.g., Tween-20), Triton (e.g., Triton X-100), NP-40 (nonyl phenoxylpolyethoxylethanol), Nonidet P-40 (octyl phenoxylpolyethoxylethanol), and Sodium Dodecyl Sulfate (SDS).

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxic agents. The antibodies "arm" the cytotoxic cells and are absolutely required for such killing. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. No. 5,500,362 or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al., Proc. Natl. Acad. Sci. USA 95:652-656 (1998).

"Fc receptor" or "FcR" describes a receptor that binds to the Fc region of an antibody. The preferred FcR is a human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. Daëron, Annu. Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include peripheral blood mononuclear cells (PBMC), natural killer (NK) cells, monocytes, cytotoxic T cells, and neutrophils; with PBMCs and NK cells being preferred. The effector cells can be isolated from a native source, e.g., from blood.

"Complement dependent cytotoxicity" or "CDC refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1996), can be performed.

The term "therapeutically effective amount" refers to an amount of an antibody, antibody fragment, or derivative to treat a disease or disorder in a subject. In the case of tumor (e.g., a cancerous tumor), the therapeutically effective amount of the antibody or antibody fragment (e.g., a multispecific antibody or antibody fragment) may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antibody or antibody fragment may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of metastases, the size of the primary tumor, or the size or number of the blood vessels in angiogenic disorders.

The terms "cancer" and "cancerous" refer to or describe the physiological condition in mammals that is typically characterized by unregulated cell growth/proliferation. Included in this definition are benign and malignant cancers. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastric or stomach cancer including gastrointestinal cancer, pancreatic cancer, glioblastoma, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer (e.g., renal cell carcinoma), liver cancer, prostate cancer, vulval cancer, thyroid cancer, hepatic carcinoma, anal carcinoma, penile carcinoma, melanoma, and various types of head and neck cancer. By "early stage cancer" is meant a cancer that is not invasive or metastatic or is classified as a Stage 0, I, or II cancer. The term "precancerous" refers to a condition or a growth that typically precedes or develops into a cancer. By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer.

An "allergic or inflammatory disorder" herein is a disease or disorder that results from a hyper-activation of the immune system of an individual. Exemplary allergic or inflammatory disorders include, but are not limited to, asthma, psoriasis, rheumatoid arthritis, atopic dermatitis, multiple sclerosis, systemic lupus, erythematosus, eczema, organ transplantation, age-related mucular degeneration, Crohn's disease, ulcerative colitis, eosinophilic esophagitis, and autoimmune diseases associated with inflammation.

An "autoimmune disease" herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, chorioditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions, allergic reaction, eczema including allergic or atopic eczema, asthma such as asthma bronchiale, bronchial asthma, and auto-immune asthma, conditions involving infiltration of T cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barré syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal garnmopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia areata, CREST syndrome (calcinosis, Raynaud's phenomenon, esophageal dysmotility, sclerodactyly, and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemic-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to antispermatozoan antibodies, non-malignant thymoma, vitiligo, SCID and Epstein-Barr virus-associated diseases, acquired immune deficiency syndrome (AIDS), parasitic diseases such as Leishmania, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

The term "cytotoxic agent" as used herein refers to a substance that inhibits or prevents the function of a cell and/or causes destruction of a cell. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $Ra^{223}$, $P^{32}$, and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor, anticancer, and chemotherapeutic agents disclosed herein. Other cytotoxic agents are described herein. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-am inocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma 1 (see, e.g., Agnew, Chem Intl. Ed. Engl. 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; am inolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; am inopterin; ibandronate; topoisomerase inhibitor RFS 2000; difluorometlhylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (e.g., vincristine and vinblastine), taxanes, and topoisomerase II inhibitors such as doxorubicin, epirubicin, daunorubicin, etoposide, and bleomycin. The agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Anti-cancer therapy" as used herein refers to a treatment that reduces or inhibits cancer in a subject. Examples of anti-cancer therapy include cytotoxic radiotherapy as well as the administration of a therapeutically effective amount of a cytotoxic agent, a chemotherapeutic agent, a growth inhibitory agent, a cancer vaccine, an angiogenesis inhibitor, a prodrug, a cytokine, a cytokine antagonist, a corticosteroid, an immunosuppressive agent, an anti-emetic, an antibody or antibody fragment, or an analgesic to the subject.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone (HGH), N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor (EGF); hepatic growth factor; fibroblast growth factor (FGF); prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-1 beta, IL-2, IL-3, IL-4, IL-5, IL-6, IL-7, IL-8, IL-9, IL-10, IL-11, IL-12; IL-18 a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

By "cytokine antagonist" is meant a molecule that partially or fully blocks, inhibits, or neutralizes a biological activity of at least one cytokine. For example, the cytokine antagonists may inhibit cytokine activity by inhibiting cytokine expression and/or secretion, or by binding to a cytokine or to a cytokine receptor. Cytokine antagonists include antibodies, synthetic or native-sequence peptides, immunoadhesins, and small-molecule antagonists that bind to a cytokine or cytokine receptor. The cytokine antagonist is optionally conjugated with or fused to a cytotoxic agent. Exemplary TNF antagonists are etanercept (ENBREL®), infliximab (REMICADE®), and adalimumab (HUMIRA™).

The term "immunosuppressive agent" as used herein refers to substances that act to suppress or mask the immune system of the subject being treated. This includes substances that suppress cytokine production, downregulate or suppress self-antigen expression, or mask the MHC antigens. Examples of immunosuppressive agents include 2-amino-6-aryl-5-substituted pyrimidines (see U.S. Pat. No. 4,665,077); mycophenolate mofetil such as CELLCEPT®; azathioprine (IMURAN®, AZASAN®/6-mercaptopurine; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids and glucocorticosteroids, e.g., prednisone, prednisolone such as PEDIAPRED® (prednisolone sodium phosphate) or ORAPRED® (prednisolone sodium phosphate oral solution), methylprednisolone, and dexamethasone; methotrexate (oral or subcutaneous) (RHEUMATREX®, TREXALL™); hydroxycloroquine/chloroquine; sulfasalazine; leflunomide; cytokine or cytokine receptor antagonists including anti-interferon-$\gamma$, -$\beta$, or -$\alpha$ antibodies, anti-tumor necrosis factor-$\alpha$ antibodies (infliximab or adalimumab), anti-TNF$\alpha$ immunoadhesin (ENBREL®, etanercept), anti-tumor necrosis factor-$\beta$ antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; polyclonal or pan-T antibodies, or monoclonal anti-CD3 or anti-CD4/CD4a antibodies; soluble peptide containing a LFA-3 binding domain (WO 90/08187); streptokinase; TGF-$\beta$; streptodornase; RNA or DNA from the host; FK506; RS-61443; deoxyspergualin; rapamycin; T-cell receptor (Cohen et al., U.S. Pat. No. 5,114,721); T-cell receptor fragments (Offner et al. Science 251: 430-432 (1991); WO 90/11294; laneway, Nature 341:482 (1989); and WO 91/01133); T cell receptor antibodies (EP 340,109) such as T10B9; cyclophosphamide (CYTOXAN®); dapsone; penicillamine (CUPRIMINE®); plasma exchange; or intravenous immunoglobulin (IVIG). These may be used alone or in combination with each other, particularly combinations of steroid and another immunosuppressive agent or such combinations followed by a maintenance dose with a non-steroid agent to reduce the need for steroids.

An "analgesic" refers to a drug that acts to inhibit or suppress pain in a subject. Exemplary analgesics include non-steroidal anti-inflammatory drugs (NSAIDs) including ibuprofen (MOTRIN®), naproxen (NAPROSYN®), acetylsalicylic acid, indomethacin, sulindac, and tolmetin, including salts and derivatives thereof, as well as various other medications used to reduce the stabbing pains that may occur, including anticonvulsants (gabapentin, phenyloin, carbamazepine) or tricyclic antidepressants. Specific examples include acetaminophen, aspirin, am itriptyline (ELAVIL®), carbamazepine (TEGRETOL®), phenyltoin (DILANTIN®), gabapentin (NEURONTIN®), (E)-N-Vanillyl-8-methyl-6-noneamid (CAPSAICIN®), or a nerve blocker.

"Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including methylprednisolone), dexamethasone triamcinolone, and betamethasone.

A "cancer vaccine," as used herein is a composition that stimulates an immune response in a subject against a cancer. Cancer vaccines typically consist of a source of cancer-associated material or cells (antigen) that may be autologous (from self) or allogenic (from others) to the subject, along with other components (e.g., adjuvants) to further stimulate and boost the immune response against the antigen. Cancer vaccines can result in stimulating the immune system of the subject to produce antibodies to one or several specific antigens, and/or to produce killer T cells to attack cancer cells that have those antigens.

"Cytotoxic radiotherapy" as used herein refers to radiation therapy that inhibits or prevents the function of cells and/or causes destruction of cells. Radiation therapy may include, for example, external beam irradiation or therapy with a radioactive labeled agent, such as an antibody. The term is intended to include use of radioactive isotopes (e.g., $At^{211}$, $^{131}I$, $I^{125}$, $Y^{90}$, $Re^{186}$, $Re^{188}$, $Sm^{153}$, $Bi^{212}$, $Ra^{223}$, $P^{32}$ and radioactive isotopes of Lu).

A "subject" is a vertebrate, such as a mammal, e.g., a human. Mammals include, but are not limited to, farm animals (such as cows), sport animals, pets (such as cats, dogs and horses), primates, mice, and rats.

Except where indicated otherwise by context, the terms "first" hinge-containing polypeptide and "second" hinge-containing polypeptide, and variations thereof, are merely generic identifiers, and are not to be taken as identifying a specific or a particular polypeptide or component of antibodies of the invention.

Commercially available reagents referred to in the Examples, if any, were used according to manufacturer's instructions unless otherwise indicated. The source of those cells identified in the following Examples, if any, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., supra; Ausubel et al., Current Protocols in Molecular Biology (Green Publishing Associates and Wiley Interscience, N Y, 1989); Innis et al., PCR Protocols: A Guide to Methods and Applications (Academic Press, Inc., NY, 1990); Harlow et al., Antibodies: A Laboratory Manual (Cold Spring Harbor Press, Cold Spring Harbor, 1988); Gait, Oligonucleotide Synthesis (IRL Press, Oxford, 1984); Freshney, Animal Cell Culture, 1987; Coligan et al., Current Protocols in Immunology, 1991.

Throughout this specification and claims, the word "comprise," or variations such as "comprises" or "comprising," will be understood to imply the inclusion of a stated integer or group of integers but not the exclusion of any other integer or group of integers.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

II. Methods of Preparing Heteromultimeric Proteins in Mammalian Host Cells

Production of heteromultimeric proteins, e.g., multispecific antibodies, using current techniques has drawbacks including the production of a mixture of products, reduced yield and decreased/elimination of effector function among others. Thus, it is desirable to produce heteromultimeric proteins efficiently and at high levels.

The production of antibody molecules, by various means, is generally well understood. U.S. Pat. No. 6,331,415 (Cabilly et al.), for example, describes a method for the recombinant production of immunoglobulin where the heavy and light chains are expressed simultaneously from a single vector or from two separate vectors in a single cell. Wibbenmeyer et al., (1999, Biochim Biophys Acta 1430(2): 191-202) and Lee and Kwak (2003, J. Biotechnology 101:189-198) describe the production of monoclonal antibodies from separately produced heavy and light chains, using plasm ids expressed in separate cultures of E. coli. Various other techniques relevant to the production of antibodies are described in, e.g., Harlow, et al., ANTIBODIES: A LABORATORY MANUAL, Cold Spring Harbor Laboratory Press, Cold Spring Harbor, N.Y., (1988) and WO2006028936. Yet each of these have drawbacks such as low yield, use of chemicals.

The methods provided herein are based on the surprising finding that a first hinge-containing polypeptide and a first light chain expressed and secreted from a first mammalian host cell and a second hinge-containing polypeptide and a second light chain expressed and secreted by a second mammalian host cell assemble to form a heteromultimeric protein in a combined culture medium. As discussed in further detail below, the combined culture medium can be obtained by culturing the first mammalian host cell in a first cell culture, culturing a second mammalian host cell in a second cell culture, harvesting the first and second culture media without disrupting the cell membrane of the first and second host cells, and combining the harvested first and second culture media to obtain the combined culture medium that comprises the heteromultimeric protein. Alternatively, the combined culture medium can be obtained by culturing the first and second mammalian host cells in a combined cell culture, and harvesting from the combined culture the combined cell culture medium that comprises the heteromultimeric protein. In certain embodiments, the harvesting step comprises removing the first and/or second host cells without disrupting cell membrane.

The methods provided herein are surprising, as it was generally believed that the protein quality control system of eukaryotic cells (such as mammalian cells) may not efficiently produce incomplete antibodies. See, e.g., Spiess et al. (2013) Nature, 31(8): 753-758.

Applicants have also surprisingly found that a heteromultimeric protein can be formed with high yield under reducing conditions in a combined culture medium comprising a first homodimer comprising two first hinge-containing polypeptides and two first light chains that has been secreted by a first host cell and a second homodimer comprising two second hinge-containing polypeptides and two second light chains that has been secreted from by a second host cell.

Thus, in certain embodiments, provided are methods of preparing a heteromultimeric protein comprising i) a first hinge-containing polypeptide having a first heterodimerization domain, wherein the first hinge-containing polypeptide is associated with a first light chain, and ii) a second hinge-containing polypeptide having a second heterodimerization domain, wherein the second hinge-containing polypeptide is associated with a second light chain, wherein the second heterodimerization domain interacts with the first heterodimerization domain at an interface, and wherein the first and second hinge-containing polypeptides are linked by at least one interchain disulfide bond, the method comprising the steps of:

(a) culturing a first host cell capable of expressing and secreting a first hinge-containing polypeptide and a first light chain, (b) culturing a second host cell capable of expressing and secreting a second hinge-containing polypeptide and a second light chain; and, (c) obtaining a combined culture medium for the first host cell and the second host cell without disrupting cell membrane of the first and second host cells, wherein the combined culture medium comprises the heteromultimeric protein, and wherein the first host cell and the second host cell are each a mammalian cell.

In certain embodiments, provided are methods of preparing a heteromultimeric protein comprising i) a first hinge-containing polypeptide having a first heterodimerization domain, wherein the first hinge-containing polypeptide is associated with a first light chain, and ii) a second hinge-containing polypeptide having a second heterodimerization domain, wherein the second hinge-containing polypeptide is associated with a second light chain, wherein the second heterodimerization domain interacts with the first heterodimerization domain at an interface, and wherein the first and second hinge-containing polypeptides are linked by at least one interchain disulfide bond, the method comprising the steps of:

(a) culturing a first host cell capable of expressing a first hinge-containing polypeptide and a first light chain, wherein a first homodimer comprising two first hinge-containing polypeptides and two first light chains is secreted;

(b) culturing a second host cell capable of expressing a second hinge-containing polypeptide and a second light chain, wherein a second homodimer comprising two second hinge-containing polypeptides and two second light chains is secreted;

(c) obtaining a combined culture medium for the first host cell and the second host cell, wherein the combined culture medium comprises the first homodimer and the second homodimer;

(d) incubating the combined culture medium under reducing conditions, and;

(e) obtaining the heteromultimeric protein, wherein the first host cell and the second host cell are each a mammalian cell.

In certain embodiments, the combined culture medium is obtained without disrupting cell membrane of the first and second host cells. In certain embodiments, the method further comprises adding a reducing agent. In certain embodiments, the reducing conditions are sufficient to allow formation of the heteromultimeric protein.

In certain embodiments, the first hinge-containing polypeptide and the first light chain comprise a first half-antibody. In certain embodiments, the second hinge-containing polypeptide and second light chain comprise a second half-antibody.

In certain embodiments, about 99%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, or less than about 5% (such as about 4%, about 3%, about 2%, or about 1%) of the first hinge containing polypeptide and first light chain (e.g., the first half antibody) present in the combined culture medium is in the form of a first homodimer prior to incubation under reducing conditions or prior to adding a reducing agent, including any range between these values. In certain embodiments, about 10% to about 75%, about 20% to about 65%, or about 30% to about 55% of the first hinge containing polypeptide and first light chain (e.g., the first half antibody) present in the combined culture medium is in the form of a first homodimer prior to incubation under reducing conditions or prior to adding a reducing agent.

In certain embodiments, about 99%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, or less than about 5% (such as about 4%, about 3%, about 2%, or about 1%) of the second hinge containing polypeptide and second light chain (e.g., the second half antibody) present in the combined culture medium is in the form of a second homodimer prior to incubation under reducing conditions or prior to adding a reducing agent, including any range between these values. In certain embodiments, about 10% to about 75%, about 20% to about 65%, or about 30% to about 55% of the second hinge containing polypeptide and second light chain (e.g., the second half antibody) present in the combined culture medium is in the form of a second homodimer prior to incubation under reducing conditions or prior to adding a reducing agent.

In certain embodiments, the combined culture medium comprises less than about 75%, less than about 70%, less than about 65%, less than about 60%, less than about 55%, less than about 50%, less than about 45%, less than about 40%, less than about 35%, less than about 30%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6% less than about 5%, less than about 4%, less than about 3%, less than about 2% or less than about 1% of the first homodimer after incubation under reducing conditions or after adding a reducing agent, including any range between these values. In certain embodiments, the combined culture medium comprises less than about 2% to about 20%, less than about 5% to about 15%, or less than about 10% to about 15% of the first homodimer after incubation under reducing conditions or after adding a reducing agent.

In certain embodiments, the combined culture medium comprises less than about 75%, less than about 70%, less than about 65%, less than about 60%, less than about 55%, less than about 50%, less than about 45%, less than about 40%, less than about 35%, less than about 30%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6% less than about 5%, less than about 4%, less than about 3%, less than about 2% or less than about 1% of the second homodimer after incubation under reducing conditions or after adding a reducing agent, including any range between these values. In certain embodiments, the combined culture medium comprises less than about 2% to about 20%, less than about 5% to about 15%, or less than about 10% to about 15% of the second homodimer after incubation under reducing conditions or after adding a reducing agent.

In certain embodiments, provided is a method of preparing a heteromultimeric protein comprising i) a first hinge-containing polypeptide having a first heterodimerization domain, wherein the first hinge-containing polypeptide is associated with a first light chain, and ii) a second hinge-containing polypeptide having a second heterodimerization domain, wherein the second hinge-containing polypeptide is associated with a second light chain, wherein the second heterodimerization domain interacts with the first heterodimerization domain at an interface, and wherein the first and second hinge-containing polypeptides are linked by at least one interchain disulfide bond, the method comprising the steps of:

(a) culturing a first host cell comprising a first nucleic acid that encodes the first hinge-containing polypeptide and a second nucleic acid that encodes the first light chain;

(b) culturing a second host cell comprising a third nucleic acid that encodes the second hinge-containing polypeptide and a fourth nucleic acid that encodes the second light chain; and, (c) obtaining a combined culture medium for the first host cell and the second host cell, wherein the combined culture medium comprises the heteromultimeric protein, and wherein the first host cell and the second host cell are each a mammalian cell. In certain embodiments, the first and second nucleic acids are one nucleic acid molecule; while in certain other embodiments, the first and second nucleic acids are different nucleic acid molecules. In certain embodiments, the third and fourth nucleic acids are one nucleic acid molecule; while in certain other embodiments, the third and fourth nucleic acids are different nucleic acid molecules.

In certain embodiments, the invention provides methods of preparing a heteromultimeric protein comprising i) a first hinge-containing polypeptide having a first heterodimerization domain, wherein the first hinge-containing polypeptide is associated with a first light chain, and ii) a second hinge-containing polypeptide having a second heterodimerization domain, wherein the second hinge-containing polypeptide is associated with a second light chain, wherein the second heterodimerization domain interacts with the first heterodimerization domain at an interface, and wherein the first and second hinge-containing polypeptides are linked by at least one interchain disulfide bond, the method comprising the steps of:

(a) culturing a first host cell comprising a first nucleic acid that encodes the first hinge-containing polypeptide and a second nucleic acid that encodes the first light chain, wherein the first host cell is capable of expressing the first hinge containing polypeptide and the first light chain, and wherein a first homodimer comprising two first hinge-containing polypeptides and two first light chains is secreted;

(b) culturing a second host cell comprising a third nucleic acid that encodes the second hinge-containing polypeptide and a fourth nucleic acid that encodes the second light chain, wherein the second host cell is capable of expressing the second hinge containing polypeptide and the second light chain, and wherein a second homodimer comprising two second hinge-containing polypeptides and two second light chains is secreted;

(c) obtaining a combined culture medium for the first host cell and the second host cell without disrupting cell membrane of the first and second host cells, wherein the combined culture medium comprises the first homodimer and the second homodimer;

(d) incubating the combined culture medium under reducing conditions sufficient to allow of the heteromultimeric protein, and;

(e) obtaining the heteromultimeric protein, wherein the first host cell and the second host cell are each a mammalian cell. In certain embodiments, the first and second nucleic acids are one nucleic acid molecule; while in certain other embodiments, the first and second nucleic acids are different nucleic acid molecules. In certain embodiments, the third and fourth nucleic acids are one nucleic acid molecule; while in certain other embodiments, the third and fourth nucleic acids are different nucleic acid molecules. In certain embodiments, the method further comprises adding a reducing agent to the combined culture medium.

In certain embodiments, provided is a method of preparing a heteromultimeric protein comprising i) a first half antibody comprising a first hinge-containing polypeptide having a first heterodimerization domain, wherein the first hinge-containing polypeptide is associated with a first light chain, and ii) a second half-antibody comprising a second hinge-containing polypeptide having a second heterodimerization domain, wherein the second hinge-containing polypeptide is associated with a second light chain, wherein the second heterodimerization domain interacts with the first heterodimerization domain at an interface, and wherein the first and second hinge-containing polypeptides are linked by at least one interchain disulfide bond, the method comprising the steps of:

(a) culturing a first host cell comprising a first nucleic acid that encodes the first hinge-containing polypeptide and a second nucleic acid that encodes the first light chain;

(b) culturing a second host cell comprising a third nucleic acid that encodes the second hinge-containing polypeptide and a fourth nucleic acid that encodes the second light chain; and, (c) obtaining a combined culture medium for the first host cell and the second host cell, wherein the combined culture medium comprises the heteromultimeric protein, and wherein the first host cell and the second host cell are each a mammalian cell. In certain embodiments, the method further comprises adding a reducing agent to the combined culture medium.

In certain embodiments, the invention provides methods of preparing a heteromultimeric protein comprising i) a first half antibody comprising a first hinge-containing polypeptide having a first heterodimerization domain, wherein the first hinge-containing polypeptide is associated with a first light chain, and ii) a second half antibody comprising a second hinge-containing polypeptide having a second heterodimerization domain, wherein the second hinge-containing polypeptide is associated with a second light chain, wherein the second heterodimerization domain interacts with the first heterodimerization domain at an interface, and wherein the first and second hinge-containing polypeptides are linked by at least one interchain disulfide bond, the method comprising the steps of:

(a) culturing a first host cell comprising a first nucleic acid that encodes the first hinge-containing polypeptide and a second nucleic acid that encodes the first light chain, wherein the first host cell is capable of expressing the first hinge containing polypeptide and the first light chain, and wherein a first homodimer comprising two first hinge-containing polypeptides and two first light chains is secreted;

(b) culturing a second host cell comprising a third nucleic acid that encodes the second hinge-containing polypeptide and a fourth nucleic acid that encodes the second light chain, wherein the second host cell is capable of expressing the second hinge containing polypeptide and the second light chain, and wherein a second homodimer comprising two second hinge-containing polypeptides and two second light chains is secreted;

(c) obtaining a combined culture medium for the first host cell and the second host cell without disrupting cell membrane of the first and second host cells, wherein the combined culture medium comprises the first homodimer and the second homodimer;

(d) incubating the combined culture medium under reducing conditions sufficient to allow formation of the heteromultimeric protein, and;

(e) obtaining the heteromultimeric protein, wherein the first host cell and the second host cell are each a mammalian cell. In certain embodiments, the method further comprises adding a reducing agent to the combined culture medium.

In certain embodiments, the invention provides methods of preparing a heteromultimeric protein comprising i) a first hinge-containing polypeptide having a first heterodimerization domain, wherein the first hinge-containing polypeptide is associated with a first light chain, and ii) a second hinge-containing polypeptide having a second heterodimerization domain, wherein the second hinge-containing polypeptide is associated with a second light chain, wherein the second heterodimerization domain interacts with the first heterodimerization domain at an interface, and wherein the first and second hinge-containing polypeptides are linked by at least one interchain disulfide bond, the method comprising the steps of:

(a) culturing a first mammalian host cell comprising a first nucleic acid that encodes the first hinge-containing polypeptide and a second nucleic acid that encodes the first light chain in a first cell culture;

(b) culturing a second mammalian host cell comprising a third nucleic acid that encodes the second hinge-containing polypeptide and a fourth nucleic acid that encodes the second light chain in a second cell culture;

(c) harvesting a first culture medium from the first mammalian host cell;

(d) harvesting a second culture medium from the second mammalian host cell;

(e) combining the first culture medium and the second culture medium to obtain the combined culture medium, wherein the combined culture medium comprises the heteromultimeric protein. In certain embodiments, harvesting the first culture medium comprises removing the first host cell from the first cell culture. In certain embodiments, harvesting the second culture medium comprises removing the second host cell from the second cell culture. In certain embodiments, the method further comprises adding a reducing agent to the combined culture medium.

In certain embodiments, provided are methods of preparing a heteromultimeric protein comprising i) a first hinge-containing polypeptide having a first heterodimerization domain, wherein the first hinge-containing polypeptide is associated with a first light chain, and ii) a second hinge-containing polypeptide having a second heterodimerization domain, wherein the second hinge-containing polypeptide is associated with a second light chain, wherein the second heterodimerization domain interacts with the first heterodimerization domain at an interface, and wherein the first and second hinge-containing polypeptides are linked by at least one interchain disulfide bond, the method comprising the steps of:

(a) culturing a first host cell comprising a first nucleic acid that encodes the first hinge-containing polypeptide and a second nucleic acid that encodes the first light chain in a first cell culture wherein the first host cell is capable of expressing the first hinge containing polypeptide and the first light chain, and wherein a first homodimer comprising two first hinge-containing polypeptides and two first light chains is secreted;

(b) culturing a second host cell comprising a third nucleic acid that encodes the second hinge-containing polypeptide and a fourth nucleic acid that encodes the second light chain in a second cell culture, wherein the second host cell is capable of expressing the second hinge containing polypeptide and the second light chain, and wherein a second homodimer comprising two second hinge-containing polypeptides and two second light chains is secreted;

(c) harvesting a first culture medium from the first mammalian host cell, wherein the first culture medium comprises the first homodimer;

(d) harvesting a second culture medium from the second mammalian host cell, wherein the second culture medium comprises the second homodimer;

(e) combining the first culture medium and the second culture medium to obtain the combined culture medium, wherein the combined culture medium comprises the first homodimer and the second homodimer;

(f) incubating the combined culture medium under reducing conditions sufficient to allow formation of the heteromultimeric protein, and;

(g) obtaining the heteromultimeric protein, wherein the first host cell and the second host cell are each a mammalian cell. In certain embodiments, harvesting the first culture medium comprises removing the first host cell from the first cell culture. In certain embodiments, harvesting the second culture medium comprises removing the second host cell from the second cell culture. In certain embodiments, the method further comprises adding a reducing agent to the combined culture medium.

In certain embodiments, the invention provides methods of preparing a heteromultimeric protein comprising i) a first half antibody comprising a first hinge-containing polypeptide having a first heterodimerization domain, wherein the first hinge-containing polypeptide is associated with a first light chain, and ii) a second half-antibody comprising a second hinge-containing polypeptide having a second heterodimerization domain, wherein the second heterodimerization domain interacts with the first heterodimerization domain at an interface, and wherein the first and second half-antibodies are linked by at least one interchain disulfide bond, the method comprising the steps of:

(a) culturing a first mammalian host cell comprising a first nucleic acid that encodes a first hinge-containing polypeptide and a second nucleic acid that encodes a first light chain in a first cell culture;

(b) culturing a second mammalian host cell comprising a third nucleic acid that encodes a second hinge-containing polypeptide and a fourth nucleic acid that encodes a second light chain in a second cell culture;

(c) harvesting a first culture medium from the first mammalian host cell;

(d) harvesting a second culture medium from the second mammalian host cell;

(e) combining the first culture medium and the second culture medium to obtain the combined culture medium, wherein the combined culture medium comprises the heteromultimeric protein. In certain embodiments, harvesting the first culture medium comprises removing the first host cell from the first cell culture. In certain embodiments, harvesting the second culture medium comprises removing the second host cell from the second cell culture.

In certain embodiments, provided are methods of preparing a heteromultimeric protein comprising i) a first half-antibody comprising a first hinge-containing polypeptide having a first heterodimerization domain, wherein the first hinge-containing polypeptide is associated with a first light chain, and ii) a second half-antibody comprising a second hinge-containing polypeptide having a second heterodimerization domain, wherein the second hinge-containing polypeptide is associated with a second light chain, wherein the second heterodimerization domain interacts with the first heterodimerization domain at an interface, and wherein the first and second hinge-containing polypeptides are linked by at least one interchain disulfide bond, the method comprising the steps of:

(a) culturing a first host cell comprising a first nucleic acid that encodes the first hinge-containing polypeptide and a second nucleic acid that encodes the first light chain in a first cell culture, wherein the first host cell is capable of expressing the first hinge containing polypeptide and the first light chain, and wherein a first homodimer comprising two first hinge-containing polypeptides and two first light chains is secreted;

(b) culturing a second host cell comprising a third nucleic acid that encodes the second hinge-containing polypeptide and a fourth nucleic acid that encodes the second light chain in a second cell culture, wherein the second host cell is capable of expressing the second hinge containing polypeptide and the second light chain, and wherein a second homodimer comprising two second hinge-containing polypeptides and two second light chains is secreted;

(c) harvesting a first culture medium from the first mammalian host cell, wherein the first culture medium comprises a first homodimer;

(d) harvesting a second culture medium from the second mammalian host cell, wherein the second culture medium comprises the second homodimer;

(e) combining the first culture medium and the second culture medium to obtain a combined culture medium, wherein the combined culture medium comprises the first homodimer and the second homodimer;

(f) incubating the combined culture medium under reducing conditions sufficient to allow formation of the heteromultimeric protein, and;

(g) obtaining the heteromultimeric protein, wherein the first host cell and the second host cell are each a mammalian cell. In certain embodiments, harvesting the first culture medium comprises removing the first host cell from the first cell culture. In certain embodiments, harvesting the second culture medium comprises removing the second host cell from the second cell culture. In certain embodiments, the method further comprises adding a reducing agent to the combined culture medium.

In certain embodiments, the invention provides methods of preparing a heteromultimeric protein comprising i) a first hinge-containing polypeptide having a first heterodimerization domain, wherein the first hinge-containing polypeptide is associated with a first light chain, and ii) a second hinge-containing polypeptide having a second heterodimerization domain, wherein the second hinge-containing polypeptide is associated with a second light chain, wherein the second heterodimerization domain interacts with the first heterodimerization domain at an interface, and wherein the first and second hinge-containing polypeptides are linked by at least one interchain disulfide bond, the method comprising the steps of:

(a) culturing a first mammalian host cell comprising a first nucleic acid that encodes the first hinge-containing polypeptide and a second nucleic acid that encodes the first light chain;

(b) culturing a second mammalian host cell comprising a third nucleic acid that encodes the second hinge-containing polypeptide and a fourth nucleic acid that encodes the second light chain; and (c) harvesting culture medium of a combined cell culture comprising the first host cell and the second host cell to obtain a combined culture medium for the first mammalian host cell and the second mammalian host cell, wherein the combined culture medium comprises the heteromultimeric protein.

In certain embodiments, provided are methods of preparing a heteromultimeric protein comprising i) a first hinge-containing polypeptide having a first heterodimerization domain, wherein the first hinge-containing polypeptide is associated with a first light chain, and ii) a second hinge-containing polypeptide having a second heterodimerization domain, wherein the second hinge-containing polypeptide is associated with a second light chain, wherein the second heterodimerization domain interacts with the first heterodimerization domain at an interface, and wherein the first and second hinge-containing polypeptides are linked by at least one interchain disulfide bond, the method comprising the steps of:

(a) culturing a first mammalian host cell comprising a first nucleic acid that encodes the first hinge-containing polypeptide and a second nucleic acid that encodes the first light chain, wherein the first host cell is capable of expressing the first hinge containing polypeptide and the first light chain, and wherein a first homodimer comprising two first hinge-containing polypeptides and two first light chains is secreted;

(b) culturing a second mammalian host cell comprising a third nucleic acid that encodes the second hinge-containing polypeptide and a fourth nucleic acid that encodes the second light chain, wherein the second host cell is capable of expressing the second hinge containing polypeptide and the second light chain, and wherein a second homodimer comprising two second hinge-containing polypeptides and two second light chains is secreted;

(c) harvesting culture medium of a combined cell culture comprising the first host cell and the second host cell to obtain a combined culture medium for the first mammalian host cell and the second mammalian host cell, wherein the culture medium of the combined cell culture comprises the first homodimer and the second homodimer;

(d) incubating the culture medium under reducing conditions sufficient to allow formation of the heteromultimeric protein, and;

(e) obtaining the heteromultimeric protein, wherein the first host cell and the second host cell are each a mammalian cell. In certain embodiments, the method further comprises adding a reducing agent to the combined culture medium.

In certain embodiments, the invention provides methods of preparing a heteromultimeric protein comprising i) a first half antibody comprising a first hinge-containing polypeptide having a first heterodimerization domain, wherein the first hinge-containing polypeptide is associated with a first light chain, and ii) a second half-antibody comprising a second hinge-containing polypeptide having a second heterodimerization domain, wherein the second heterodimerization domain interacts with the first heterodimerization domain at an interface, and wherein the first and second hinge-containing polypeptides are linked by at least one interchain disulfide bond, the method comprising the steps of:

(a) culturing a first mammalian host cell comprising a first nucleic acid that encodes a first hinge-containing polypeptide and a second nucleic acid that encodes a first light chain;

(b) culturing a second mammalian host cell comprising a third nucleic acid that encodes a second hinge-containing polypeptide and a fourth nucleic acid that encodes a second light chain; and (c) harvesting culture medium of a combined cell culture comprising the first host cell and the second host cell to obtain a combined culture medium for the first mammalian host cell and the second mammalian host cell, wherein the combined culture medium comprises the heteromultimeric protein.

In certain embodiments, provided are methods of preparing a heteromultimeric protein comprising i) first half-antibody comprising a first hinge-containing polypeptide having a first heterodimerization domain, wherein the first hinge-containing polypeptide is associated with a first light chain, and ii) a second half antibody comprising a second hinge-containing polypeptide having a second heterodimerization domain, wherein the second hinge-containing polypeptide is associated with a second light chain, wherein the second heterodimerization domain interacts with the first heterodimerization domain at an interface, and wherein the first and second hinge-containing polypeptides are linked by at least one interchain disulfide bond, the method comprising the steps of:

(a) culturing a first mammalian host cell comprising a first nucleic acid that encodes the first hinge-containing polypeptide and a second nucleic acid that encodes the first light chain, wherein the first host cell is capable of expressing the first hinge containing polypeptide and the first light chain, and wherein a first homodimer comprising two first hinge-containing polypeptides and two first light chains is secreted;

(b) culturing a second mammalian host cell comprising a third nucleic acid that encodes the second hinge-containing polypeptide and a fourth nucleic acid that encodes the second light chain, wherein the second host cell is capable of expressing the second hinge containing polypeptide and the second light chain, and wherein a second homodimer comprising two second hinge-containing polypeptides and two second light chains is secreted;

(c) harvesting culture medium of a combined cell culture comprising the first host cell and the second host cell to obtain a combined culture medium for the first mammalian host cell and the second mammalian host cell, wherein the culture medium of the combined cell culture comprises the first homodimer and the second homodimer;

(d) incubating the culture medium under reducing conditions sufficient to allow formation of the heteromultimeric protein, and;

(e) obtaining the heteromultimeric protein, wherein the first host cell and the second host cell are each a mammalian cell. In certain embodiments, the method further comprises adding a reducing agent to the combined culture medium.

In certain embodiments, culturing of the combined cell culture comprising the first host cell and the second host cell is carried out at a temperature between about 25° C. and 40° C. In certain embodiments, culturing of the combined cell culture comprising the first host cell and the second host cell is carried out at a temperature between about 30° C. and 37° C. In certain embodiments, culturing of the combined cell culture comprising the first host cell and the second host cell is carried out at a pH between about 7.2 and 8.7.

In certain embodiments, the combined culture medium is incubated at a temperature between about 4° C. and 40° C. In certain embodiments, the combined culture medium is incubated at a temperature between about 30° C. and 37° C. In certain embodiments, the combined culture medium is incubated at a temperature between about 4° C. and 8° C.

In certain embodiments, the combined culture medium is agitated. In certain embodiments, the combined culture medium is agitated for about 6 hours, about 12 hours, about 18 hours, about 24 hours, about 1 day, about 2 days, about 3 days, about 4 days, about 5 days, about 6 days, about 7 days, about 8 days, or more than 8 days after the combined culture medium is obtained. In some embodiments, the combined culture is intermittently agitated.

In certain embodiments, the methods further comprise isolating the heteromultimeric protein (such as bispecific antibody) from the combined culture medium. In certain embodiments, the heteromultimeric protein (such as bispecific antibody) is isolated using a protein A column.

In certain embodiments, the methods include adding a reducing agent during production of the heteromultimeric protein (such as a bispecific antibody.) In certain embodiments of the methods provided herein, the reducing agent used is glutathione, 2-mercaptoethanol, 2-mercaptoethylamine, tris(2-carboxyethyl)phosphine (TCEP), cysteine, cysteine, dithiothreitol, cysteindithiothreitol, dithiolbutylamine, or combinations thereof. In certain embodiments, the reducing agent is reduced glutathione. In certain embodiments, the reducing agent is not 2-mercaptoethanol. In certain embodiments, the reducing agent is not dithiothreitol.

In certain embodiments wherein first and second mammalian host cells are cultured separately, i.e., grown in separate cultures, the reducing agent is added to the first cell culture medium and to the second cell culture medium before the first and second cell culture media are harvested and combined to obtain the combined culture medium. In certain embodiments wherein the first and second mammalian host cells are grown in the same culture, the reducing agent is added to the culture medium of the combined cell culture before the combined cell culture is harvested to obtain the combined culture medium.

In certain embodiments, the reducing agent is added about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, or about 30 hours before the harvesting step, including any range in between these values.

In certain embodiments, the reducing agent is added to the combined culture medium. In certain embodiments, the combined culture medium containing the reducing agent is incubated for about 4 hours, about 5 hours, about 6 hours, 7 hours, about 8 hours, about 9 hours, about 10 hours, about 11 hours, about 12 hours, about 15 hours, about 18 hours, about 21 hours, about 24 hours, about 2 days, about 3 days, about 4 days, about 5 days, about 6 days, or about 7 days, including any range in between these values.

In certain embodiments, the reducing agent (such as glutathione) is added to the combined cell culture to achieve final concentration of about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, or about 30 mM, including any range in between these values. In certain embodiments, the reducing agent (such as glutathione) is added to the combined cell culture to achieve a final concentration of less than 20 mM. In certain embodiments, the reducing agent (such as glutathione) is added to the combined cell culture to achieve a final concentration of no more than 20 mM.

In certain embodiments, the reducing agent is added to the combined culture medium before isolating the heteromultimeric protein (such as bispecific antibody) from the combined culture medium. In certain embodiments, the combined culture medium containing the reducing agent is incubated for about 4 hours, about 5 hours, about 6 hours, 7 hours, about 8 hours, about 9 hours, about 10 hours, about 11 hours, about 12 hours, about 15 hours, about 18 hours, about 21 hours, about 24 hours, about 2 days, about 3 days, about 4 days, about 5 days, about 6 days, or about 7 days before isolating the heteromultimeric protein (such as bispecific antibody) from the combined culture medium containing the reducing agent, including any range in between these values. In some embodiments, the heteromultimeric protein is isolated using a protein A column.

In certain embodiments, the reducing agent (such as glutathione) is added to the combined culture medium to achieve final concentration of about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, or about 30 mM. In certain embodiments, the reducing agent (such as glutathione) is added to the combined culture medium to achieve a final concentration of less than 20 mM. In certain embodiments, the reducing agent (such as glutathione) is added to the combined culture medium to achieve a final concentration of no more than 20 mM.

In certain embodiments of the methods, the first host cell is a stable cell line. In certain embodiments, the second host cell is a stable cell line. In certain embodiments, the first host cell is a CHO cell. In certain embodiments, the second host cell is a CHO cell. In certain embodiments wherein the first host cell and the second host cell are grown in the same culture, the ratio of the first host cell and the second host cell at the starting time of the combined culture is about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1 or about 10:1.

As used herein, "molar ratio" refers to the ratio of the first hinge-containing polypeptide associated with the first light chain (such as a first half-antibody) that has been expressed and/or secreted to the second hinge-containing polypeptide associated with the second light chain (such as a second half-antibody) that has been expressed and/or secreted. In some embodiments, the molar ratio of the first hinge-containing polypeptide associated with the first light chain and the second hinge-containing polypeptide associated with the second light chain is between about 1.5, about 1:4, about 1:3, about 1:2, about 1:1, about 2:1, about 3:1, about 4:1, or about 5:1, including any range in between these values. In some embodiments, the molar ratio of the first hinge-containing polypeptide associated with the first light chain and the second hinge-containing polypeptide associated with the second light chain is about 1:1. In some embodiments, the molar ratio of the first half-antibody and the second half-antibody is between about 1.5, about 1:4, about 1:3, about 1:2, about 1:1, about 2:1, about 3:1, about 4:1, or about 5:1, including any range in between these values. In some embodiments, the molar ratio of the first half-antibody and the second half-antibody is about 1:1.

III. Heteromultimeric Proteins

Also provided by the invention are heteromultimeric proteins produced by any one of the methods described herein. In certain embodiments the heteromultimeric protein comprises an antibody Fc region or a variant thereof (such as a variant with altered ADCC function). In certain embodiments, the heteromultimeric protein comprises a significant portion of an antibody Fc region or a variant thereof (e.g., a variant with altered ADCC function). In certain embodiments, the heteromultimeric protein comprises a heavy chain comprising only a portion of the $C_H1$, $C_H2$, and/or $C_H3$ domains. In certain embodiments, the heteromultimeric protein is an antibody fragment comprising only a portion of the $C_H1$, $C_H2$, and/or $C_H3$ domains. In certain embodiments, the heteromultimeric protein is an antibody. In certain embodiments, the heteromultimeric protein is a bispecific antibody. In certain embodiments, the heteromultimeric protein is a humanized antibody. In certain embodiments, the heteromultimeric protein is a human antibody. In certain embodiments, the antibody is an IgG (such as an IgG1, IgG2, or IgG4), an IgA, or an IgD. In certain embodiments, the first light chain and the second light chain of the heteromultimeric protein comprise different variable domain sequences. In certain embodiments, the first and second hinge-containing polypeptides of the heteromultimeric protein produced by the methods provided herein comprise an Fc region or a variant thereof. In certain embodiments, the first and second hinge-containing polypeptides of the heteromultimeric protein comprise an antibody heavy chain.

Heteromultimerization Domains

The heteromultimeric proteins comprise a heteromultimerization domain. To generate a substantially homogeneous population of heterodimeric molecule, the heterodimerization domain must have a strong preference for forming heterodimers over homodimers. Although the heteromultimeric proteins exemplified herein use the knobs into holes technology to facilitate heteromultimerization those skilled in the art will appreciate other heteromultimerization domains useful in the instant invention.

Knobs into Holes

The use of knobs into holes as a method of producing multispecific antibodies is well known in the art. See U.S. Pat. No. 5,731,168 granted 24 Mar. 1998 assigned to Genentech, PCT Pub. No. WO2009089004 published 16 Jul. 2009 and assigned to Amgen, and US Pat. Pub. No. 20090182127 published 16 Jul. 2009 and assigned to Novo Nordisk A/S. See also Marvin and Zhu, Acta Pharmacologica Sincia (2005) 26(6):649-658 and Kontermann (2005) Acta Pharacol. Sin., 26:1-9. A brief discussion is provided here.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g. by altering nucleic acid encoding the interface). Normally, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The upper limit for the number of original residues which are replaced is the total number of residues in the interface of the first polypeptide. The side chain volumes of the various amino residues are shown in Table 1 below:

TABLE 1

Properties of Amino Acid Residues

| Amino Acid | One-Letter Abbreviation | MASS[a] (daltons) | VOLUME[b] (Angstrom$^3$) | Accessible Surface Area[c] (Angstrom$^2$) |
|---|---|---|---|---|
| Alanine (Ala) | A | 71.08 | 88.6 | 115 |
| Arginine (Arg) | R | 156.20 | 173.4 | 225 |
| Asparagine (Asn) | N | 114.11 | 117.7 | 160 |
| Aspartic acid (Asp) | D | 115.09 | 111.1 | 150 |
| Cysteine (Cys) | C | 103.14 | 108.5 | 135 |
| Glutamine (Gln) | Q | 128.14 | 143.9 | 180 |
| Glutamic acid (Glu) | E | 129.12 | 138.4 | 190 |
| Glycine (Gly) | G | 57.06 | 60.1 | 75 |
| Histidine (His) | H | 137.15 | 153.2 | 195 |
| Isoleucine (Ile) | I | 113.17 | 166.7 | 175 |
| Leucine (Leu) | L | 113.17 | 166.7 | 170 |
| Lysine (Lys) | K | 128.18 | 168.6 | 200 |
| Methionine (Met) | M | 131.21 | 162.9 | 185 |
| Phenylalinine (Phe) | F | 147.18 | 189.9 | 210 |
| Proline (Pro) | P | 97.12 | 122.7 | 145 |
| Serine (Ser) | S | 87.08 | 89.0 | 115 |
| Threonine (Thr) | T | 101.11 | 116.1 | 140 |
| Tryptophan (Trp) | W | 186.21 | 227.8 | 255 |
| Tyrosine (Tyr) | Y | 163.18 | 193.6 | 230 |
| Valine (Val) | V | 99.14 | 140.0 | 155 |

[a]Molecular weight amino acid minus that of water. Values from *Handbook of Chemistry and Physics*, 43rd ed. Cleveland, Chemical Rubber Publishing Co., 1961.
[b]Values from A.A. Zamyatnin, *Prog. Biophys. Mol. Biol.* 24:107-123, 1972.
[c]Values from C. Chothia, *J. Mol. Biol.* 105:1-14, 1975. The accessible surface area is defined in Figures 6-20 of this reference.

The preferred import residues for the formation of a protuberance are generally naturally occurring amino acid residues and are preferably selected from arginine (R), phenylalanine (F), tyrosine (Y) and tryptophan (W). Most preferred are tryptophan and tyrosine. In one embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). Normally, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. The upper limit for the number of original residues which are replaced is the total number of residues in the interface of the second polypeptide. The side chain volumes of the various amino residues are shown in Table 1 above.

The preferred import residues for the formation of a cavity are usually naturally occurring amino acid residues and are preferably selected from alanine (A), serine (S), threonine (T) and valine (V). Most preferred are serine, alanine or threonine. In one embodiment, the original residue for the formation of the cavity has a large side chain volume, such as tyrosine, arginine, phenylalanine or tryptophan.

An "original" amino acid residue is one which is replaced by an "import" residue which can have a smaller or larger side chain volume than the original residue. The import amino acid residue can be a naturally occurring or non-naturally occurring amino acid residue, but preferably is the former. "Naturally occurring" amino acid residues are those residues encoded by the genetic code and listed in Table 1 above. By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, ornithine, norvaline, homoserine and other amino acid residue analogues such as those described in Ellman et al., *Meth. Enzym.* 202:301-336 (1991), for example. To generate such non-naturally occurring amino acid residues, the procedures of Noren et al. *Science* 244: 182 (1989) and Ellman et al., supra can be used. Briefly, this involves chemically activating a suppressor tRNA with a non-naturally occurring amino acid residue followed by in vitro transcription and translation of the RNA. The method of the instant invention involves replacing at least one original amino acid residue, but more than one original residue can be replaced. Normally, no more than the total residues in the interface of the first or second polypeptide will comprise original amino acid residues which are replaced. Typically, original residues for replacement are "buried". By "buried" is meant that the residue is essentially inaccessible to solvent. Generally, the import residue is not cysteine to prevent possible oxidation or mispairing of disulfide bonds.

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity relies on modeling the protuberance/cavity pair based upon a three-dimensional structure such as that obtained by X-ray crystallography or nuclear magnetic resonance (NMR). This can be achieved using widely accepted techniques in the art. By "original or template nucleic acid" is meant the nucleic acid encoding a polypeptide of interest which can be "altered" (i.e. genetically engineered or mutated) to encode a protuberance or cavity. The original or starting nucleic acid may be a naturally occurring nucleic acid or may comprise a nucleic acid which has been subjected to prior alteration (e.g. a humanized antibody fragment). By "altering" the nucleic acid is meant that the original nucleic acid is mutated by inserting, deleting or replacing at least one codon encoding an amino acid residue of interest. Normally, a codon encoding an original residue is replaced by a codon encoding an import residue. Techniques for genetically modifying a DNA in this manner have been reviewed in *Mutagenesis: a Practical Approach*, M. J. McPherson, Ed., (IRL Press, Oxford, UK. (1991), and include site-directed mutagenesis, cassette mutagenesis and polymerase chain reaction (PCR) mutagenesis, for example. By mutating an original/template nucleic acid, an original/template polypeptide encoded by the original/template nucleic acid is thus correspondingly altered.

The protuberance or cavity can be "introduced" into the interface of a first or second polypeptide by synthetic means, e.g. by recombinant techniques, in vitro peptide synthesis, those techniques for introducing non-naturally occurring amino acid residues previously described, by enzymatic or chemical coupling of peptides or some combination of these techniques. Accordingly, the protuberance or cavity which is "introduced" is "non-naturally occurring" or "non-native", which means that it does not exist in nature or in the original polypeptide (e.g. a humanized monoclonal antibody).

Generally, the import amino acid residue for forming the protuberance has a relatively small number of "rotamers" (e.g. about 3-6). A "rotomer" is an energetically favorable conformation of an amino acid side chain. The number of rotomers of the various amino acid residues are reviewed in Ponders and Richards, *J. Mol. Biol.* 193: 775-791 (1987).

In some embodiments of the methods provided herein, the first heterodimerization domain of the heteromultimeric protein comprises a knob modification at the interface, and the second heterodimerization domain comprises a hole modification. In certain embodiments, the knob modification comprises substituting an original amino acid residue from the first heterodimerization domain with an amino acid residue with a larger side chain than the original amino acid reside. In certain embodiments, the substituting amino acid residue with the larger side chain is a tryptophan, a phenylalanine, a tyrosine, or an arginine. In certain embodiments, the knob modification comprises T366W substitution (EU numbering). In certain embodiments, the hole modification comprises substituting an amino acid residue from the second heteromultimerization domain with an amino acid residue having a smaller side chain. In certain embodiments, the substituting amino acid having the smaller side chain is a serine, threonine, valine, or alanine. In some embodiments, the hole modification comprises two or more amino acid substitutions comprising T366S, L368A, and/or Y407V (EU numbering).

IV. Vectors, Host Cells and Recombinant Methods

For recombinant production of a heteromultimeric protein (e.g., an antibody) of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, host cells are of mammalian origin. It will be appreciated that constant regions of any isotype can be used for this purpose, including IgG, IgM, IgA, IgD, and IgE constant regions, and that such constant regions can be obtained from any human or animal species.

a. Generating Heteromultimeric Proteins Using Mammalian Host Cells:

The vector components generally include, but are not limited to, one or more of the following: a signal sequence, an origin of replication, one or more marker genes, an enhancer element, a promoter, and a transcription termination sequence.

i. Signal Sequence Component

A vector for use in a mammalian host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available. The DNA for such precursor region is ligated in reading frame to DNA encoding the desired heteromultimeric protein(s) (e.g., antibodies).

ii. Origin of Replication

Generally, an origin of replication component is not needed for mammalian expression vectors. For example, the SV40 origin may typically be used, but only because it contains the early promoter.

iii. Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See, for example, U.S. Pat. No. 4,965,199.

iv. Promoter Component

Expression and cloning vectors usually contain a promoter that is recognized by the host organism and is operably linked to the desired hinge-containing polypeptide(s) nucleic acid. Promoter sequences are known for mammalian cells. Virtually all mammalian genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most mammalian genes is an AATAAA sequence that may be the signal for addition of the poly A tail to the 3' end of the coding sequence. All of these sequences are suitably inserted into mammalian expression vectors.

Desired hinge-containing polypeptide(s) transcription and light chain(s) transcription from vectors in mammalian host cells is controlled, for example, by promoters obtained from the genomes of viruses such as, for example, polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

v. Enhancer Element Component

Transcription of DNA encoding the desired hinge-containing polypeptide(s) and light chain(s) by mammalian host cells can be increased by inserting an enhancer sequence into the vector. Many enhancer sequences are now known from mammalian genes (e.g., globin, elastase, albumin, α-fetoprotein, and insulin genes). Also, one may use an enhancer from a mammalian cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) for a description of elements for enhancing activation of eukaryotic promoters. The enhancer may be spliced into the vector at a position 5' or 3' to the antibody polypeptide-encoding sequence, provided that enhancement is achieved, but is generally located at a site 5' from the promoter.

vi. Transcription Termination Component

Expression vectors used in mammalian host cells will typically also contain sequences necessary for the termination of transcription and for stabilizing the mRNA. Such sequences are commonly available from the 5' and, occasionally 3', untranslated regions of mammalian or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

vii. Selection and Transformation of Host Cells

Suitable host cells for cloning or expressing the DNA in the vectors herein include mammalian cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for desired hinge-containing polypeptide(s) and light chain(s) production and cultured in conventional nutrient media modified as appropriate for inducing promoters, selecting transformants, or amplifying the genes encoding the desired sequences. In some embodiments, the host cell is a stably transfected host cell. In certain embodiments, the host cell is a stable cell line.

viii. Culturing the Host Cells

The host cells used to produce a desired hinge-containing polypeptide(s) and light chain(s) of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. No. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

ix. Purification of Heteromultimeric Proteins

When using recombinant techniques, the hinge-containing polypeptides associated with light chain polypeptides can be produced intracellularly, or directly secreted into the medium. If the hinge-containing polypeptide and light chain polypeptide is produced intracellularly, as a first step, the particulate debris, either host cells or lysed fragments, are removed, for example, by centrifugation or ultrafiltration. Where the hinge-containing polypeptide associated with the light chain polypeptide is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The heteromultimer composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt). The production of the heteromultimeric proteins can alternatively or additionally (to any of the foregoing particular methods) comprise dialyzing a solution comprising a mixture of the polypeptides.

V. Heteromultimeric Protein Formation/Assembly

The formation of the complete heteromultimeric protein involves the reassembly of the first hinge-containing polypeptide, the first light chain, the second hinge-containing polypeptide, and the second light chain by disulfide bond formation which in the present invention is referred to as refolding. Refolding includes the association of the first hinge-containing polypeptide with the second hinge-containing polypeptide and the formation of the interchain disulfide bonds, e.g., to form a bispecific antibody. Thus, in some embodiments of the methods provided herein, the interchain disulfide bond of the heteromultimeric protein is between hinge regions of the first and second hinge-containing polypeptides. Refolding, also termed renaturing, in the present invention is done in vitro.

Once the hinge-containing polypeptides and associated light chains are secreted from the cell, the heteromultimerization domains will drive the association of the heteromultimeric proteins. Inter-chain disulfide formation of the associated hinge-containing polypeptides proceeds. The resultant disulfide linked heteromultimeric protein is then purified. Optionally, it may be formulated for research, diagnostic, therapeutic or other purposes.

VI. Target Molecules

Examples of molecules that may be targeted by a heteromultimeric protein of this invention include, but are not limited to, soluble serum proteins and their receptors and other membrane bound proteins (e.g., adhesins).

In another embodiment the heteromultimeric protein of the invention is capable of binding one, two or more cytokines, cytokine-related proteins, and cytokine receptors selected from the group consisting of BMPI, BMP2, BMP3B (GDFIO), BMP4, BMP6, BMP8, CSFI (M-CSF), CSF2 (GM-CSF), CSF3 (G-CSF), EPO, FGFI (aFGF), FGF2 (bFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, IGF1, IGF2, IFNAI, IFNA2, IFNA4, IFNA5, IFNA6, IFNA7, IFNBI, IFNG, IFNWI, FELI, FELI (EPSELON), FELI (ZETA), IL1A, IL1B, IL2, IL3, IL4, IL5, IL6, IL7, IL8, IL9, IL10, IL11, IL12A, IL12B, IL13, IL14, IL15, IL16, IL17, IL17B, IL18, IL19, IL20, IL22, IL23, IL24, IL25, IL26, IL27, IL28A, IL28B, IL29, IL30, PDGFA, PDGFB, TGFA, TGFB1, TGFB2, TGFB3, LTA (TNF-b), LTB, TNF (TNF-α), TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TNFSFI0 (TRAIL), TNFSF11 (TRANCE), TNFSF12 (APO3L), TNFSF13 (April), TNFSF13B, TNFSF14 (HVEM-L), TNFSF15 (VEGI), TNFSF18, HGF (VEGFD), VEGF, VEGFB, VEGFC, ILIR1, IL1R2, IL1RL1, LL1RL2, IL2RA, IL2RB, IL2RG, IL3RA, IL4R, IL5RA, IL6R, IL7R, IL8RA, IL8RB, IL9R, ILI0RA, ILI0RB, IL11RA, IL12RB1, IL12RB2, IL13RA1, IL13RA2, IL15RA, IL17R, IL18R1, IL20RA, IL21R, IL22R, IL1HY1, IL1RAP, IL1RAPL1, IL1RAPL2, URN, IL6ST, IL18BP, IL18RAP, IL22RA2, AIFI, HGF, LEP (leptin), PTN, and THPO.

In another embodiment, a target molecule is a chemokine, chemokine receptor, or a chemokine-related protein selected from the group consisting of CCLI (I-309), CCL2 (MCP-1/MCAF), CCL3 (MIP-Ia), CCL4 (MIP-Ib), CCL5 (RANTES), CCL7 (MCP-3), CCL8 (mcp-2), CCLH (eotaxin), CCL13 (MCP-4), CCL15 (MIP-Id), CCL16 (HCC-4), CCL17 (TARC), CCL18 (PARC), CCL19 (MDP-3b), CCL20 (MIP-3a), CCL21 (SLC/exodus-2), CCL22 (MDC/STC-I), CCL23 (MPIF-I), CCL24 (MPIF-2/eotaxin-2), CCL25 (TECK), CCL26 (eotaxin-3), CCL27 (CTACK/ILC), CCL28, CXCLI (GROI), CXCL2 (GRO2), CXCL3 (GR03), CXCL5 (ENA-78), CXCL6 (GCP-2), CXCL9 (MIG), CXCL10 (IP 10), CXCL11 (I-TAC), CXCL12 (SDFI), CXCL13, CXCL14, CXCL16, PF4 (CXCL4), PPBP (CXCL7), CX3CL1 (SCYDI), SCYEI, XCLI (lymphotactin), XCL2 (SCM-Ib), BLRI (MDR15), CCBP2 (D6/JAB61), CCRI (CKRI/HM145), CCR2 (mcp-IRB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBII), CCR8 (CMKBR8/TERI/CKR-LI), CCR9 (GPR-9-6), CCRLI (VSHKI), CCRL2 (L-CCR), XCRI (GPR5/CCXCRI), CMKLRI, CMKORI (RDCI), CX3CR1 (V28), CXCR4, GPR2 (CCRIO), GPR31, GPR81 (FKSG80), CXCR3 (GPR9/CKR-L2), CXCR6 (TYMSTR/STRL33/Bonzo), HM74, IL8RA (IL8Ra), IL8RB (IL8Rb), LTB4R (GPR16), TCPIO, CKLFSF2, CKLFSF3, CKLFSF4, CKLFSF5, CKLFSF6, CKLFSF7, CKLFSF8, BDNF, C5R1, CSF3, GRCCIO (CIO), EPO, FY (DARC), GDF5, HDFIA, DL8, PRL, RGS3, RGS13, SDF2, SLIT2, TLR2, TLR4, TREMI, TREM2, and VHL.

In another embodiment the heteromultimeric proteins of the invention are capable of binding one or more targets selected from the group consisting of ABCFI; ACVRI; ACVRIB; ACVR2; ACVR2B; ACVRLI; ADORA2A; Aggrecan; AGR2; AICDA; AIFI; AIGI; AKAPI; AKAP2; AMH; AMHR2; ANGPTI; ANGPT2; ANGPTL3;

ANGPTL4; ANPEP; APC; APOCI; AR; AZGPI (zinc-a-glycoprotein); B7.1; B7.2; BAD; BAFF (BLys); BAGI; BAII; BCL2; BCL6; BDNF; BLNK; BLRI (MDR15); BMPI; BMP2; BMP3B (GDFIO); BMP4; BMP6; BMP8; BMPRIA; BMPRIB; BMPR2; BPAGI (plectin); BRCAI; C19orflO (IL27w); C3; C4A; C5; C5R1; CANTI; CASP1; CASP4; CAVI; CCBP2 (D6/JAB61); CCLI (1-309); CCLII (eotaxin); CCL13 (MCP-4); CCL15 (MIP-Id); CCL16 (HCC-4); CCL17 (TARC); CCL18 (PARC); CCL19 (MIP-3b); CCL2 (MCP-1); MCAF; CCL20 (MIP-3a); CCL21 (MTP-2); SLC; exodus-2; CCL22 (MDC/STC-I); CCL23 (MPIF-1); CCL24 (MPIF-2/eotaxin-2); CCL25 (TECK); CCL26 (eotaxin-3); CCL27 (CTACK/ILC); CCL28; CCL3 (MTP-Ia); CCL4 (MDP-Ib); CCL5 (RANTES); CCL7 (MCP-3); CCL8 (mcp-2); CCNAI; CCNA2; CCNDI; CCNEI; CCNE2; CCRI (CKRI/HM145); CCR2 (mcp-IRB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBII); CCR8 (CMKBR8/TERI/CKR-L1); CCR9 (GPR-9-6); CCRLI (VSHKI); CCRL2 (L-CCR); CD164; CD19; CDIC; CD20; CD200; CD22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDHI (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKNIA (p21Wapl/Cipl); CDKNIB (p27Kipl); CDKNIC; CDKN2A (P16INK4a); CDKN2B; CDKN2C; CDKN3; CEBPB; CERI; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLRI; CMKORI (RDCI); CNRI; COL18A1; COLIAI; COL4A3; COL6A1; CR2; CRP; CSFI (M-CSF); CSF2 (GM-CSF); CSF3 (GCSF); CTLA4; CTNNBI (b-catenin); CTSB (cathepsin B); CX3CL1 (SCYDI); CX3CR1 (V28); CXCLI (GROI); CXCL10 (IP-10); CXCLII (I-TAC/IP-9); CXCL12 (SDFI); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYCI; CYSLTRI; DAB2IP; DES; DKFZp451J0118; DNCLI; DPP4; E2F1; ECGFI; EDGI; EFNAI; EFNA3; EFNB2; EGF; EGFR; ELAC2; ENG; ENO1; ENO2; ENO3; EPHB4; EPO; ERBB2 (Her-2); EREG; ERK8; ESRI; ESR2; F3 (TF); FADD; FasL; FASN; FCERIA; FCER2; FCGR3A; FGF; FGFI (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FELI (EPSILON); FILI (ZETA); FLJ12584; FLJ25530; FLRTI (fibronectin); FLTI; FOS; FOSLI (FRA-I); FY (DARC); GABRP (GABAa); GAGEBI; GAGECI; GALNAC4S-65T; GATA3; GDF5; GFI1; GGT1; GM-CSF; GNASI; GNRHI; GPR2 (CCRIO); GPR31; GPR44; GPR81 (FKSG80); GRC-CIO (CIO); GRP; GSN (Gelsolin); GSTPI; HAVCR2; HDAC4; HDAC5; HDAC7A; HDAC9; HGF; HIFIA; HDPI; histamine and histamine receptors; HLA-A; HLA-DRA; HM74; HMOXI; HUMCYT2A; ICEBERG; ICOSL; ID2; IFN-a; IFNAI; IFNA2; IFNA4; IFNA5; IFNA6; IFNA7; IFNB1; IFNgamma; DFNWI; IGBPI; IGFI; IGFIR; IGF2; IGFBP2; IGFBP3; IGFBP6; IL-I; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; IL1A; IL1B; ILIF10; IL1F5; IL1F6; IL1F7; IL1F8; IL1F9; IL1HYI; IL1 RI; IL1R2; IL1RAP; IL1RAPL1; IL1RAPL2; IL1RL1; IL1RL2, ILIRN; IL2; IL20; IL20RA; IL21R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); EL7; EL7R; EL8; IL8RA; DL8RB; IL8RB; DL9; DL9R; DLK; INHA; INHBA; INSL3; INSL4; IRAKI; ERAK2; ITGAI; ITGA2; ITGA3; ITGA6 (a6 integrin); ITGAV; ITGB3; ITGB4 (b 4 integrin); JAGI; JAKI; JAK3; JUN; K6HF; KAII; KDR; KITLG; KLF5 (GC Box BP); KLF6; KLKIO; KLK12; KLK13; KLK14; KLK15; KLK3; KLK4; KLK5; KLK6; KLK9; KRT1; KRT19 (Keratin 19); KRT2A; KHTHB6 (hair-specific type H keratin); LAMAS; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIBI; midkine; MEF; MIP-2; MKI67; (Ki-67); MMP2; MMP9; MS4A1; MSMB; MT3 (metallothionectin-III); MTSSI; MUCI (mucin); MYC; MYD88; NCK2; neurocan; NFKBI; NFKB2; NGFB (NGF); NGFR; NgR-Lingo; NgR-Nogo66 (Nogo); NgR-p75; NgR-Troy; NMEI (NM23A); NOX5; NPPB; NROBI; NROB2; NRIDI; NR1D2; NR1H2; NR1H3; NR1H4; NR1I2; NR1I3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRPI; NRP2; NT5E; NTN4; ODZI; OPRDI; P2RX7; PAP; PARTI; PATE; PAWR; PCA3; PCNA; PDGFA; PDGFB; PECAMI; PF4 (CXCL4); PGF; PGR; phosphacan; PIAS2; PIK3CG; PLAU (uPA); PLG; PLXDCI; PPBP (CXCL7); PPID; PRI; PRKCQ; PRKDI; PRL; PROC; PROK2; PSAP; PSCA; PTAFR; PTEN; PTGS2 (COX-2); PTN; RAC2 (p21Rac2); RARB; RGSI; RGS13; RGS3; RNFIIO (ZNF144); ROBO2; S100A2; SCGB1D2 (lipophilin B); SCGB2A1 (mammaglobin2); SCGB2A2 (mammaglobin 1); SCYEI (endothelial Monocyte-activating cytokine); SDF2; SERPINAI; SERPINA3; SERP1NB5 (maspin); SERPINEI (PAI-I); SERPDMF1; SHBG; SLA2; SLC2A2; SLC33A1; SLC43A1; SLIT2; SPPI; SPRRIB (Sprl); ST6GAL1; STABI; STATE; STEAP; STEAP2; TB4R2; TBX21; TCPIO; TDGFI; TEK; TGFA; TGFBI; TGFBIII; TGFB2; TGFB3; TGFBI; TGFBRI; TGFBR2; TGFBR3; THIL; THBSI (thrombospondin-1); THBS2; THBS4; THPO; TIE (Tie-1); TMP3; tissue factor; TLRIO; TLR2; TLR3; TLR4; TLR5; TLR6; TLR7; TLR8; TLR9; TNF; TNF-α; TNFAEP2 (B94); TNFAIP3; TNFRS-FIIA; TNFRSFIA; TNFRSFIB; TNFRSF21; TNFRSF5; TNFRSF6 (Fas); TNFRSF7; TNFRSF8; TNFRSF9; TNFS-FIO (TRAIL); TNFSFI 1 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1BB ligand); TOLLIP; Toll-like receptors; TOP2A (topoisomerase Ea); TP53; TPMI; TPM2; TRADD; TRAFI; TRAF2; TRAF3; TRAF4; TRAF5; TRAF6; TREMI; TREM2; TRPC6; TSLP; TWEAK; VEGF; VEGFB; VEGFC; versican; VHL C5; VLA-4; XCLI (lymphotactin); XCL2 (SCM-Ib); XCRI (GPR5/CCXCRI); YYI; and ZFPM2.

Preferred molecular target molecules for antibodies encompassed by the present invention include CD proteins such as CD3, CD4, CD8, CD16, CD19, CD20, CD34; CD64, CD200 members of the ErbB receptor family such as the EGF receptor, HER2, HER3 or HER4 receptor; cell adhesion molecules such as LFA-1, Mac1, p150.95, VLA-4, ICAM-1, VCAM, alpha4/beta7 integrin, and alphav/beta3 integrin including either alpha or beta subunits thereof (e.g., anti-CD11a, anti-CD18 or anti-CD11b antibodies); growth factors such as VEGF-A, VEGF-C; tissue factor (TF); alpha interferon (□alphaIFN); TNFalpha, an interleukin, such as IL-1beta, IL-3, IL-4, IL-5, IL-8, IL-9, IL-13, IL17A/F, IL-18, IL-13Ralpha1, IL13Ralpha2, IL-4R, IL-5R, IL-9R, IgE; blood group antigens; flk2/flt3 receptor; obesity (OB) receptor; mpl receptor; CTLA-4; RANKL, RANK, RSV F protein, protein C etc.

In one embodiment, the heteromultimeric proteins of this invention bind low-density lipoprotein receptor-related protein (LRP)-1 or LRP-8 or transferrin receptor, and at least one target selected from the group consisting of 1) beta-secretase (BACE1 or BACE2), 2) alpha-secretase, 3) gamma-secretase, 4) tau-secretase, 5) amyloid precursor protein (APP), 6) death receptor 6 (DR6), 7) amyloid beta peptide, 8) alpha-synuclein, 9) Parkin, 10) Huntingtin, 11) p75 NTR, and 12) caspase-6.

In one embodiment, the heteromultimeric proteins of this invention binds to at least two target molecules selected from the group consisting of: IL-1alpha and IL-1beta, IL-12 and IL-18; IL-13 and IL-9; IL-13 and IL-4; IL-13 and IL-5; IL-5 and IL-4; IL-13 and IL-1beta; IL-13 and IL-25; IL-13 and TARC; IL-13 and MDC; IL-13 and MEF; IL-13 and TGF-β; IL-13 and LHR agonist; IL-12 and TWEAK, IL-13 and CL25; IL-13 and SPRR2a; IL-13 and SPRR2b; IL-13 and ADAMS, IL-13 and PED2, IL17A and IL17F, CD3 and CD19, CD138 and CD20; CD138 and CD40; CD19 and CD20; CD20 and CD3; CD38 and CD138; CD38 and CD20; CD38 and CD40; CD40 and CD20; CD-8 and IL-6; CD20 and BR3, TNFalpha and TGF-beta, TNFalpha and IL-1beta; TNFalpha and IL-2, TNF alpha and IL-3, TNFalpha and IL-4, TNFalpha and IL-5, TNFalpha and IL6, TNFalpha and IL8, TNFalpha and IL-9, TNFalpha and IL-10, TNFalpha and IL-11, TNFalpha and IL-12, TNFalpha and IL-13, TNFalpha and IL-14, TNFalpha and IL-15, TNFalpha and IL-16, TNFalpha and IL-17, TNFalpha and IL-18, TNFalpha and IL-19, TNFalpha and IL-20, TNFalpha and IL-23, TNFalpha and IFNalpha, TNFalpha and CD4, TNFalpha and VEGF, TNFalpha and MIF, TNFalpha and ICAM-1, TNFalpha and PGE4, TNFalpha and PEG2, TNFalpha and RANK ligand, TNFalpha and Te38; TNFalpha and BAFF; TNFalpha and CD22; TNFalpha and CTLA-4; TNFalpha and GP130; TNFα and IL-12p40; VEGF and HER2, VEGF-A and HER2, VEGF-A and PDGF, HER1 and HER2, VEGF-A and VEGF-C, VEGF-C and VEGF-D, HER2 and DR5, VEGF and IL-8, VEGF and MET, VEGFR and MET receptor, VEGFR and EGFR, HER2 and CD64, HER2 and CD3, HER2 and CD16, HER2 and HER3; EGFR(HER1) and HER2, EGFR and HER3, EGFR and HER4, IL-13 and CD40L, IL4 and CD40L, TNFR1 and IL-1R, TNFR1 and IL-6R and TNFR1 and IL-18R, EpCAM and CD3, MAPG and CD28, EGFR and CD64, CSPGs and RGM A; CTLA-4 and BTNO2; IGF1 and IGF2; IGF1/2 and Erb2B; MAG and RGM A; NgR and RGM A; NogoA and RGM A; OMGp and RGM A; PDL-I and CTLA-4; and RGM A and RGM B.

Soluble antigens or fragments thereof, optionally conjugated to other molecules, can be used as immunogens for generating antibodies. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells which have been transformed by recombinant techniques to express the transmembrane molecule. Other antigens and forms thereof useful for preparing antibodies will be apparent to those in the art.

VII. Activity Assays

The heteromultimeric proteins of the present invention can be characterized for their physical/chemical properties and biological functions by various assays known in the art.

The purified heteromultimeric proteins can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the immunoglobulins produced herein are analyzed for their biological activity. In some embodiments, the immunoglobulins of the present invention are tested for their antigen binding activity. The antigen binding assays that are known in the art and can be used herein include, without limitation, any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. An illustrative antigen binding assay is provided below in the Examples section.

In one embodiment, the present invention contemplates an altered antibody that possesses some but not all effector functions, which make it a desired candidate for many applications in which the half life of the antibody in vivo is important yet certain effector functions (such as complement and ADCC) are unnecessary or deleterious. In certain embodiments, the Fc activities of the produced heteromultimeric protein are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the heteromultimeric protein lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol* 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and natural killer (NK) cells. Alternatively, or additionally, ADCC activity of the molecule of interest may be assessed in vivo, e.g., in a animal model such as that disclosed in Clynes et al. *PNAS (USA)* 95:652-656 (1998). C1q binding assays may also be carried out to confirm that the antibody is unable to bind C1q and hence lacks CDC activity. To assess complement activation, a CDC assay, e.g. as described in Gazzano-Santoro et al., *J. Immunol. Methods* 202:163 (1996), may be performed. FcRn binding and in vivo clearance/half life determinations can also be performed using methods known in the art.

VIII. Conjugated Proteins

The invention also provides conjugated proteins such as conjugated antibodies or immunoconjugates (for example, "antibody-drug conjugates" or "ADC"), comprising any of the heteromultimeric proteins described herein (e.g., an antibody made according to the methods described herein) where one of the constant regions of the light chain or the heavy chain is conjugated to a chemical molecule such as a dye or cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In particular, as described herein, the use of heteromultimerization domains enables the construction of antibodies containing two different heavy chains (HC1 and HC2) as well as two different light chains (LC1 and LC2). An immunoconjugate constructed using the methods described herein may contain the cytotoxic agent conjugated to a constant region of only one of the heavy chains (HC1 or HC2) or only one of the light chains (LC1 or LC2). Also, because the immunoconjugate can have the cytotoxic agent attached to only one heavy or light chain, the amount of the cytotoxic agent being administered to a subject is reduced relative to administration of an antibody having the cytotoxic agent attached to both heavy or light chains. Reducing the amount of cytotoxic agent being administered to a subject limits adverse side effects associated with the cytotoxic agent.

The use of antibody-drug conjugates for the local delivery of cytotoxic or cytostatic agents, i.e., drugs to kill or inhibit tumor cells in the treatment of cancer (Syrigos and Epenetos, Anticancer Research 19:605-614 (1999); Niculescu-Duvaz and Springer, Adv. Drg. Del. Rev. 26:151-172 (1997); U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., Lancet (Mar. 15, 1986):603-605 (1986); Thorpe, (1985) "Antibody Carriers Of Cytotoxic Agents In Cancer Therapy: A Review," in Monoclonal Antibodies '84: Biological And Clinical Applications, A. Pinchera et al. (eds.), pp. 475-506). Maximal efficacy with minimal toxicity is sought thereby. Both polyclonal antibodies and monoclonal antibodies have been reported as useful in these strategies (Rowland et al., Cancer Immunol. Immunother. 21:183-187 (1986)). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al., Jour. of the Nat. Cancer Inst. 92(19):1573-1581 (2000); Mandler et al., Bioorganic & Med. Chem. Letters 10:1025-1028 (2000); Mandler et al., Bioconjugate Chem. 13:786-791 (2002)), maytansinoids (EP 1391213; Liu et al., Proc. Natl. Acad. Sci. USA 93:8618-8623 (1996)), and calicheamicin (Lode et al., Cancer Res. 58:2928 (1998); Hinman et al., Cancer Res. 53:3336-3342 (1993)). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein. Details regarding such small molecule toxins are provided in WO2008/021290.

i. Maytansine and Maytansinoids

In some embodiments, the immunoconjugate comprises an antibody (full length or fragments) of the invention conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. Patent Application Publication No. 2005/0169933, the disclosures of which are hereby expressly incorporated by reference. Antibody-maytansinoid conjugates comprising the linker component SMCC may be prepared as disclosed in U.S. Patent Application Publication No. 2005/0169933. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

ii. Auristatins and Dolastatins

In some embodiments, the immunoconjugate comprises an antibody of the invention conjugated to dolastatins or dolostatin peptidic analogs and derivatives, the auristatins (U.S. Pat. Nos. 5,635,483 and 5,780,588). Dolastatins and auristatins have been shown to interfere with microtubule dynamics, GTP hydrolysis, and nuclear and cellular division (Woyke et al., Antimicrob. Agents and Chemother. 45(12): 3580-3584 (2001)) and have anticancer (U.S. Pat. No. 5,663,149) and antifungal activity (Pettit et al., Antimicrob. Agents Chemother. 42:2961-2965 (1998)). The dolastatin or auristatin drug moiety may be attached to the antibody through the N-(amino) terminus or the C-(carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands," U.S. Application Publication No. 2005/0238649, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides," volume 1, pp. 76-136, 1965, Academic Press) that is well known in the field of peptide chemistry. The auristatin/dolastatin drug moieties may be prepared according to the methods of: U.S. Pat. Nos. 5,635,483 and 5,780,588; Pettit et al., J. Nat. Prod. 44:482-485 (1981); Pettit et al., Anti-Cancer Drug Design 13:47-66 (1998); Poncet, Curr. Pharm. Des. 5:139-162 (1999); and Pettit, Fortschr. Chem. Org. Naturst. 70:1-79 (1997). See also Doronina, Nat. Biotechnol. 21(7):778-784 (2003); and "Monomethylvaline Compounds Capable of Conjugation to Ligands," U.S. Application Publication No. 2005/0238649, hereby incorporated by reference in its entirety (disclosing, e.g., linkers and methods of preparing monomethylvaline compounds such as MMAE and MMAF conjugated to linkers).

iii. Calicheamicin

In other embodiments, the immunoconjugate comprises an antibody of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, and 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA, which is an antifolate. Both calicheamicin and QFA have intracellular sites of action and do not readily cross the plasma membrane. Therefore, cellular uptake of these agents through antibody mediated internalization greatly enhances their cytotoxic effects.

iv. Other Cytotoxic Agents

Other antitumor agents that can be conjugated to the antibodies of the invention or made according to the methods described herein include BCNU, streptozoicin, vincristine and 5-fluorouracil, the family of agents known collectively LL-E33288 complex described in U.S. Pat. Nos. 5,053,394 and 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAP I, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes (see, for example, WO 93/21232, published Oct. 28, 1993).

The present invention further contemplates an immunoconjugate formed between an antibody and a compound with nucleolytic activity (e.g., a ribonuclease or a DNA endonuclease such as a deoxyribonuclease; DNase).

For selective destruction of a tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re_{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al., Biochem. Biophys. Res. Commun. 80:49-57 (1978)) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al. Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al, Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

v. Preparation of Conjugated Antibodies

In the conjugated antibodies of the invention, an antibody is conjugated to one or more moieties (for example, drug moieties), e.g., about 1 to about 20 moieties per antibody, optionally through a linker. The conjugated antibodies may be prepared by several routes, employing organic chemistry reactions, conditions, and reagents known to those skilled in the art, including: (1) reaction of a nucleophilic group of an antibody with a bivalent linker reagent via a covalent bond, followed by reaction with a moiety of interest; and (2) reaction of a nucleophilic group of a moiety with a bivalent linker reagent via a covalent bond, followed by reaction with the nucleophilic group of an antibody. Additional methods for preparing conjugated antibodies are described herein.

The linker reagent may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl) cyclohexane-1 carboxylate ("SMCC'), and N-Succinimidyl (4-iodo-acetyl) aminobenzoate ("SIAB"). Additional linker components are known in the art and some are described herein. See also "Monomethylvaline Compounds Capable of Conjugation to Ligands," U.S. Application Publication No. 2005/0238649, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasm in protease.

Nucleophilic groups on antibodies include, but are not limited to: (i) N-terminal amine groups, (ii) side chain amine groups, e.g., lysine, (iii) side chain thiol groups, e.g., cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e., cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Conjugated antibodies of the invention may also be produced by modification of the antibody to introduce electrophilic moieties, which can react with nucleophilic substituents on the linker reagent or drug or other moiety. The sugars of glycosylated antibodies may be oxidized, e.g., with periodate oxidizing reagents, to form aldehyde or ketone groups which may react with the amine group of linker reagents or drug or other moieties. The resulting imine Schiff base groups may form a stable linkage, or may be reduced, e.g., by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug or other moiety (Hermanson, Bioconjugate Techniques). In another embodiment, proteins containing N-terminal serine or threonine residues can react with sodium meta-periodate, resulting in production of an aldehyde in place of the first amino acid (Geoghegan and Stroh, Bioconjugate Chem. 3:138-146 (1992); U.S. Pat. No. 5,362,852). Such aldehyde can be reacted with a drug moiety or linker nucleophile.

Likewise, nucleophilic groups on a moiety (such as a drug moiety) include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate. In yet another embodiment, the antibody may be conjugated to a "receptor" (such streptavidin) for utilization in tumor pre-targeting wherein the antibody-receptor conjugate is administered to the individual, followed by removal of unbound conjugate from the circulation using a clearing agent and then administration of a "ligand" (e.g., avidin) which is conjugated to a cytotoxic agent (e.g., a radionucleotide).

IX. Utility

The present methods provided for herein find industrial applicability in the production of heteromultimeric proteins. The inventive methods reduce the amount of work involved in two separate fermentation and isolations as are technical difficulties inherent in two separate fermentations. Furthermore, elimination of the annealment and redox steps of the prior methods procedures can increase yields and decrease processing complexity and costs.

The heteromultimeric proteins described herein find use in, for example, in vitro, ex vivo and in vivo therapeutic methods. The invention provides various methods based on using one or more of these molecules. In certain pathological conditions, it is necessary and/or desirable to utilize heteromultimeric proteins, e.g., multispecific antibodies. The invention provides these heteromultimeric proteins, which can be used for a variety of purposes, for example as therapeutics, prophylactics and diagnostics. For example, the invention provides methods of treating a disease, said methods comprising administering to a subject in need of treatment a heteromultimeric protein of the invention, whereby the disease is treated. Any of the heteromultimeric proteins of the invention described herein can be used in therapeutic (or prophylactic or diagnostic) methods described herein.

For example, when the heteromultimeric protein is multivalent, a valuable benefit is the enhanced avidity they pose for their antigen. In addition to having intrinsic high affinity on a binding unit (ie, a Fab) to antigen basis, normal IgG antibodies also exploit the avidity effect to increase their association with antigens as a result of their bivalent binding towards the targets.

A heteromultimeric protein directed against two separate epitopes on the same antigen molecule may not only provide the benefit of enhanced binding avidity (because of bivalent binding), but may also acquire novel properties that are not associated with either of the parent antibodies. Thus, the heteromultimeric proteins of the invention find use in, for example, the blocking of receptor-ligand interactions.

The heteromultimeric proteins described herein also find use in the application of simultaneously blocking the signaling pathways of two targets with one molecule.

X. Therapeutic Uses

The heteromultimeric proteins such as antibodies and antibody fragments described herein (e.g., an antibody and/or fragment thereof made according to the methods described herein) may be used for therapeutic applications. For example, such heteromultimeric proteins can be used for the treatment of tumors, including pre-cancerous, non-metastatic, metastatic, and cancerous tumors (e.g., early stage cancer), for the treatment of allergic or inflammatory disorders, or for the treatment of autoimmune disease, or for the treatment of a subject at risk for developing cancer (for example, breast cancer, colorectal cancer, lung cancer, renal cell carcinoma, glioma, or ovarian cancer), an allergic or inflammatory disorder, or an autoimmune disease.

The term cancer embraces a collection of proliferative disorders, including but not limited to pre-cancerous growths, benign tumors, and malignant tumors. Benign tumors remain localized at the site of origin and do not have the capacity to infiltrate, invade, or metastasize to distant sites. Malignant tumors will invade and damage other tissues around them. They can also gain the ability to break off from where they started and spread to other parts of the body (metastasize), usually through the bloodstream or through the lymphatic system where the lymph nodes are located. Primary tumors are classified by the type of tissue from which they arise; metastatic tumors are classified by the tissue type from which the cancer cells are derived. Over time, the cells of a malignant tumor become more abnormal and appear less like normal cells. This change in the appearance of cancer cells is called the tumor grade and cancer cells are described as being well-differentiated, moderately-differentiated, poorly-differentiated, or undifferentiated. Well-differentiated cells are quite normal appearing and resemble the normal cells from which they originated.

Undifferentiated cells are cells that have become so abnormal that it is no longer possible to determine the origin of the cells.

The tumor can be a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, polymphocytic leukemia, or hairy cell leukemia), or lymphoma (e.g., non-Hodgkin's lymphoma, cutaneous T-cell lymphoma, or Hodgkin's disease). A solid tumor includes any cancer of body tissues other than blood, bone marrow, or the lymphatic system. Solid tumors can be further separated into those of epithelial cell origin and those of non-epithelial cell origin. Examples of epithelial cell solid tumors include tumors of the gastrointestinal tract, colon, breast, prostate, lung, kidney, liver, pancreas, ovary, head and neck, oral cavity, stomach, duodenum, small intestine, large intestine, anus, gall bladder, labium, nasopharynx, skin, uterus, male genital organ, urinary organs, bladder, and skin. Solid tumors of non-epithelial origin include sarcomas, brain tumors, and bone tumors.

Epithelial cancers generally evolve from a benign tumor to a preinvasive stage (e.g., carcinoma in situ), to a malignant cancer, which has penetrated the basement membrane and invaded the subepithelial stroma.

Multispecific protein complexes can also be used in these therapeutic applications, and antibodies that bind HER2 can in particular be used to treat breast cancer, colorectal cancer, lung cancer, renal cell carcinoma, glioma, or ovarian cancer.

Other subjects that are candidates for receiving compositions of this invention have, or are at risk for developing, abnormal proliferation of fibrovascular tissue, acne rosacea, acquired immune deficiency syndrome, artery occlusion, atopic keratitis, bacterial ulcers, Bechets disease, blood borne tumors, carotid obstructive disease, choroidal neovascularization, chronic inflammation, chronic retinal detachment, chronic uveitis, chronic vitritis, contact lens overwear, corneal graft rejection, corneal neovascularization, corneal graft neovascularization, Crohn's disease, Eales disease, epidemic keratoconjunctivitis, fungal ulcers, Herpes simplex infections, Herpes zoster infections, hyperviscosity syndromes, Kaposi's sarcoma, leukemia, lipid degeneration, Lyme's disease, marginal keratolysis, Mooren ulcer, Mycobacteria infections other than leprosy, myopia, ocular neovascular disease, optic pits, Osler-Weber syndrome (Osler-Weber-Rendu), osteoarthritis, Paget's disease, pars planitis, pemphigoid, phylectenulosis, polyarteritis, post-laser complications, protozoan infections, pseudoxanthoma elasticum, pterygium keratitis sicca, radial keratotomy, retinal neovascularization, retinopathy of prematurity, retrolental fibroplasias, sarcoid, scleritis, sickle cell anemia, Sogren's syndrome, solid tumors, Stargart's disease, Steven's Johnson disease, superior limbic keratitis, syphilis, systemic lupus, Terrien's marginal degeneration, toxoplasmosis, tumors of Ewing sarcoma, tumors of neuroblastoma, tumors of osteosarcoma, tumors of retinoblastoma, tumors of rhabdomyosarcoma, ulcerative colitis, vein occlusion, Vitamin A deficiency, Wegener's sarcoidosis, undesired angiogenesis associated with diabetes, parasitic diseases, abnormal wound healing, hypertrophy following surgery, injury or trauma (e.g., acute lung injury/ARDS), inhibition of hair growth, inhibition of ovulation and corpus *luteum* formation, inhibition of implantation, and inhibition of embryo development in the uterus.

Examples of allergic or inflammatory disorders or autoimmune diseases or disorders that may be treated using an antibody made according to the methods described herein include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions, allergic reaction, eczema including allergic or atopic eczema, asthma such as asthma bronchiale, bronchial asthma, and autoimmune asthma, conditions involving infiltration of T-cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barré syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal garnmopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia areata, CREST syndrome (calcinosis, Raynaud's phenomenon, esophageal dysmotility, sclerodactyly, and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemic-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to antispermatozoan antibodies, non-malignant thymoma, vitiligo, SCID and Epstein-Barr virus-associated diseases, acquired immune deficiency syndrome (AIDS), parasitic diseases such as Leishmania, toxic-shock syndrome, food poisoning, conditions involving infiltration of T-cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

In addition to therapeutic uses, the antibodies of the invention can be used for other purposes, including diagnostic methods, such as diagnostic methods for the diseases and conditions described herein.

XI. Dosages, Formulations, and Duration

The proteins of this invention will be formulated, dosed, and administered in a fashion consistent with good medical practice. Factors for consideration in this context include the particular disorder being treated, the particular mammal being treated, the clinical condition of the individual subject, the cause of the disorder, the site of delivery of the agent, the method of administration, the scheduling of administration, and other factors known to medical practitioners. The "therapeutically effective amount" of the proteins to be administered will be governed by such considerations, and is the minimum amount necessary to prevent, ameliorate, or treat a particular disorder (for example, a cancer, allergic or inflammatory disorder, or autoimmune disorder). The proteins need not be, but are optionally, formulated with one or more agents currently used to prevent or treat the disorder. The effective amount of such other agents depends on the amount of proteins present in the formulation, the type of disorder or treatment, and other factors discussed above. These are generally used in the same dosages and with administration routes as used hereinbefore or about from 1 to 99% of the heretofore employed dosages. Generally, alleviation or treatment of a cancer involves the lessening of one or more symptoms or medical problems associated with the cancer. The therapeutically effective amount of the drug can accomplish one or a combination of the following: reduce (by at least 10%, 20%, 30%, 40%, 50%, 60%, 70%, 80%, 90%, 100% or more) the number of cancer cells; reduce or inhibit the tumor size or tumor burden; inhibit (i.e., to decrease to some extent and/or stop) cancer cell infiltration into peripheral organs; reduce hormonal secretion in the case of adenomas; reduce vessel density; inhibit tumor metastasis; reduce or inhibit tumor growth; and/or relieve to some extent one or more of the symptoms associated with the cancer. In some embodiments, the proteins are used to prevent the occurrence or reoccurrence of cancer or an autoimmune disorder in the subject.

In one embodiment, the present invention can be used for increasing the duration of survival of a human subject susceptible to or diagnosed with a cancer or autoimmune disorder. Duration of survival is defined as the time from first administration of the drug to death. Duration of survival can also be measured by stratified hazard ratio (HR) of the treatment group versus control group, which represents the risk of death for a subject during the treatment.

In yet another embodiment, the treatment of the present invention significantly increases response rate in a group of human subjects susceptible to or diagnosed with a cancer who are treated with various anti-cancer therapies. Response rate is defined as the percentage of treated subjects who responded to the treatment. In one aspect, the combination treatment of the invention using proteins of this invention and surgery, radiation therapy, or one or more chemotherapeutic agents significantly increases response rate in the treated subject group compared to the group treated with surgery, radiation therapy, or chemotherapy alone, the increase having a Chi-square p-value of less than 0.005. Additional measurements of therapeutic efficacy in the treatment of cancers are described in U.S. Patent Application Publication No. 20050186208.

In certain embodiments, there is provided a composition comprising a heteromultimeric protein produced according to any of the methods described herein and a pharmaceutically acceptable carrier. Therapeutic formulations are prepared using standard methods known in the art by mixing the active ingredient having the desired degree of purity with optional physiologically acceptable carriers, excipients or stabilizers (Remington's Pharmaceutical Sciences (20$^{th}$ edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Sustained-release preparations may be prepared. Suitable examples of sustained-release preparations include semipermeable matrices of solid hydrophobic polymers containing the heteromultimeric protein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated heteromultimeric protein(s) remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The proteins described herein (e.g., a heteromultimeric protein such as a multispecific antibody made according to the methods described herein) are administered to a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration may be particularly desired if extensive side effects or toxicity is associated with antagonism to the target molecule recognized by the proteins. An ex vivo strategy can also be used for therapeutic applications. Ex vivo strategies involve transfecting or transducing cells obtained from the subject with a polynucleotide encoding a protein of this invention. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells.

In one example, the protein complex is (e.g., a heteromultimeric protein such as a multispecific antibody made according to the methods described herein) is administered locally, e.g., by direct injections, when the disorder or location of the tumor permits, and the injections can be repeated periodically. The protein complex can also be delivered systemically to the subject or directly to the tumor cells, e.g., to a tumor or a tumor bed following surgical excision of the tumor, in order to prevent or reduce local recurrence or metastasis.

XII. Articles of Manufacture

Another embodiment of the invention is an article of manufacture containing one or more heteromultimeric proteins described herein, and materials useful for the treatment or diagnosis of a disorder (for example, an autoimmune disease or cancer). The article of manufacture comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). At least one active agent in the composition is a heteromultimeric protein (e.g., an antibody or antibody fragment) of the invention. The label or package insert indicates that the composition is used for treating the particular condition. The label or package insert will further comprise instructions for administering the heteromultimeric protein composition to the subject. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In certain embodiments, the package insert indicates that the composition is used for treating breast cancer, colorectal cancer, lung cancer, renal cell carcinoma, glioma, or ovarian cancer.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials considered from a commercial and user standpoint, including other buffers, diluents, filters, needles, and syringes.

Kits are also provided that are useful for various purposes, e.g., for purification or immunoprecipitation of an antigen from cells. For isolation and purification of an antigen the kit can contain a heteromultimeric protein coupled to beads (e.g., sepharose beads). Kits can be provided which contain the heteromultimeric protein(s) for detection and quantitation of the antigen in vitro, e.g., in an ELISA or a Western blot. As with the article of manufacture, the kit comprises a container and a label or package insert on or associated with the container. The container holds a composition comprising at least one heteromultimeric protein (e.g., multispecific antibody or antibody fragment) of the invention. Additional containers may be included that contain, e.g., diluents and buffers or control antibodies. The label or package insert may provide a description of the composition as well as instructions for the intended in vitro or diagnostic use.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

In the experimental disclosure which follows, the following abbreviations apply: eq (equivalents); M (Molar); μM (micromolar); N (Normal); mol (moles); mmol (millimoles); pmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds); ADCC (antibody-dependent cellular cytotoxicity)); BsAb (bispecific antibody); $C_L$ (constant domain of light chain); $C_H$ (constant domain of heavy chain); CMC (complement-mediated cytotoxicity); Fab (antigen binding fragment); Fc (crystallized fragment); Fv (variable fragment ($V_L$+$V_H$)); EGFR (epidermal growth factor receptor); HC (heavy chain); IGFR (insulin-like growth factor receptor); LC (light chain); scFv (singlechain variable fragment ($V_L$ and $V_H$ tethered by an amino acid linker); VEGF (vascular endothelial growth factor); VEGFR2 (vascular endothelial growth factor receptor 2); $V_H$ (variable heavy domain); $V_L$ (variable light domain).

EXAMPLES

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

Example 1: Molar Ratio of Monomeric Components of a Bispecific Antibody in a Combined Cell Culture can be Controlled by Adjusting Cell:Cell Ratio The following example shows the molar ratio of knob and hole half-antibodies when two mammalian cell lines (CHO cells), each expressing either the knob half-antibody or the hole half-antibody, were grown in the same culture.

Production studies were performed to determine the production titer (i.e., the total amount of antibody produced by cells including heterodimer, homodimer and monomeric half-antibody) for each cell line. The individual cell lines were passaged every 3 or 4 days in seed train medium until production titer data on the individual cell lines became available.

The two cell lines were then grown and induced to express the knob half-antibody or hole half-antibody in separate cultures. The individual knob and hole cell line cultures were passaged in shake flask in 40 mL volume every 3 or 4 days in seed train medium. On the day the cultures were to be combined, cell count was measured via Vicell (Beckman Coulter).

The separate cultures were then combined at specific knob host cell:hole host cell ratios. The knob host cell:hole host cell ratio was calculated based on the production titer known for the individual cell lines. For each small scale production, about 40×10$^6$ cells were required. Using the Vicell count (cell/mL), it was possible to determine the volume of each cell line needed to be added to the combined culture to achieve the desired knob host cell:hole host cell ratio. The appropriate volume of each of the knob and hole cell lines was combined in new shake flask with a final volume of 40 mL in production media.

15 hours before harvest, glutathione (GSH) stock solution was prepared by dissolving GSH into 1M Arginine (pH=9.0) in 400 mM Succinic acid to a final GSH stock concentration of 250 mM. GSH stock solution was added to the production culture so that the final concentration of GSH was 15 mM. The combined culture media was then harvested, and the % knob half-antibody and % hole half-antibody for each combined culture were determined via reverse phase under reducing conditions. The % covalent bispecific antibody formed for each ratio tested was determined as described in FIG. 2.

These experiments were performed with the following knob half-antibody/hole half-antibody pairs:

anti-Target A (knob)/anti-Target B (hole)

anti-Target C (knob)/anti-Target D (hole)

anti-Target D (knob)/anti-Target C (hole)

anti-Target E (knob)/anti-Target F (hole)

The results of these experiments are provided in Table 2 below:

TABLE 2

|  | Ratio of Knob Host Cell: Hole Host Cell | | % Knob Expressed | % Hole Expressed | % Covalent Bispecific |
|---|---|---|---|---|---|
| anti-Target A (knob)/ anti-Target B (hole) | 1 | 1 | 40.0 | 60.0 | N/D* |
|  | 1.2 | 1 | 45.0 | 55.0 | 76.4 |
| anti-Target A (knob)/ anti-Target B (hole) | 3 | 1 | 37.5 | 62.5 | N/D* |
|  | 4 | 1 | 47.0 | 53.0 | 68.1 |
|  | 6 | 1 | 54.5 | 45.5 | N/D* |
| anti-Target C (knob)/ anti-Target D (hole) | 1 | 3 | 85.0 | 15.0 | 37.7 |
|  | 1 | 5 | 75.0 | 25.0 | N/D* |
|  | 1 | 7 | 40.0 | 60.0 | 93 |
| anti-Target D (knob)/ anti-Target C (hole) | 1 | 1 | 50.0 | 50.0 | 70.1 |
| anti-Target E (knob)/ anti-Target F (hole) | 1 | 2.5 | 46.0 | 54.0 | 87.2 |

*N/D = not determined

As shown in Table 2, yields of % covalent bispecific antibody were improved when the molar ratio of knob half-antibody:hole half-antibody were about or close to 1:1. The optimal molar ratio for bispecific formation would likely be determined for each specific bispecific antibody. The knob host cell:hole host cell ratio that produces a 1:1 knob half-antibody:hole half-antibody molar ratio varies with cell line and is experimentally determined.

Example 2: Varying the Timing of Addition of a Reductant and Concentration of Reductant Added During Production of Bispecific Antibody in a Combined Cell Culture The following example shows the addition of reductant during different stages of the production of a bispecific antibody comprising anti-Target A (knob) and anti-Target B (hole). Two mammalian cell lines, expressing either anti-Target A (knob) or anti-Target B (hole), were initially grown and induced to express the knob half-antibody or hole half-antibody in separate cultures, which were then combined in multiple separate production cultures to achieve a 1:1 molar ratio of anti-Target A (knob):anti-Target B (hole), as described above. GSH stock solution was added to the production cultures either 24 hours, 15 hours, or 4 hours prior to harvest to a final concentration of 2 mM, 4 mM, or 10 mM or the cultures were left untreated. The combined culture media from each of the production cultures were then harvested, and the % knob half-antibody and % hole half-antibody for each combined culture were determined via reverse phase under reducing conditions. The % covalent bispecific antibody formed for each ratio tested was determined as described in FIG. 2.

Figure 3:
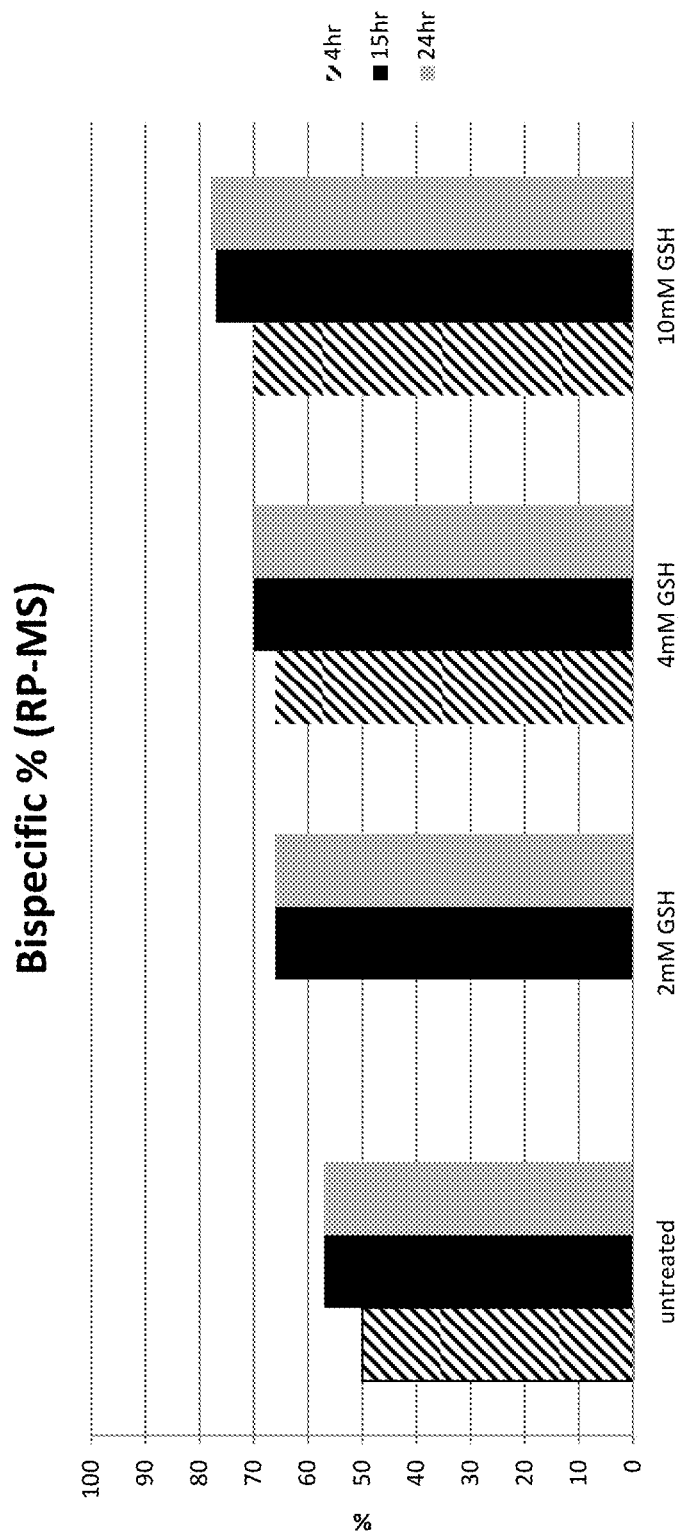
FIG. 3 shows the % bispecific antibody formed when a reductant is added to a combined cell culture comprising first mammalian host cell expressing an anti-Target A (knob) and a second mammalian host cell expression anti-Target B (hole) at 4 hours, 15 hours, or 24 hours before harvesting the combined culture medium.

As shown in FIG. 3, the yield of covalent bispecific antibody in production cultures having a final GSH concentration of 10 mM was improved compared to yield of bispecific antibody in production cultures final GSH concentration of 2 mM or 4 mM or untreated control group. The stage of production at which the GSH was added was not shown to affect the yield of covalent bispecific antibody.

In further experiments, cell lines, expressing either anti-Target A (knob) or anti-Target B (hole), were initially grown and induced to express the knob half-antibody or hole half-antibody in separate cultures, which were then combined in multiple separate production cultures to achieve either a 0.82:1 molar ratio or a 1:1 molar ratio of anti-Target A (knob):anti-Target B (hole), as described above. GSH stock solution was added to the production cultures 15 hours prior to harvest to a final concentration of 5 mM or 10 mM or untreated ("0 mM"). The cell viability of each combined cell culture was determined at harvest and the % bispecific antibody formed under each condition tested was then determined via ion exchange assay as shown in FIG. 2. The results of the experiments are shown in Table 3 below

TABLE 3

| Ratio of Knob Protein: Hole Protein | | | | | |
|---|---|---|---|---|---|
| anti-Target A (knob) | anti-Target B (hole) | [GSH] 15 Hours Pre-Harvest | % Cell Viability at Harvest | Titer (g/L)* | % Covalent Bispecific (±10%) |
| 0.82 | 1 | 0 mM | 75.8 | 2.2 | 45.9 |
|  |  | 5 mM | 76.7 | 2.3 | 70.2 |
|  |  | 10 mM | 75.3 | 2.2 | 80.4 |
| 1 | 1 | 0 mM | 81.8 | 2.2 | 39.9 |
|  |  | 5 mM | 80.9 | 2.3 | 66.7 |
|  |  | 10 mM | 79.3 | 2.3 | 72.4 |

*Titer refers to the total amount of antibody produced by the two cell lines in the combined culture, e.g., including homodimer, heterodimer, and monomeric half antibody.

As shown in Table 3, the yield of covalent bispecific antibody in production cultures having a final GSH concentration of 10 mM was improved compared to yield of bispecific antibody in production cultures final GSH concentration of 5 mM or untreated. The addition of GSH up to the combined cell culture to a final concentration of up to 10 mM was not found to affect cell viability or overall antibody production. Unwanted mixed disulfide formation or protein scrambling was not observed at 10 mM of GSH (data not shown).

Similar experiments were performed with two other mammalian cell lines, each expressing either anti-Target D (knob) or anti-Target C (hole). The two cell lines were initially grown and induced to express either anti-Target D (knob) or anti-Target C (hole) in separate cultures, which were then combined in multiple separate production cultures to achieve a 0.82:1 molar ratio of anti-Target D (knob):anti-Target C (hole), as described above. GSH stock solution was added to the production cultures 15 hours prior to harvest to a final concentration of 10 mM, 15 mM, or 20 mM or untreated ("0 mM"). The cell viability of each combined cell culture was determined at harvest, and the % bispecific antibody formed under each condition tested was then determined as shown in FIG. 2. The results of these experiments are shown in Table 4 below.

TABLE 4

| Ratio of Knob Protein: Hole Protein | | | | | |
|---|---|---|---|---|---|
| anti-Target D (knob) | anti-Target C (hole) | [GSH] 15 Hours Pre-Harvest | % Cell Viability at Harvest | Titer (g/L) | % Covalent Bispecific (±10%) |
| 1 | 1 | 0 mM | 92.0 | 1.57 | 10 |
|  |  | 10 mM | 92.7 | 1.58 | 58.9 |
|  |  | 15 mM | 89.4 | 1.55 | 61.1 |
|  |  | 20 mM | 81.6 | 1.52 | 66.2 |

*Titer refers to the total amount of antibody produced by the two cell lines in the combined culture, e.g., including homodimer, heterodimer, and monomeric half antibody that were captured by a protein A column.

As shown in Table 4, the yield of covalent bispecific antibody in production cultures having a final GSH concentration of 20 mM was improved compared to yield of bispecific antibody in production cultures final GSH concentration of 10 mM, or 15 mM or untreated. The addition of GSH up to the combined cell culture to a final concentration of up to 20 mM was found not affecting titer. When GSH was added to production cultures to a final concentration of 20 mM, however, covalent modification of half antibody by GSH was observed (data not shown).

Example 3: Yield of Bispecific Antibody Formed in Combined Culture Medium Compared to In Vitro Assembly Additional experiments were performed using anti-Target E (knob) and anti-Target F (hole) to compare yield of bispecific antibody obtained by a combined culture of mammalian host cells (e.g., CHO cells) expressing anti-Target E and mammalian cells (e.g., CHO cells) expressing anti-Target F to the yield of bispecific antibody obtained by combining in vitro purified anti-Target E (knob) and purified anti-Target F (hole) using a protein A column. Briefly, two mammalian cell lines, each expressing either anti-Target E (knob) or anti-Target F (hole), were initially grown and induced to express the knob half-antibody or hole half-antibody in separate cultures. The separate cultures are then combined and grown for an additional length of time. The combined culture medium was harvested, and the % bispecific antibody formed was then determined via a cation exchange assay as shown in FIG. 2. In parallel bispecific antibody was formed by combining purified anti-Target E (knob) and anti-Target F (hole) in vitro (see e.g., WO2013/055958). The final yield of bispecific antibody formed under both conditions was comparable (data not shown).

Example 4: Bispecific Production

Additional experiments were performed using anti-Target G (knob) and anti-Target H (hole) to test whether bispecific anti-Target G/anti-Target H antibody can be formed from a preparation of purified anti-Target G half antibody comprising anti-Target G/anti-Target G homodimer and a preparation of purified anti-Target H half antibody comprising anti-Target H/anti-Target H homodimer. Separate cultures of mammalian host cells (e.g., CHO cells) transiently expressing half antibody anti-Target G (knob) and mammalian host cells (e.g., CHO cells) transiently expressing half antibody anti-Target H (hole) were grown and harvested, as described above.

Each half antibody was captured on a 5 mL MabSURE SELECT Protein A column. The column was then washed with 10 column volumes (CV) of the following buffers: an equilibration buffer consisting of 50 mM TRIS pH 8.0, 150 mM NaCl, 0.05% Triton X-100, 0.05% Triton X-114, a wash buffer consisting of 25 mM Sodium Citrate pH 6.0. Each arm was eluted into 0.15 M Sodium Acetate pH 2.7. Identity of each half antibody was confirmed by MS.

In the case of the bispecific, each half antibody was independently titrated up to pH 5.0 using 1:10 1M TRIS arginine pH 9.0 then combined together at a ratio of 1:1. The mixture was then titrated to pH 8.5 using 1:10 1M TRIS arginine pH 9.0 and left at room temperature for 3 days following the addition of an excess of freshly prepared 0.5M reduced L-Glutathione (Sigma Aldrich) at a molar ratio of 1:200. The reaction was checked by MS for bispecific ID.

Figure 4:
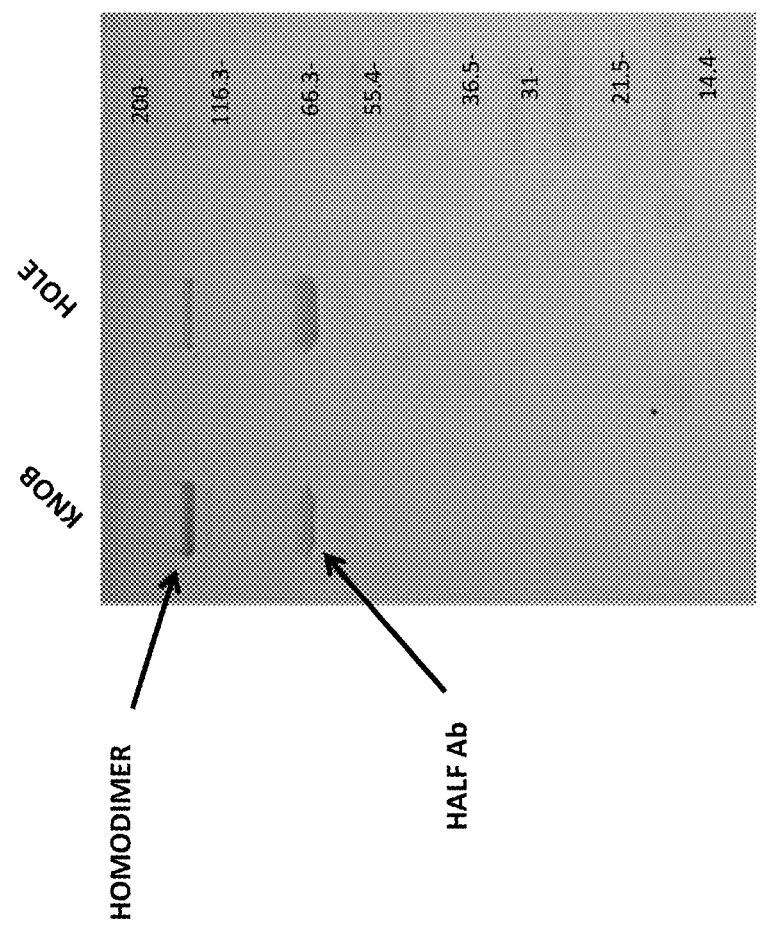
FIG. 4 shows knob and hole capture pools that were run on 4-20% Tris-Glycine SDS PAGE.
Figure 5:
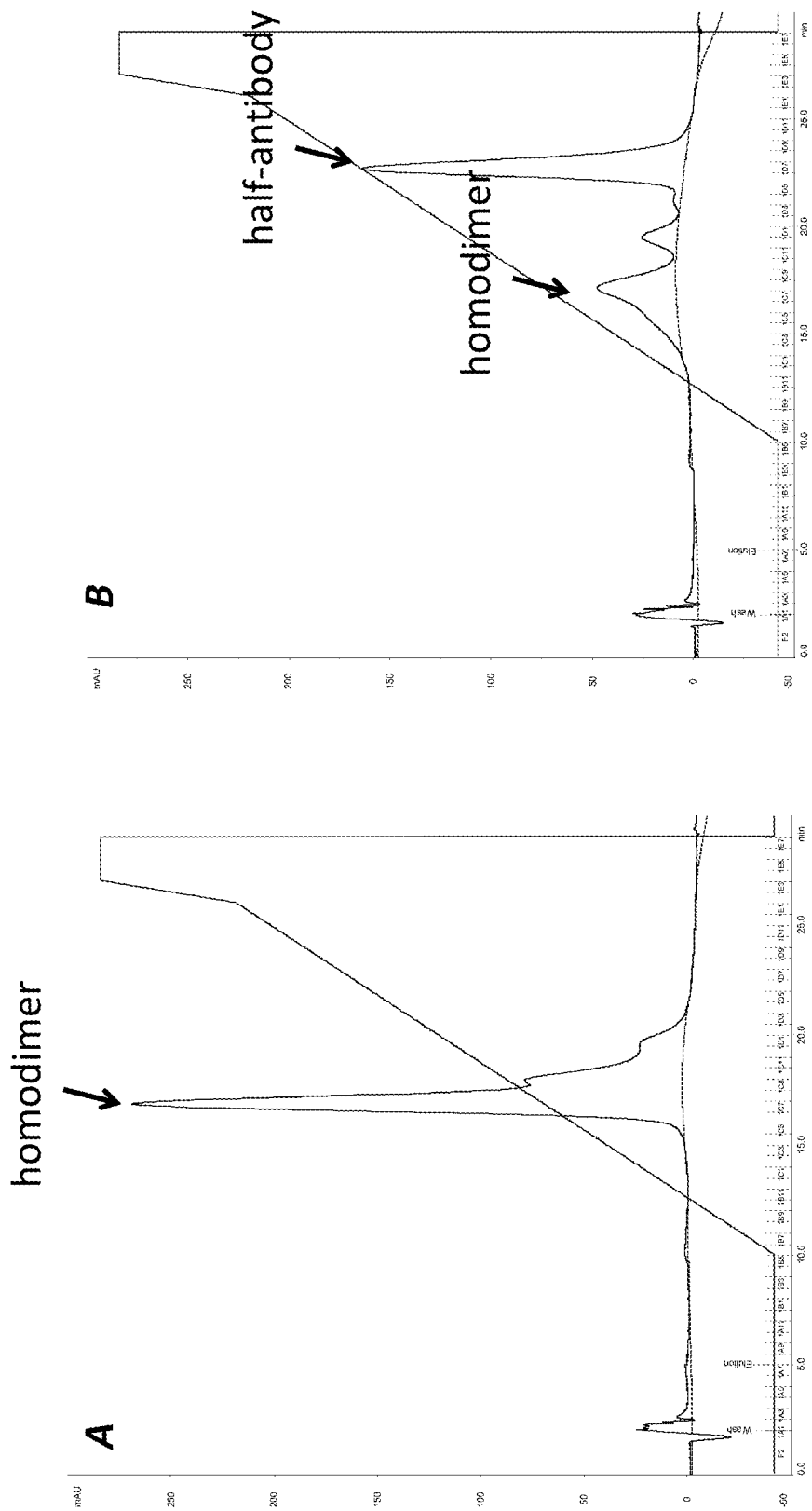
FIG. 5, panel A shows the chromatogram of samples separated based on hydrophobicity for the anti-Target G in which homodimer and half antibody co-eluted into the one broad peak.
Figure 6:
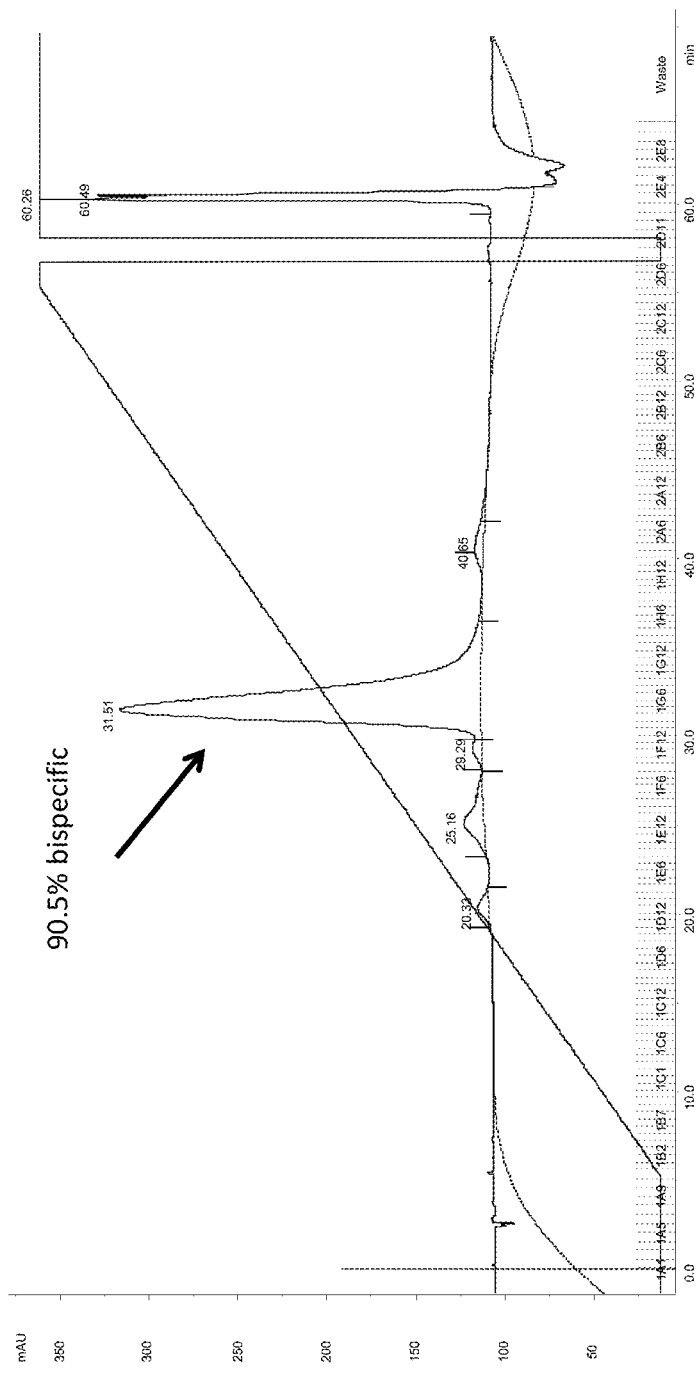
FIG. 6 shows the results of mass spectrometry for the anti-Target G/anti-Target H bispecific antibody.

Knob and hole capture pools were run on 4-20% Tris-Glycine SDS PAGE, revealing the presence of bands corresponding to the molecular weight of half antibody and homodimer in each capture pool. See FIG. 4. In addition following MabSURE SELECT capture, 0.5 mg of each was loaded onto a hydrophobicity column (2.1×100 mm). The running buffer was 25 mM Potassium Phosphate, 1M Ammonium Sulfate pH 6.5 and the elution buffer was 25 mM Potassium Phosphate pH 6.5, 25% isopropanol. The chromatograms reflected the heterogeneity seen with the gel, and also revealed differences in retention time of main peak. See FIGS. 5A and 5B, which show the chromatograms for anti-Target G (knob) and anti-Target H (hole), respectively. The amounts of homodimer and half antibody in the capture pools may vary depending on specific antibodies.

Following glutathione treatment, the bispecific was also loaded on the hydrophobicity column. The chromatogram revealed a single main peak (>90%), with retention time in between those of each half antibody. See FIG. 6. MS confirmed that the main peak was bispecific. These results suggest that there is covalent homodimer present in the half antibody capture pools, and the homodimer is able to be disrupted using the assembly conditions cited above and is available for bispecific formation.

The bispecific assembly conditions were further examined by comparing the assembly of anti-Target A (knob) and anti-Target B (hole) in combined culture medium in the absence of GSH vs. in the presence 10 mM GSH.

CHO cells were transfected using Lipofectamine 2000 according to the manufacturer's recommendation (Invitrogen, Carlsbad, Calif.). Transfected cells were selected at various concentrations of MSX (methionine sulfoximine, 25 and 50 uM). Picked colonies were evaluated for antibody production by sampling supernatant from colonies and analyzing by ELISA. To make stable pool, on the basis of ELISA titers, the top 48 clones were combined and scaled up. Individual clones were also expanded and scaled up for antibody productivity evaluation to determine the top clones.

Next, 40 L culture was used and cells were seeded at $1.2\times10^6$ cells/mL in 2.8 L of culture media. The culture was regularly split and agitated at 90 rpm and maintained at a pH set point of 7.0±0.03 and 30% dissolved oxygen ($dO_2$). 15 mM GSH was added on day 11, followed by cell harvest on day 12.

Figure 7A:
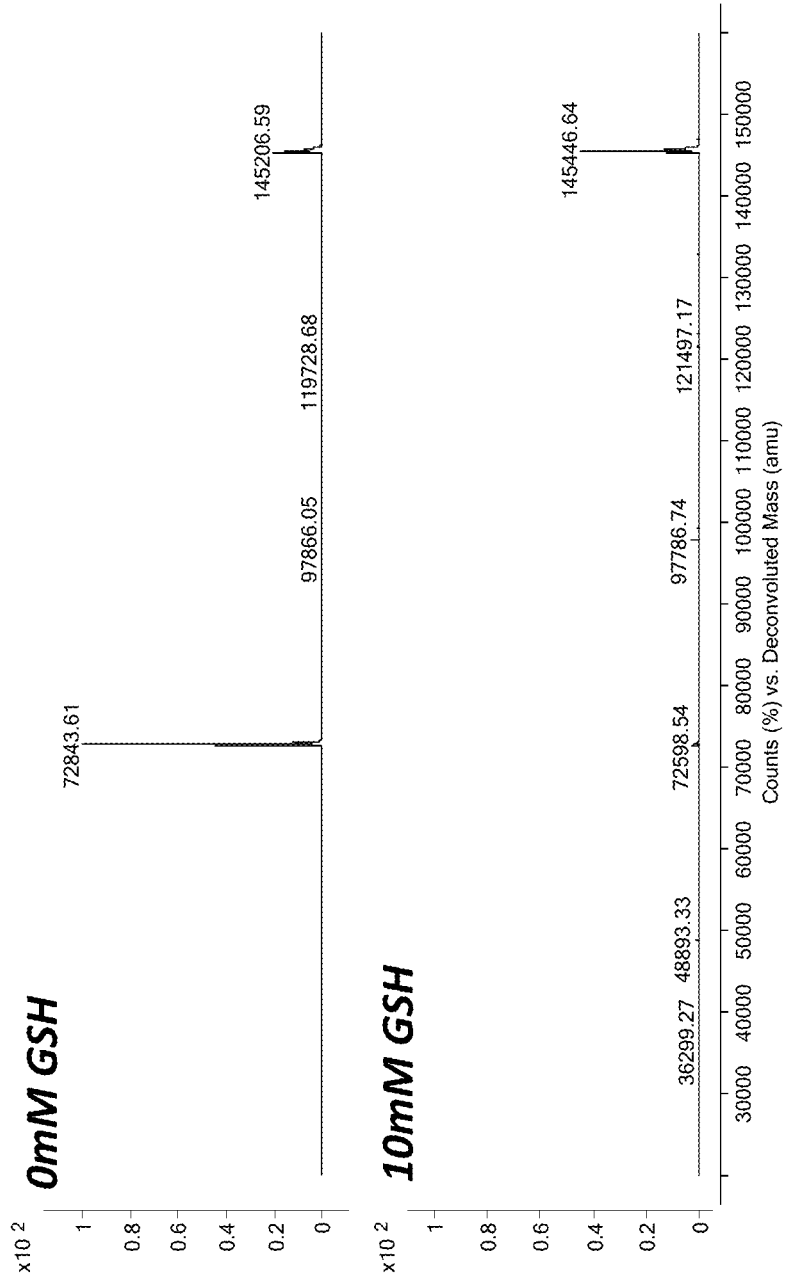
FIG. 7A shows the results of an electrospray ionization time-of-flight mass spectrometry (ESI-TOF MS) experiment performed on untreated and GSH-treated combined culture medium into which anti-Target A and anti-Target B half antibodies were secreted.
Figure 7C:
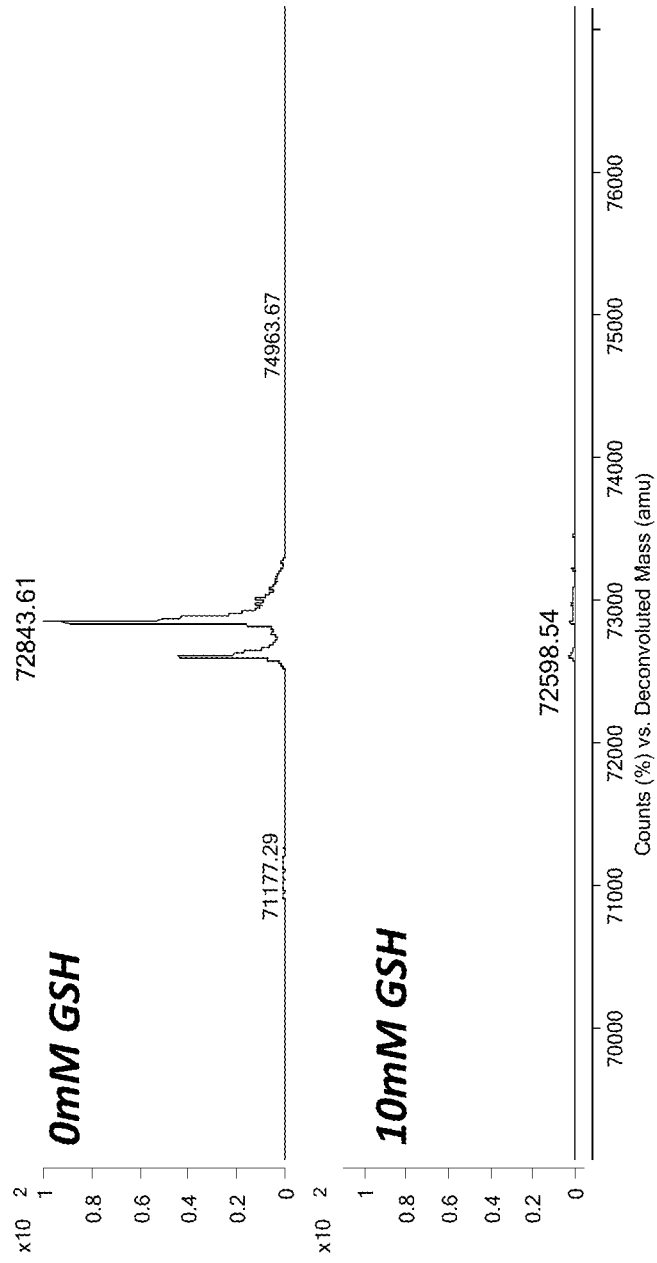
FIG. 7C shows an enlargement of the m/z range of the half antibody peak.

The untreated and GSH treated cell-free culture medium were each processed over MabSURE SELECT and the capture pools were analyzed using ESI-TOF. See FIG. 7A. FIG. 7B shows an enlargement of the m/z range of the bispecific antibody peak (right peak as shown in 7A). FIG. 7C shows an enlargement of the m/z range of the half antibody peak (left peak as shown in 7A).

FIGS. 7A-C show that homodimer and half antibody peak abundances are visibly reduced when 10 mM GSH was added into the culture, demonstrating that bispecific formation is driven by both half-antibody and homodimer content present in the co-culture. The extent each homodimer participates in bispecific antibody formation depends on the particular half antibody.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

What is claimed is:

1. A method of preparing an antibody comprising i) a first heavy chain comprising a knob modification, wherein the first heavy chain is paired with a first light chain, and ii) a second heavy chain comprising a hole modification, wherein the second heavy chain is paired with a second light chain, wherein the knob modification of the first heavy chain interacts with the hole modification of the second heavy chain at an interface, and wherein the first and second heavy chains are linked by at least one interchain disulfide bond, the method comprising the steps of:
   (a) culturing a first host cell and a second host cell, wherein the first host cell expresses the first heavy chain and the first light chain, wherein the second host cell expresses the second heavy chain and the second light chain, and wherein the first host cell and the second host cell are each a mammalian cell;
   (b) adding a reducing agent to a combined culture comprising the first host cell and the second host cell; and
   (c) harvesting a combined culture medium from the combined culture 4 hours to 24 hours after adding the reducing agent to the combined culture, wherein harvesting comprises removing the first host cell and second host cell from the combined culture medium without disrupting cell membranes of the first and second host cells, and wherein the combined culture medium comprises the antibody.

2. The method of claim 1, wherein the combined culture medium is harvested 15 hours after the reducing agent is added.

3. The method of claim 1, wherein the step of harvesting a combined culture medium comprises removing the first host cell and second host cell from the combined culture medium.

4. The method of claim 1, wherein the combined culture medium is incubated for 4 hours to 7 days.

5. The method of claim 1, wherein the first host cell and the second host cell are cultured separately before being combined in the combined culture.

6. The method of claim 1, wherein the knob modification comprises a T366W substitution (EU numbering) and the hole modification comprises two or more amino acid substitutions selected from the group consisting of T366S, L368A, and Y407V (EU numbering).

7. The method of claim 1, wherein the reducing agent is glutathione (GSH).

8. The method of claim 7, wherein the GSH is added at a concentration of about 5 mM to no more than about 20 mM.

9. The method of claim 8, wherein the GSH is added at a concentration of about 15 mM.

10. The method of claim 1, wherein the mammalian cell is a CHO cell.

11. The method of claim 1, wherein the mammalian cell is a stable cell line.

12. The method of claim 6, wherein the hole modification comprises the amino acid substitutions T366S, L368A, and Y407V (EU numbering).

* * * * *